US008216125B2

(12) United States Patent
Wilson et al.

(10) Patent No.: US 8,216,125 B2
(45) Date of Patent: Jul. 10, 2012

(54) SYSTEM AND METHOD FOR POSITIONING A LAPAROSCOPIC DEVICE

(75) Inventors: Roger F. Wilson, Sarasota, FL (US); Willet F. Whitmore, III, Longboat Key, FL (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 890 days.

(21) Appl. No.: 12/257,941

(22) Filed: Oct. 24, 2008

(65) Prior Publication Data
US 2009/0247819 A1 Oct. 1, 2009

Related U.S. Application Data

(63) Continuation-in-part of application No. 11/464,804, filed on Aug. 15, 2006, now abandoned, which is a continuation-in-part of application No. 11/095,586, filed on Apr. 1, 2005, now Pat. No. 7,395,563.

(51) Int. Cl.
A61B 17/00 (2006.01)
(52) U.S. Cl. ....................................... 600/102
(58) Field of Classification Search ............ 600/102, 600/114, 117, 228, 229; 606/130, 227, 248; 5/600, 601, 625–629; 378/204–209
See application file for complete search history.

(56) References Cited

U.S. PATENT DOCUMENTS

| | | | |
|---|---|---|---|
| 3,858,578 A * | 1/1975 | Milo | 600/229 |
| 4,465,069 A | 8/1984 | Barbier et al. | |
| 4,473,912 A | 10/1984 | Scheidel et al. | |
| 4,566,445 A | 1/1986 | Jelsma et al. | |
| 4,583,538 A | 4/1986 | Onik et al. | |
| 4,592,352 A | 6/1986 | Patil | |

(Continued)

FOREIGN PATENT DOCUMENTS
GB 2094590 A 9/1982
(Continued)

OTHER PUBLICATIONS

Christopher Nimsky et al., "Intraoperative Magnetic Resonance Imaging Combined with Neuronavigation: A New Concept, Neurosurgery," vol. 48, No. 5, May 2001, pp. 1082-1091.

(Continued)

*Primary Examiner* — Kevin T Truong
*Assistant Examiner* — Christopher Beccia
(74) *Attorney, Agent, or Firm* — Caesar, Rivise, Bernstein, Cohen & Pokotilow, Ltd.

(57) ABSTRACT

A laparoscopic instrument holder for positioning a laparoscopic device includes a central portion having a first member operatively associated with a second member, the members selectively movable with respect to one another along a central axis, with the central portion having a proximal end defined by the first member and a distal end defined by the second member. The holder also includes at least three proximal rotational joints coupled to the first member proximate the proximal end, at least two distal rotational joints coupled to the second member proximate the distal end, a first ball and socket joint coupled to a distal rotational joint, and a second ball and socket joint coupled to the first ball and socket joint. In addition, the holder includes a clamp configured and dimensioned for retaining a laparoscopic device, with the clamp coupled to the second ball and socket joint, and a coupling portion proximate a first of the proximal rotational joints.

4 Claims, 77 Drawing Sheets

U.S. PATENT DOCUMENTS

| | | | |
|---|---|---|---|
| 4,686,997 A | | 8/1987 | Oloff et al. |
| 4,733,661 A | | 3/1988 | Palestrant |
| 4,791,934 A | | 12/1988 | Brunnett |
| 4,854,305 A | | 8/1989 | Bremer |
| 4,867,404 A | * | 9/1989 | Harrington et al. ............. 606/46 |
| 4,949,927 A | * | 8/1990 | Madocks et al. ........... 248/276.1 |
| 5,224,680 A | | 7/1993 | Greenstein et al. |
| 5,280,427 A | | 1/1994 | Magnusson et al. |
| 5,372,147 A | | 12/1994 | Lathrop, Jr. et al. |
| 5,380,338 A | | 1/1995 | Christian |
| 5,410,769 A | | 5/1995 | Waterman |
| 5,441,042 A | | 8/1995 | Putman |
| 5,499,415 A | | 3/1996 | McKenna |
| 5,513,827 A | | 5/1996 | Michelson |
| 5,537,454 A | | 7/1996 | Korver, II |
| 5,555,897 A | | 9/1996 | Lathrop, Jr. et al. |
| 3,285,099 A | | 11/1996 | Parks |
| 5,571,072 A | * | 11/1996 | Kronner ........................ 600/102 |
| 5,704,900 A | * | 1/1998 | Dobrovolny et al. ......... 600/229 |
| 5,771,513 A | | 6/1998 | Kirchgeorg et al. |
| 5,842,987 A | | 12/1998 | Sahadevan |
| 5,865,780 A | | 2/1999 | Tuite |
| 5,876,325 A | | 3/1999 | Mizuno et al. |
| 5,899,425 A | * | 5/1999 | Corey Jr. et al. ........... 248/276.1 |
| 5,918,844 A | | 7/1999 | Ognier |
| 5,957,423 A | | 9/1999 | Kronner |
| 6,003,174 A | | 12/1999 | Kantrowitz et al. |
| 6,161,237 A | | 12/2000 | Tang et al. |
| 6,199,233 B1 | | 3/2001 | Kantrowitz et al. |
| 6,266,831 B1 | | 7/2001 | Heimbrock |
| 6,322,251 B1 | | 11/2001 | Ballhaus et al. |
| 6,378,149 B1 | | 4/2002 | Sanders et al. |
| 6,499,158 B1 | | 12/2002 | Easterling |
| 6,557,195 B2 | | 5/2003 | Dinkler |
| 6,581,889 B2 | * | 6/2003 | Carpenter et al. ............. 248/160 |
| 6,584,630 B1 | | 7/2003 | Dinkler |
| 6,598,275 B1 | | 7/2003 | Kolody et al. |
| 6,671,904 B2 | | 1/2004 | Easterling |
| 6,681,423 B2 | | 1/2004 | Zachrisson |
| 6,688,564 B2 | * | 2/2004 | Salvermoser et al. ........ 248/160 |
| 6,718,571 B2 | | 4/2004 | Bartels |
| 6,730,020 B2 | | 5/2004 | Peng et al. |
| 6,731,970 B2 | | 5/2004 | Schlossbauer et al. |
| 6,772,461 B2 | | 8/2004 | Gaspar |
| 6,782,571 B1 | | 8/2004 | Josephson et al. |
| 6,821,243 B2 | * | 11/2004 | Pagliuca et al. ............... 600/102 |
| 6,912,959 B2 | | 7/2005 | Kolody et al. |
| 7,020,917 B1 | | 4/2006 | Kolody et al. |
| 7,124,755 B2 | * | 10/2006 | Van Hooser ................. 128/845 |
| 7,159,832 B2 | | 1/2007 | Easterling |
| 7,347,862 B2 | | 3/2008 | Layer |
| 7,395,563 B2 | * | 7/2008 | Whitmore et al. ................. 5/601 |
| 7,546,993 B1 | | 6/2009 | Walker |
| 7,901,418 B2 | * | 3/2011 | Danitz et al. .................. 606/157 |
| 2004/0092810 A1 | | 5/2004 | Daum et al. |
| 2004/0143177 A1 | | 7/2004 | Falbo, Sr. et al. |
| 2004/0176751 A1 | | 9/2004 | Weitzner et al. |
| 2007/0129634 A1 | * | 6/2007 | Hickey et al. ................. 600/439 |

FOREIGN PATENT DOCUMENTS

| | | |
|---|---|---|
| GB | 2354559 A | 11/2000 |
| WO | 9911176 | 3/1999 |
| WO | 02087420 A2 | 11/2002 |
| WO | 2005089113 A2 | 9/2005 |

OTHER PUBLICATIONS

S.H. Heywang-Kobrunner et al., "MR-Guided Percutaneous Vacuum Assisted Biopsy of Enhancing Breast Lesions, " electromedica 67 (1999) No. 2, pp. 37-45.

Th. J. Vogl et al., "MR-Guided Interventions with a DSA-MRI Hybrid System," electromedica 68 (2000) No. 2, pp. 116-121.

G.J. Rubino et al., "Interventional Magnetic Resonance Imaging Guided Neurosurgery-The UCLA Experience with the First 100 Cases," electromedica 68-neuro 2000, pp. 37-46.

Daniel F. Kacher et al., "Design and Implementation of Surgical Instruments, Devices and Receiver Coils for Intraoperative MRI-Guided Neurosurgical and Neuro Ablative Procedures," Automedica, 2001, 00:1-45, SPL Technical Report #205, Surgical Planning Laboratory (SPL), Brigham and Women's Hospital, Boston, MA, posted Mar. 2001, hhttp://splweb.bwh.harvard.edu:800/pages/current_projects.html.

"Computed Tomography, Interventional CT," Koninklijke Philips Electronics N.V., 1 page, printed Jul. 12, 2004, 2 pages printed Oct. 7, 2005, http:/www.medical.philips.com/main/products/ct/products/interventional/.

"Computer Tomography, Multislice CT. Standard Accessories," Koninklijke Philips Electronics N.V., 2 pages printed Jul. 12, 2004, 2 pages printed Oct. 7, 2005, http:www.medical.philips.com/main/products/ct/products/international/.

"Radiation Oncology Systems, ACQSIM CT Simulation," Koninklijke Philips Electronics N.V., 1 page printed Jul. 12, 2004, 2 pages printed Oct. 7, 2005, http:/www.medical.philips.com/main/products/ros/products/acquisim ct/.

International Search Report re PCT/US06/31793 dated Mar. 20, 2007.

Supplementary European Search Report dated Jun. 18, 2010.

* cited by examiner

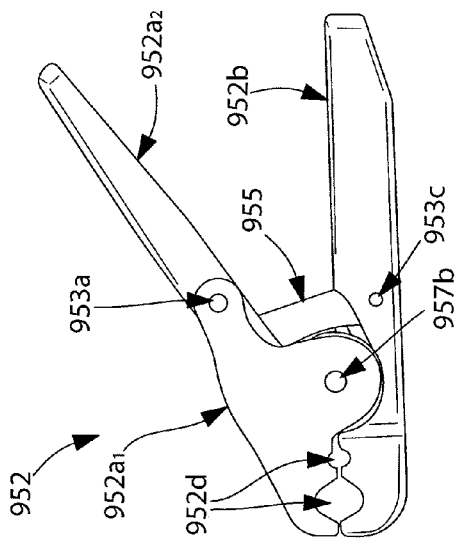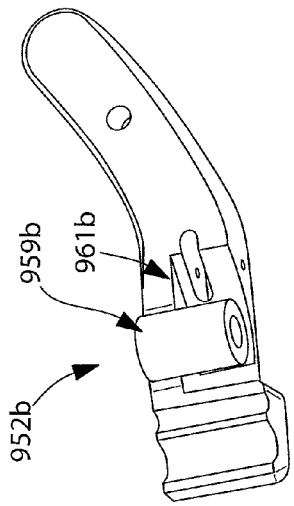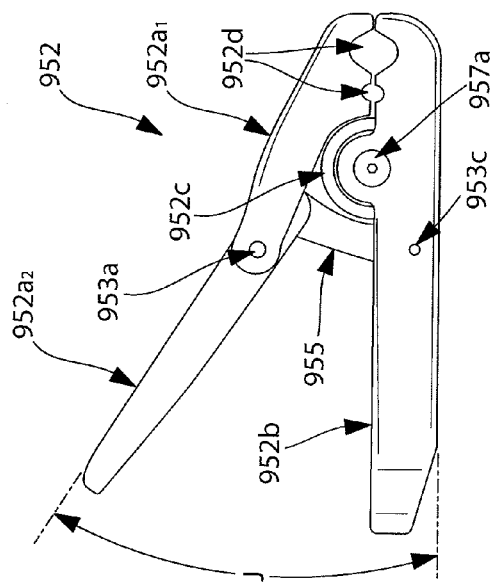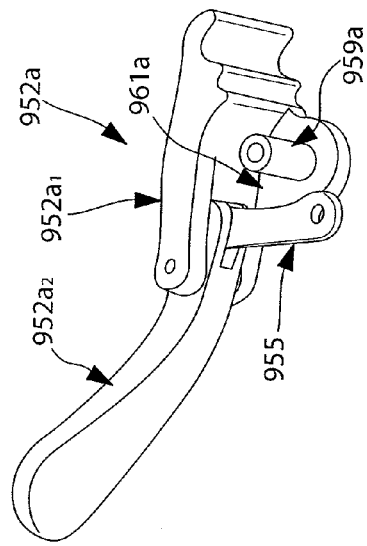

SYSTEM AND METHOD FOR POSITIONING A LAPAROSCOPIC DEVICE

CROSS-REFERENCE TO RELATED APPLICATIONS

The benefits of Provisional Application No. 60/982,398 filed Oct. 24, 2007 and entitled "System and Method for Positioning a Laparoscopic Device" are claimed under 35 U.S.C. §119(e), the entire contents of this provisional application being expressly incorporated herein by reference thereto.

This application also is a continuation-in-part of application Ser. No. 11/464,804 filed Aug. 15, 2006 now abandoned and entitled "System and Method for Positioning a Laparoscopic Device," which (1) is a continuation-in-part of application Ser. No. 11/095,586 filed Apr. 1, 2005, now U.S. Pat. No. 7,395,563 B2, and entitled "Support System for Use When Performing Medical Imaging of a Patient" which claims the benefits of Provisional Application No. 60/559,414 filed Apr. 2, 2004, Provisional Application No. 60/575,792 filed May 28, 2004, and Provisional Application No. 60/614,593 filed Oct. 1, 2004 under 35 U.S.C. §119(e), the priority of which is claimed and the entire contents of each of these applications being expressly incorporated herein by reference thereto, and which (2) claims the benefits of Provisional Application No. 60/709,098 filed Aug. 18, 2005, Provisional Application No. 60/730,853 filed Oct. 28, 2005, Provisional Application No. 60/772,863 filed Feb. 14, 2006, and Provisional Application No. 60/773,638 filed Feb. 16, 2006, each entitled "System for Positioning a Laparoscopic Device," as well as Provisional Application No. 60/821,692 filed Aug. 7, 2006 and entitled "System and Method for Positioning a Laparoscopic Device" under 35 U.S.C. §119 (e), the priority of which is claimed and the entire contents of these provisional applications being expressly incorporated herein by reference thereto.

FIELD OF THE INVENTION

The invention relates to a system for positioning a laparoscopic device. In particular, the invention relates to a holder and curvilinear articulating arm for positioning a laparoscopic device such as an endoscopic camera.

BACKGROUND OF THE INVENTION

During laparoscopy, a minimally invasive surgical procedure in which tissue for example may be removed from the abdomen or chest through a small puncture wound, the laparoscopic surgery is performed with the aid of an endoscopic camera. The camera is placed through a port in the skin into a working cavity and may be used for example to visually examine the interior of the cavity such as the peritoneum or surgical planes or spaces created for purposes of dissection. Typically, the camera includes a light source. Correct positioning and aim of the laparoscopic camera and light throughout a procedure are fundamental to laparoscopy.

Most commonly, the endoscopic camera is held by an assistant who must continually watch the video monitor and hold a steady position until the surgeon requests a change in the field of view. Alternatively, a variety of robotic arms have been designed to hold the camera and move for example on voice command by the surgeon. Such systems include the AESOP® (Automated Endoscopic System for Optimal Positioning) voice controlled robot system and the Zeus® minimal invasive surgical robot system from Computer Motion Inc./Intuitive Surgical Inc. Mechanical/electrical servomotor controlled systems that move by foot controls, palm and fingertip controls include the LAPMAN® by MedSys s.a. of Belgium, while a remote, manual control system da Vinci® is available from Intuitive Surgical Inc.

In addition, a variety of known mechanical frameworks that have multiple adjustment and locking points can be used to hold an endoscopic camera including a laparoscopic retractor from Thompson Surgical Instruments, the Martin Arm System from Gebrüder Martin GmbH & Co. KG, and the Omni-Tract® surgical retractors from Minnesota Scientific Inc. These devices have the capability of holding other laparoscopic instruments as well, although different connections at the instrument interface may be required depending on the instrument and the application.

The first choice for any surgeon is to have a good human assistant, who can continuously and accurately aim and focus the camera and light on the moving surgical field. Unfortunately, good assistance, or any assistance for that matter, is frequently unavailable, and the surgeon must work solo. Also, occasions frequently arise where an assistant's hands may be occupied by other tasks, such as retraction and suction, and in these circumstances other means for holding the camera also are required. The alternatives for holding and positioning the camera cited above then come into play. However, these alternatives each have one or more troublesome drawbacks. The high end robotic arms (such as da Vinci) are expensive, have high maintenance requirements, are time consuming and cumbersome to set up and may have high cost disposable components. They also require an experienced assistant or technician to be present. The simpler, voice controlled (AESOP) or palm radio controlled (LAPMAN) robotic arms also require significant maintenance and set up time, move too slowly for many surgeons, and are hard to precisely control. The mechanical arms and frameworks that are available typically have too many movable parts that require adjustment, require two hands for re-positioning, may have a large footprint near the surgical field, and are very slow to re-position because of the several joints that must be loosened and retightened.

Thompson Surgical Instruments also offers a Flexbar Scope Holder (product #42133C). This device has a clamp to the bedside railing and a set of stainless steel rods that may be clamped at a desired length with right angle clamps to position the base attachment of a curvilinear flexible arm. The arm uses a combination of a screw and cam locking mechanism to achieve an adjustable friction lock of the arm. In this device, the clamp that holds the laparoscopic camera at the free end of the flexible arm has limited capabilities; the clamp becomes locked dimensionally with the arm and is not a universal joint. The design of the scope holder generally requires a user to loosen and then retighten the locking mechanism for the arm whenever it is necessary to reposition the laparoscope.

Thus, there remains a need for better holding and positioning devices for laparoscopic instruments in general and for the laparoscopic camera (laparoscope) in particular. In particular there is a need for a device that will hold a laparoscope steady when it is not in hand, may be quickly re-positioned using one hand, allows quick engagement and disengagement to a laparoscopic instrument, and has a minimal and movable footprint on the surgical field.

SUMMARY OF THE INVENTION

The invention relates to a system for positioning a laparoscopic device, the system having a holder. The holder includes a central portion having a first member operatively associated with a second member, the members selectively movable with respect to one another along a central axis, the central portion having a proximal end defined by the first member and a distal end defined by the second member. The holder also has at least three proximal rotational joints coupled to the first member proximate the proximal end, at least two distal rotational joints coupled to the second member proximate the distal end, a clamp configured and dimensioned for retaining a laparoscopic device, and a coupling portion proximate a first of the proximal rotational joints. A first of the distal rotational joints is coupled to the distal end of the central portion and a second of the distal rotational joints is coupled to the clamp.

In some embodiments, the members may telescope with respect to one another. The second member may be slidably received in the first member. The first member may have a slot and the second member may have a protrusion, the protrusion movable within the slot. For example, the protrusion may include a roller key. Also, in some embodiments, the second member may include a piston member proximate an end thereof, the piston member disposed within the first member. The piston member may be spring-loaded with a spring oriented transverse to the central axis.

The first member may include a receiving end for receiving the second member and a bushing coupled to the receiving end, with the bushing having a plurality of fingers disposed radially with respect to the central axis.

Each of the proximal and distal rotational joints may include a thrust bearing which may be a steel ball thrust bearing. In addition, each of the proximal rotational joints may include a washer abutting a spacer and rotatable with respect to each other. In some embodiments, the spacer may be formed of a material that is polytetrafluoroethylene-based. Each of the distal rotational joints may include a washer abutting a spacer and rotatable with respect to each other. In some embodiments, the spacer may be formed of a material comprising acetal homopolymer. Each of the proximal and distal rotational joints may include a spacer, each of the spacers of the proximal rotational joints having a first thickness and each of the spacers of the distal rotational joints having a second thickness, the first thickness being smaller than the second thickness.

The at least three proximal rotational joints may be three proximal rotational joints that each permit movement in a separate plane, and at least two of the planes may be parallel to one another.

The first of the distal rotational joints may permit rotation about an axis coinciding with the main axis and the second of the distal rotational joints may permit rotation about an axis transverse to the main axis. Also, the second of the distal rotational joints may permit rotation about an axis generally perpendicular to the main axis.

The clamp may include a pair of spring-biased jaw members each having a cover formed of a material softer than aluminum, the clamp being configured and dimensioned to retain the laparoscopic device while contacting the covers. For example, each cover may be formed of polyurethane.

The laparoscopic device may have a cylindrical portion. The first member may be tubular. Each of the proximal and distal rotational joints may have a first portion rotatable with respect to a second portion about a fixed axis. The first and second members may be movable with respect to each other along the central axis but may not be rotatable with respect to each other.

The system may further include a curvilinear articulating arm, the holder being coupled to the curvilinear articulating arm. In addition, the system may further include a tray configured and dimensioned for supporting a mammal, the curvilinear articulating arm being coupled to the tray.

The coupling portion may include a clamp for coupling to a support, wherein the support is selected from the group consisting of a rail of a table and a rail of a bed.

Each proximal rotational joint and each distal rotational joint may permit 360° of rotation about an axis thereof.

The invention also relates to a system for positioning a laparoscopic device including a curvilinear articulating arm and a holder having at least two rotational regions and a clamping portion for receiving the laparoscopic device, the holder being coupled to the curvilinear articulating arm. The at least two rotational regions are permitted to articulate. The holder may further include a central portion with a selectively adjustable length along a central axis, wherein the at least two rotational regions are disposed between the central portion and the clamping portion. In some embodiments, the holder further includes a central portion with a selectively adjustable length along a central axis, the central portion having a proximal end and a distal end, wherein the at least two rotational regions includes at least three proximal rotational joints disposed proximate the proximal end and at least two distal rotational joints disposed between the distal end and the clamping portion. The at least two rotational regions may include a thrust bearing.

In addition, the invention relates to a method of positioning a laparoscopic device in a skin port of a mammal, the method including: coupling the laparoscopic device to a holder comprising a clamping portion and five rotational joints, the laparoscopic device being partially retained in the clamping portion; disposing the laparoscopic device partially within the skin port; positioning the laparoscopic device by selectively rotating portions of the holder with respect to one another. The method may further include positioning the laparoscopic device by selectively adjusting a length of the holder along a central axis. The holder may further include first and second members selectively movable with respect to one another. The length may be selectively adjustable by moving the first and second members with respect to each other. The length may be selectively adjustable by telescoping the first member with respect to the second member. Movement of the first and second members may be restricted to linear movement along the central axis, and the holder may be manually operated.

In some embodiments, the method may further include: coupling the holder to a curvilinear articulating arm; and articulating the curvilinear articulating arm. Also, the method may further include: coupling the curvilinear articulating arm to a tray configured and dimensioned for supporting the mammal. Moreover, the method may further include: coupling the curvilinear articulating arm to a support, wherein the support may be selected from the group consisting of a rail of a table and a rail of a bed. The laparoscopic device may be held in a selected position while disposed partially within the skin port without locking movement of the rotational joints of the holder.

The invention also relates to a method of positioning a laparoscopic device in a skin port of a mammal, the method including: securing the laparoscopic device to a holder comprising at least two rotational joints; coupling the holder to a curvilinear articulating arm; disposing the laparoscopic device partially within the skin port; positioning the laparoscopic device by selectively articulating the curvilinear articulating arm and selectively rotating portions of the holder with respect to one another.

The method may further include: positioning the laparoscopic device by selectively adjusting a length of the holder along a central axis, wherein the holder further comprises first and second members selectively movable with respect to one another, and wherein the length is selectively adjustable by moving the first and second members with respect to each other. Also, the laparoscopic device may be held in a selected position while disposed partially within the skin port without locking movement of the rotational joints of the holder.

The invention further relates to a system for positioning a laparoscopic device such as a camera, the system including a curvilinear articulating arm and a holder that has at least two rotational regions as well as a clamping portion for receiving the laparoscopic device. The holder is coupled to the curvilinear articulating arm, and wherein the at least two rotational regions are permitted to articulate. The at least two rotational regions may be provided by one or more types of structures selected from the group consisting of a rotational joint, a rocking joint, and a living hinge. The at least two rotational regions may be permitted to freely articulate.

The invention also relates to a method of positioning a laparoscopic device in a skin port of a patient, the method including: securing the device in a holder permitted to articulate about at least two rotational regions; coupling the holder to a curvilinear articulating arm; disposing the device partially within the skin port; positioning the device by articulating the curvilinear articulating arm with the device moving in response to the articulation. The orientation of the device, such as a laparoscopic camera, thus may be set. The holder may be permitted to freely articulate about at least two rotational regions.

In yet another exemplary embodiment, the invention relates to a laparoscopic instrument holder for positioning a laparoscopic device including a central portion having a first member operatively associated with a second member, the members selectively movable with respect to one another along a central axis, the central portion having a proximal end defined by the first member and a distal end defined by the second member. The holder also has at least three proximal rotational joints coupled to the first member proximate the proximal end, at least two distal rotational joints coupled to the second member proximate the distal end, a first ball and socket joint coupled to a distal rotational joint, and a second ball and socket joint coupled to the first ball and socket joint. In addition, the holder has a clamp configured and dimensioned for retaining a laparoscopic device, with the clamp coupled to the second ball and socket joint, and a coupling portion proximate a first of the proximal rotational joints. In some embodiments, the members may telescope with respect to one another and the second member may be slidably received in the first member. Each of the proximal and distal rotational joints may have a thrust bearing which may be a steel ball thrust bearing. Each ball and socket joint may have a ball and a washer. In an exemplary embodiment, the first ball and socket joint may have a first ball and the second ball and socket joint may have a second ball, and the first and second balls may be rigidly coupled to each other such as by a shaft. Each socket may have a hole with a rim for limiting angulation of the shaft.

Another exemplary method of positioning a laparoscopic device in a skin port of a mammal includes: securing the laparoscopic device to a holder comprising at least three proximal rotational joints, at least two distal rotational joints, and at least two ball and socket joints; coupling the holder to a curvilinear articulating arm; disposing the laparoscopic device partially within the skin port; positioning the laparoscopic device by selectively articulating the curvilinear articulating arm and selectively orienting portions of the holder with respect to one another. The laparoscopic device may be retained in a clamp, and the positioning may include angulating the clamp using the ball and socket joints. The holder may further have first and second members coupled to one another, and the positioning may include selectively moving the first and second members with respect to each other. In some embodiments, the first and second members may telescope with respect to each other and the holder may be manually operated. The method may further include coupling the curvilinear articulating arm to a patient support.

The present invention further relates to a new set of devices and a method that is particularly suited for holding, positioning and repositioning a laparoscopic camera throughout a laparoscopic surgical procedure. The device includes a holder with joints for permitting rotational movement and positioning of a clamping end for securing a laparoscopic instrument. Fixed positioning and manual re-positioning may be quickly accomplished by simply overcoming the modest frictional resistance to movement within the devices without any mechanical adjustments after the initial set up. The joints of the holder may remain free to move at all times. When the holder is static it preferably will not move, and thus, in effect, becomes self locking because of the physical/mechanical relationship of the various system components including the laparoscopic instrument such as an endoscopic camera which is secured in the holder and extending through the skin of the patient. In addition, the multi-modality holder has alternative functionality for holding and positioning other laparoscopic instruments.

In one exemplary embodiment, the present invention comprises an articulating arm that may be attached at one end to a surgical table, and that has the capability of movement in three dimensions (i.e., at least three degrees (x, y and z) of freedom) at a free end. This arm has a receiving mechanism at the free end that can accept a variety of instrument holding devices one of the main ones of which is a laparoscopic instrument holder for coupling to the free end of the articulating arm and for positioning a laparoscopic device such as an endoscopic camera.

BRIEF DESCRIPTION OF THE DRAWINGS

Preferred features of the present invention are disclosed in the accompanying drawings, wherein:

FIGS. 2A-2I show a first embodiment of a laparoscopic instrument holder according to the present invention, including (2A) a perspective view, (2B) a partial cross-sectional front view of a portion of the holder, (2C) a front view, (2D) a back view, (2E) a first side view, (2F) a second side view, (2G) a bottom view, (2H) a top view, and (2I) a perspective view of the mating of movable clamping jaws 122 and finger rest portion 126;

FIG. 3O shows a perspective view of the holder of FIGS. 3H-3N with a modified member and clamping portion mounted thereon;

FIGS. 5I-5N show another embodiment of a laparoscopic instrument holder according to the present invention, including (5I) a perspective view with a laparoscopic instrument retained by said holder, (5J) a first partial side view, (5K) a second partial side view of the ball and socket assemblies thereof, (5L) a third partial side view of the ball and socket assemblies thereof, (5M) a partial cross-sectional side view of portions of the ball and socket assemblies thereof, and (5N) a perspective view of a ball abutting a washer;

FIGS. 6D-6L show the base handle of FIG. 1, including (6D) a first side view, (6E) a second side view, (6F) a partial perspective view of a first set of components thereof, (6G) a partial side view of a second set of components thereof, (6H) another partial side view of the second set of components thereof, (6I) a front view, (6J) a back view, (6K) a top view, and (6L) a bottom view;

DETAILED DESCRIPTION OF THE PREFERRED EMBODIMENTS

The instrument holders described herein are particularly useful in minimally invasive surgical procedures using a laparoscope (laparoscopic camera), which is a type of endoscope (endoscopic camera). It should be understood that each of the terms laparoscope, laparoscopic camera, endoscope, and endoscopic camera as individually used with respect to any particular embodiment are not meant to limit that embodiment to a laparoscopic or endoscopic context.

Figure 1:
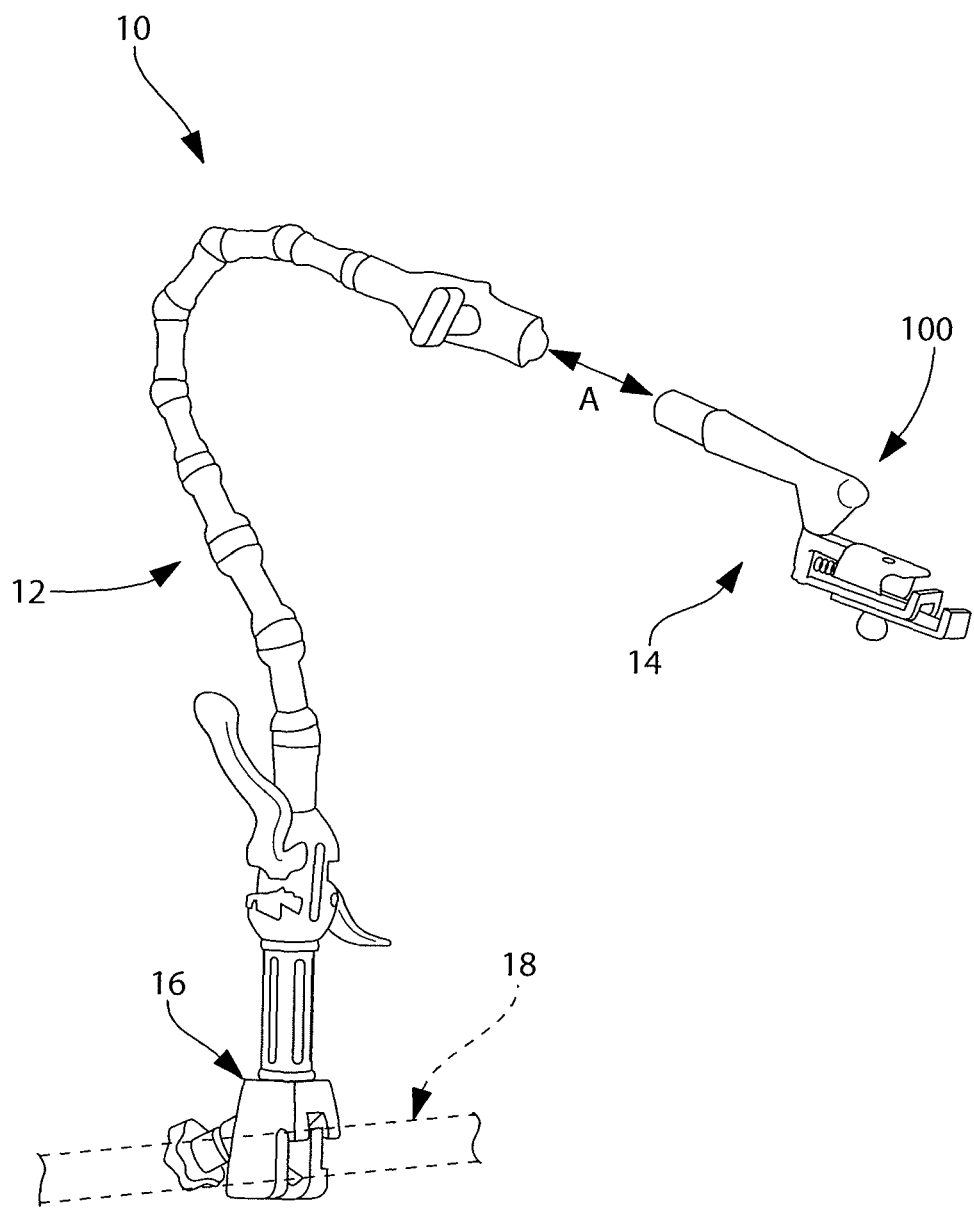
FIG. 1 is a perspective view of a laparoscopic instrument holder system according to the present invention, showing an exemplary arrangement with a holder 100 although the other exemplary holders disclosed herein may instead be used in such a system in place of holder 100.
Figure 2A:
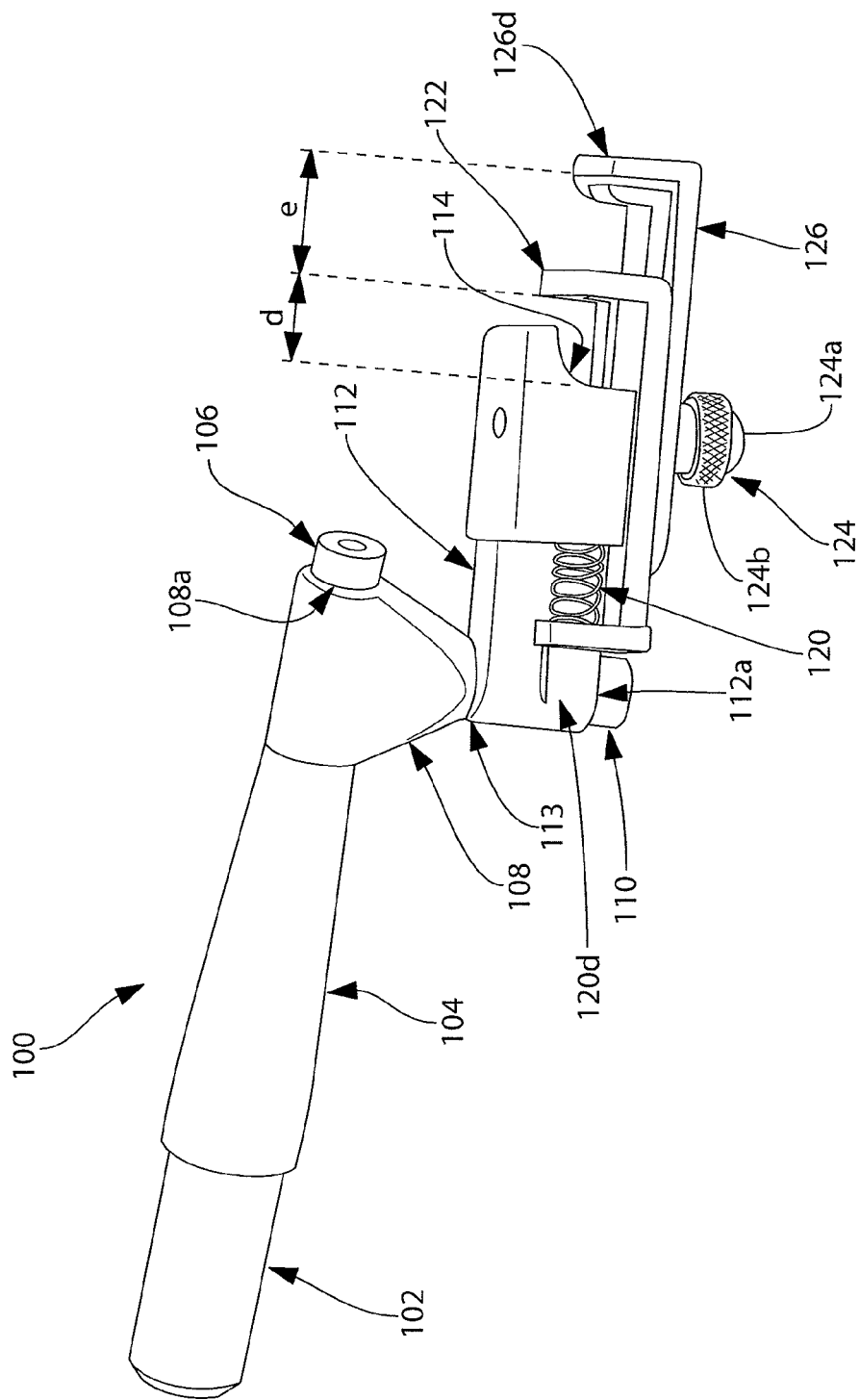
Figure 2B:
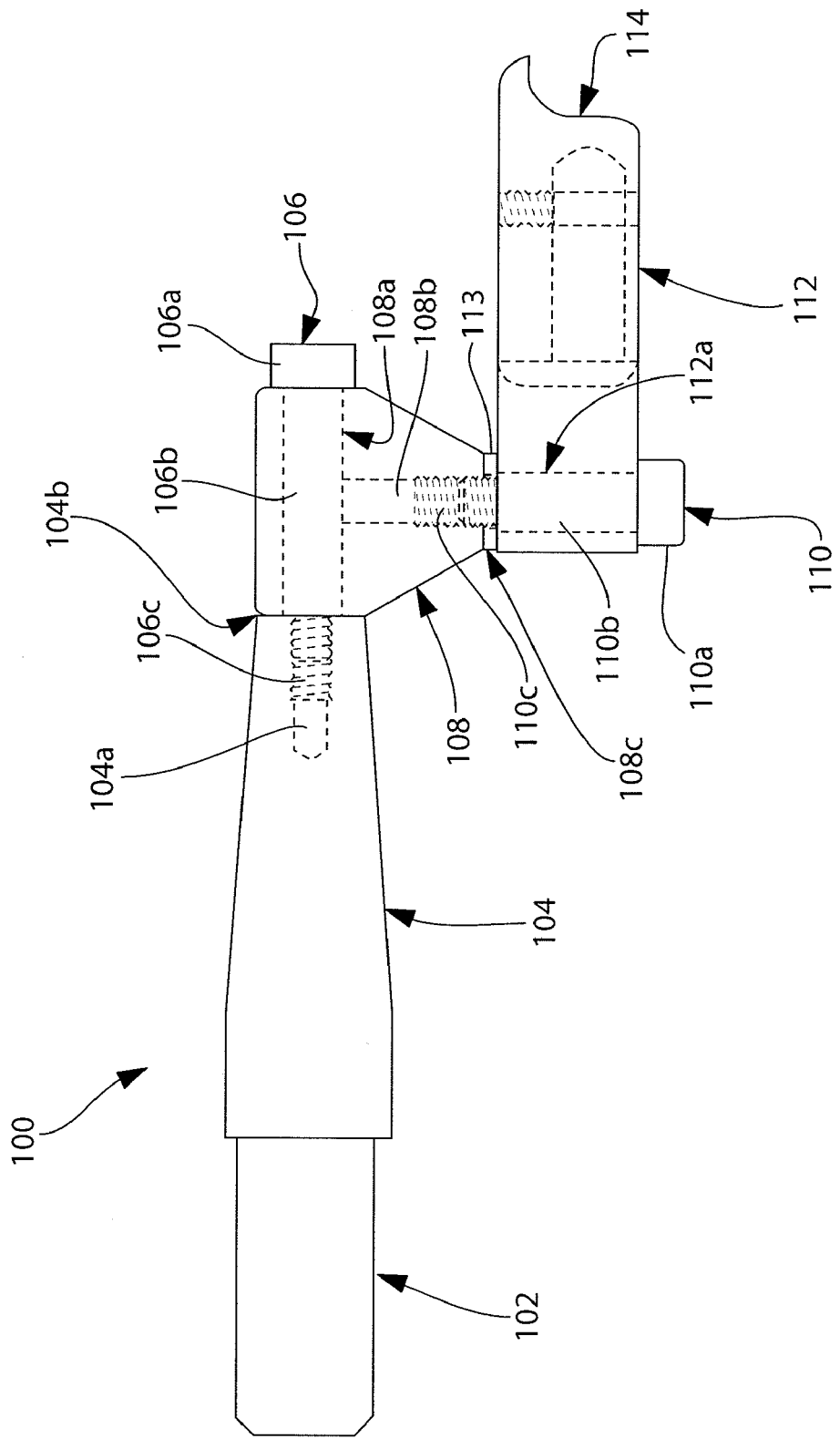
Figure 2C:
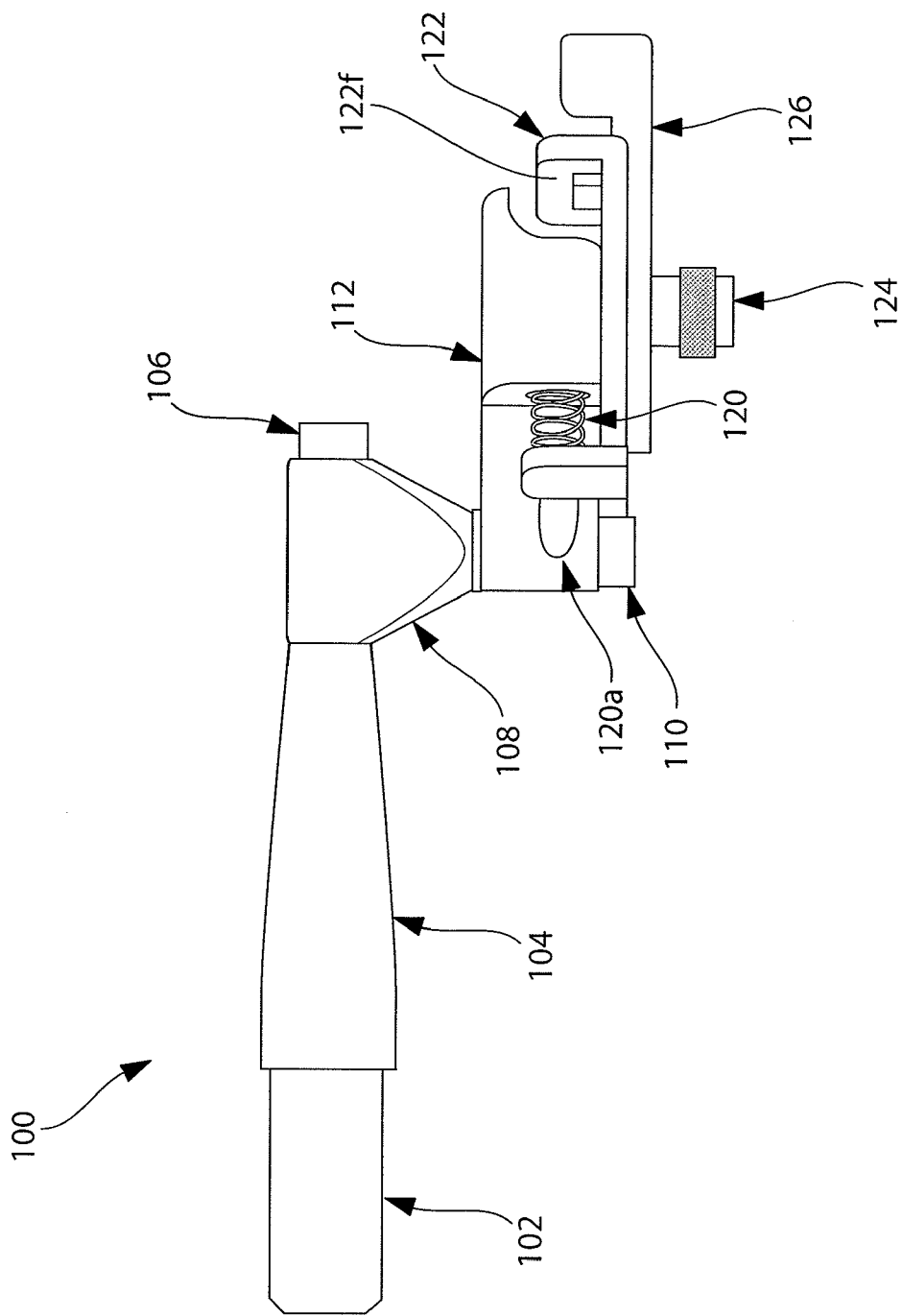
Figure 2D:
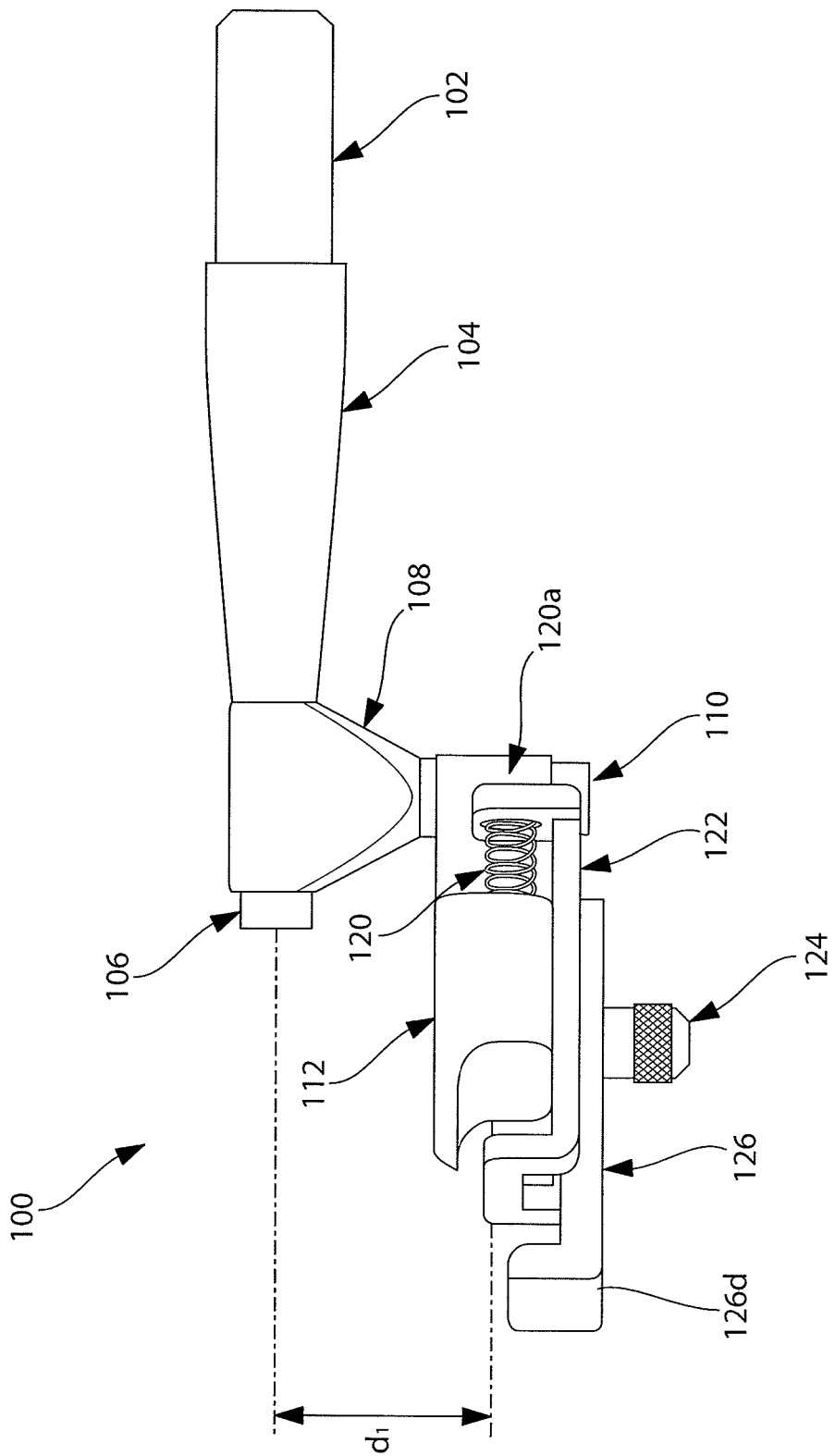
Figure 2E:
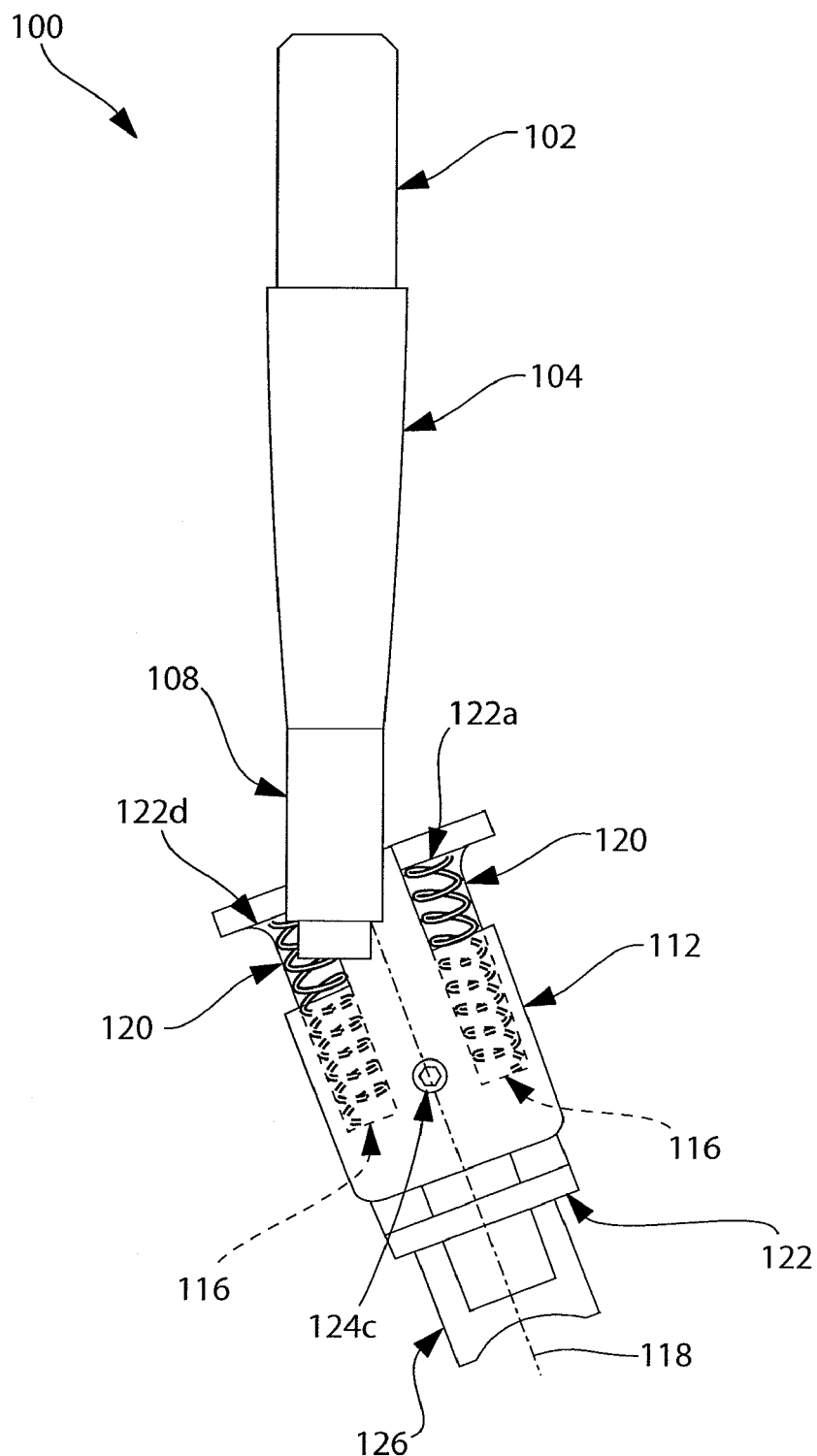
Figure 2F:
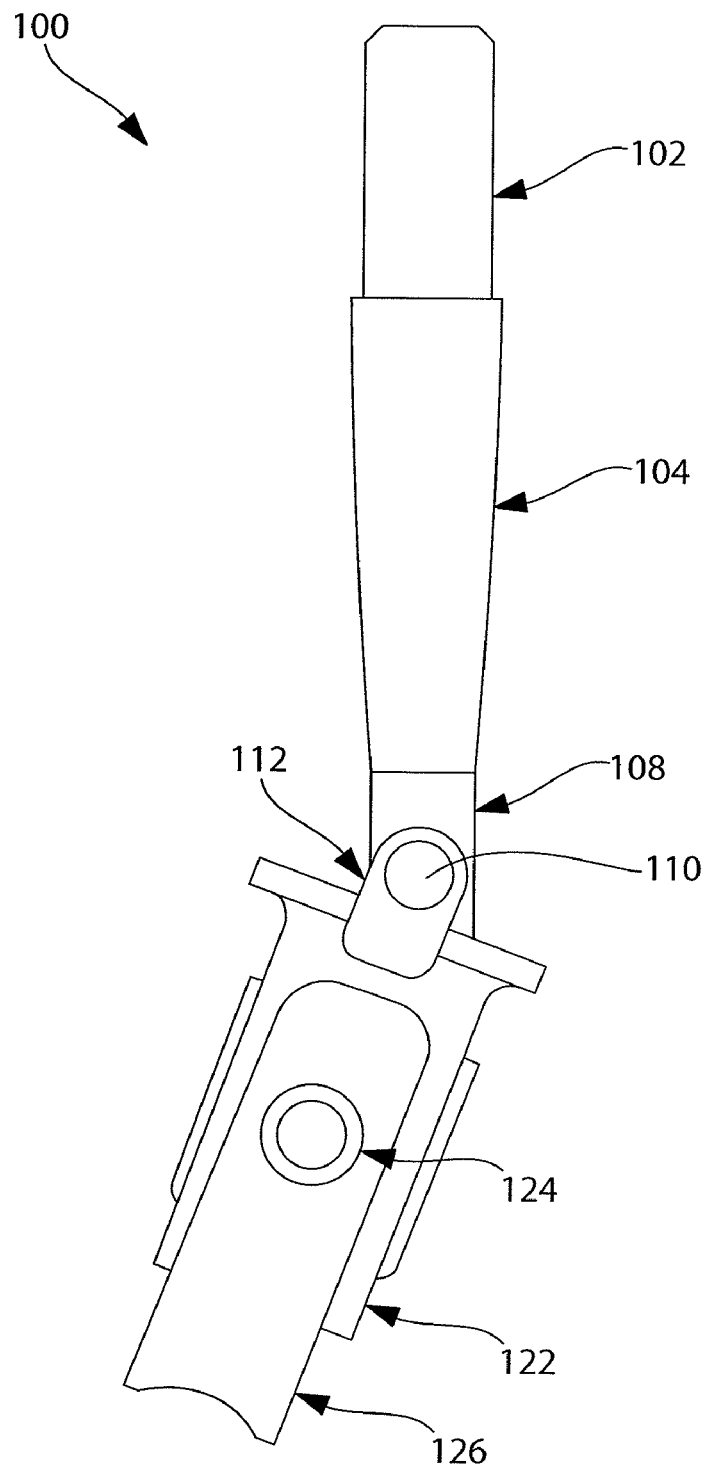
Figure 2G:
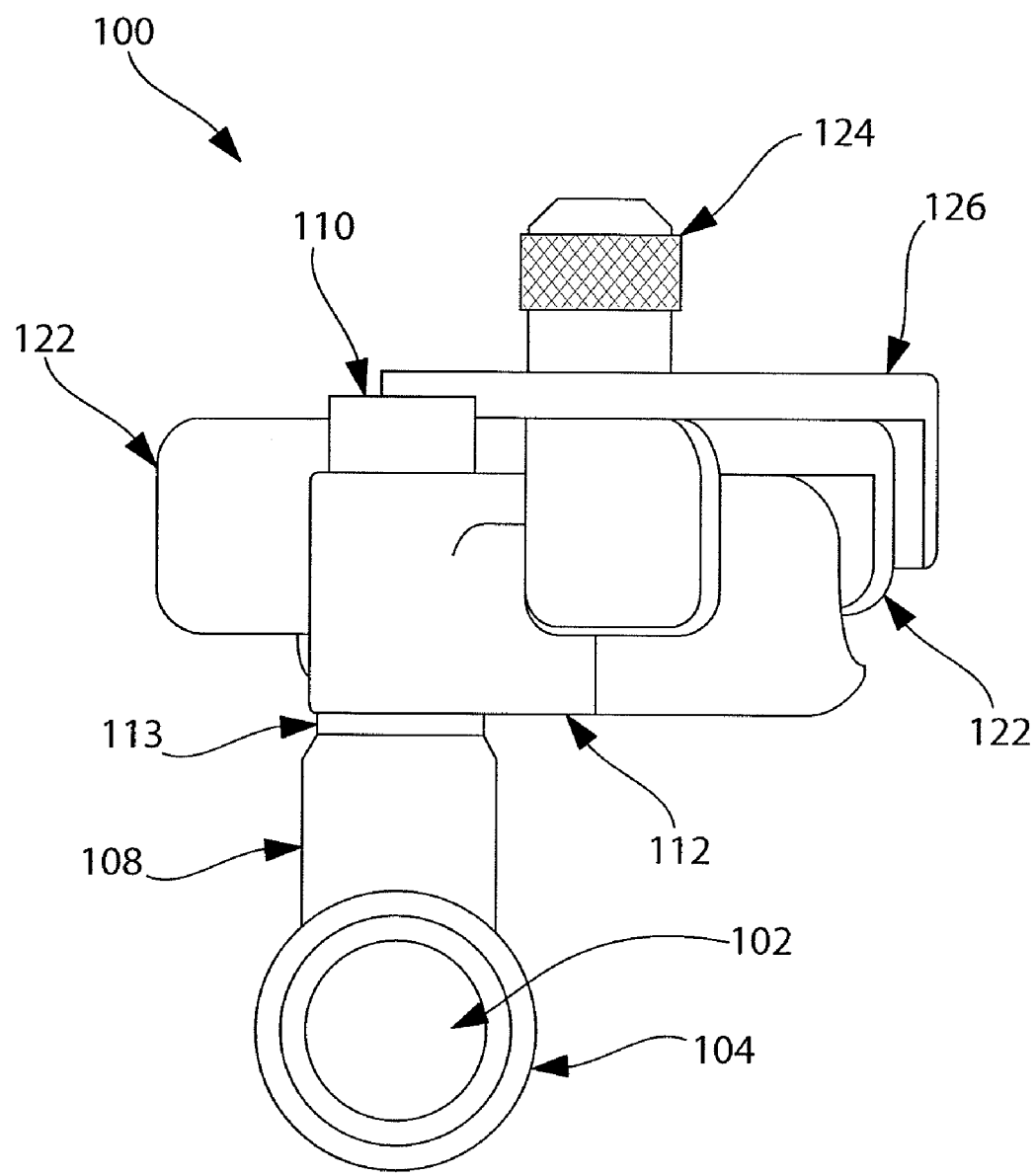
Figure 2H:
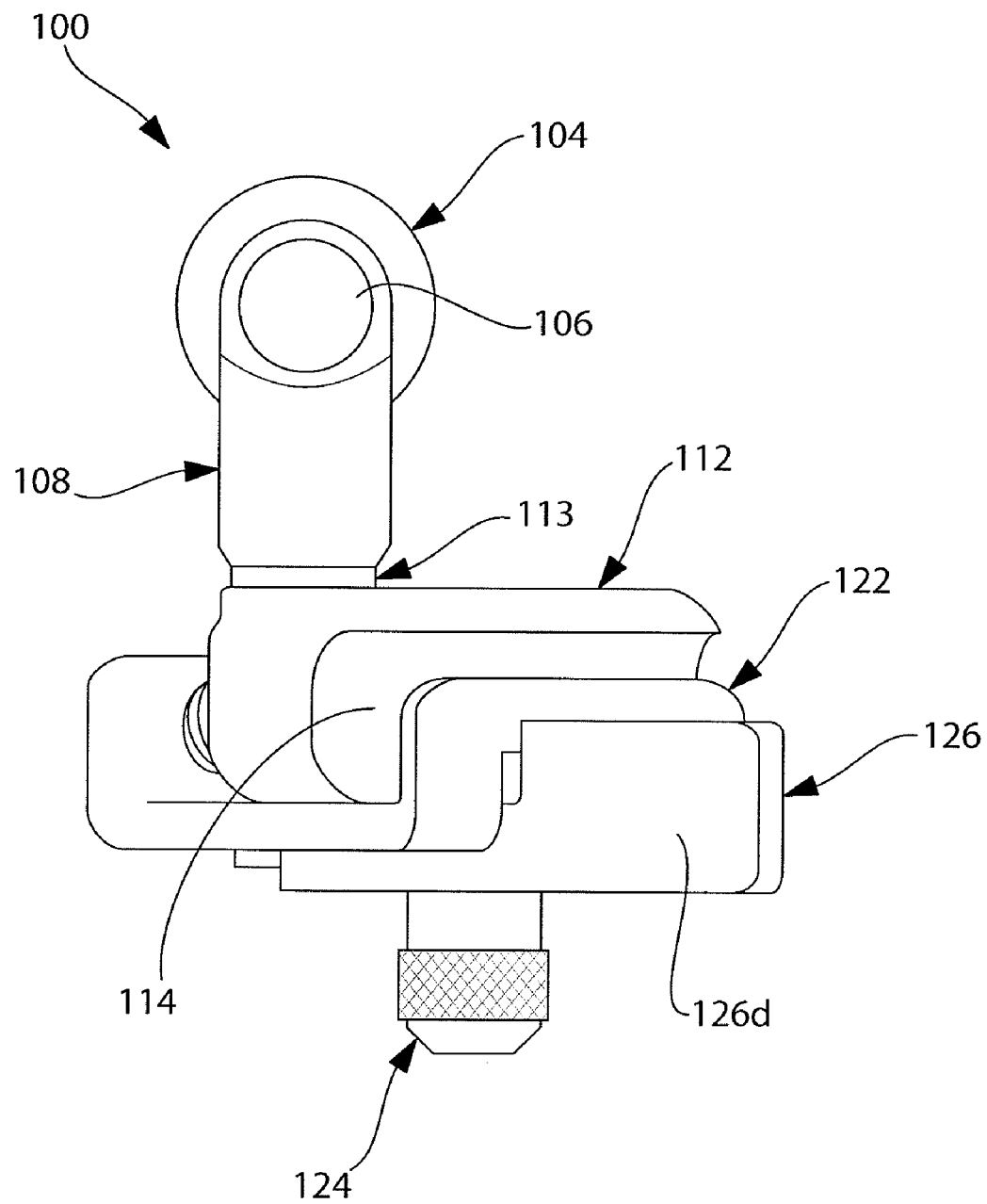

Referring initially to FIG. 1, an exemplary embodiment of a laparoscopic instrument holder system 10 according to the present invention is shown. Holder system 10 includes a curvilinear articulating arm assembly 12 and a laparoscopic instrument holder 14 coupled to assembly 12 as indicated by arrow A. As will be further described, arm assembly 12 includes a clamp 16 at a first free end thereof for coupling system 10 to a structure such as the rail 18 (shown schematically in phantom) of an operating room table.

Turning next to FIGS. 2A-2G, a first exemplary embodiment of a laparoscopic instrument holder 100 according to the present invention is shown. Holder 100 includes a coupling portion 102 in the form of a post. Coupling portion 102 preferably is configured to be received in portion 681 of free handle 662 of articulating arm assembly 12, as will be described later. Holder 100 includes a body portion 104 with a shaft portion 106 extending from an end thereof and forming a first rotational joint. As shown in the partial cross-sectional side view of FIG. 2B, shaft portion 106 may be formed as a screw with a head 106a, a cylindrical shaft 106b, and a threaded end 106c that may be received in threaded hole 104a in body portion 104. A first member 108 is mounted on shaft portion 106 and particularly cylindrical shaft 106b so that shaft portion 106 extends within a bore 108a in first member 108. In the preferred exemplary embodiment, there is minimal frictional resistance to rotational movement of portion 106 and first member 108 with respect to one another so that these components are freely rotatable with respect to one another. However, the tolerance between the components preferably is selected to minimize other play therebetween, and the coupling between the components preferably is such that minimal translation of one component with respect to the other component is permitted along their central axis of rotation.

In alternate embodiments, portion 106 and first member 108 are mechanically associated with each other such that frictional engagement of these components provides limited resistance to rotational movement of portion 106 and first member 108 with respect to each other. However, the frictional engagement preferably permits relative rotation of portion 106 and first member 108 when sufficient manual, external force is applied as by a surgeon using holder 100 during a medical procedure.

Shaft portion 106 and first member 108 are disposed preferably at right angles with respect to each other. First member 108 preferably includes a shaft portion 110 that may be formed as a screw with a head 110a, a cylindrical shaft 110b, and a threaded end 110c that may be received in threaded hole 108b in first member 108. Shaft portion 110 forms a second rotational joint.

Holder 100 further includes a second member 112 that is mounted on shaft portion 110 and particularly cylindrical shaft 110b so that shaft portion 110 extends within a bore 112a in second member 112. In the preferred exemplary embodiment, there is minimal frictional resistance to rotational movement of second member 112 and portion 110 with respect to one another so that these components are freely rotatable with respect to one another. However, the tolerance between the components preferably is selected to minimize other play therebetween, and the coupling between the components preferably is such that minimal translation of one component with respect to the other component is permitted along their central axis of rotation.

In alternate embodiments, portion 110 and second member 112 are mechanically associated with each other such that frictional engagement of these components provides limited resistance to rotational movement of portion 110 and second member 112 with respect to each other. However, the frictional engagement preferably permits relative rotation of portion 110 and second member 112 when sufficient manual, external force is applied as by a surgeon using holder 100 during a medical procedure. Shaft portion 110 and second member 112 are disposed preferably at right angles with respect to each other.

In one preferred exemplary embodiment, the joints formed by rotational movement of portion 106 and first member 108 with respect to each other, and by rotational movement of portion 110 and second member 112 with respect to each other, do not lock and are disposed at about 90° to each other. Preferably, the joints provide loose coupling between the components so that they may freely rock back and forth and be angulated.

In a preferred exemplary embodiment, a stop 104b is created at the transition from a first circumference of body portion 104 to a smaller circumference of cylindrical shaft 106b. Preferably, the length of cylindrical shaft 106b is chosen to be approximately the length of bore 108a in first member 108 so that a portion of first member 108 may be retained between head 106a and body portion 104.

In some alternate embodiments, portion 106 optionally may be tightened to provide substantial resistance to rotational movement of body portion 104 and first member 108 with respect to one another.

Similarly, a stop 108c is created at the transition from a first circumference of first member 108 to a smaller circumference of cylindrical shaft 110b. Stop 108c may include washer 113 disposed between first member 108 and second member 112. Preferably, the length of cylindrical shaft 110b is chosen to be approximately the length of bore 112a in second member 112 so that a portion of second member 112 may be retained between head 110a and first member 108. In the preferred embodiment, portion 110 provides minimal frictional resistance to rotational movement. However, in an alternate embodiment, portion 110 optionally may be tightened to provide substantial resistance to rotational movement of first member 108 and second member 112 with respect to one another.

Second member 112 includes a preferably arcuate clamping portion 114. In addition, a pair of holes 116 extend into second member 112 and are disposed on either side of central longitudinal axis 118 thereof. Holes 116 are configured and dimensioned to receive end portions of springs 120, which extend out of holes 116 and each may partially be disposed in a groove 120a in second member 112. Movable clamping jaws 122 are "spring loaded," with end faces 122a abutting ends of respective springs 120. Thus, springs 120 bias clamping jaws 122 so that face 122f is biased toward clamping portion 114. The slot formed between face 122f and clamping portion 114 is designed so that the spring loading alone is sufficient to hold a laparoscope securely in place therein, but also to let the laparoscope rotate with sufficient frictional resistance to prevent undesired movement.

A set screw assembly 124 releasably and adjustably couples movable clamping jaws 122 to second member 112. Preferably, only slight rotation of assembly 124 is permitted, e.g., one-quarter turn clockwise or counterclockwise. Such turning may loosen or tighten the engagement of movable clamping jaws 122 and finger rest portion 126 with respect to one another thus respectively permitting or hindering movement of spring-loaded clamping jaws 122.

In alternate embodiments, set screw assembly 124 may be any component(s) or manner of fixedly coupling finger rest portion 126 to second member 112.

Figure 21:
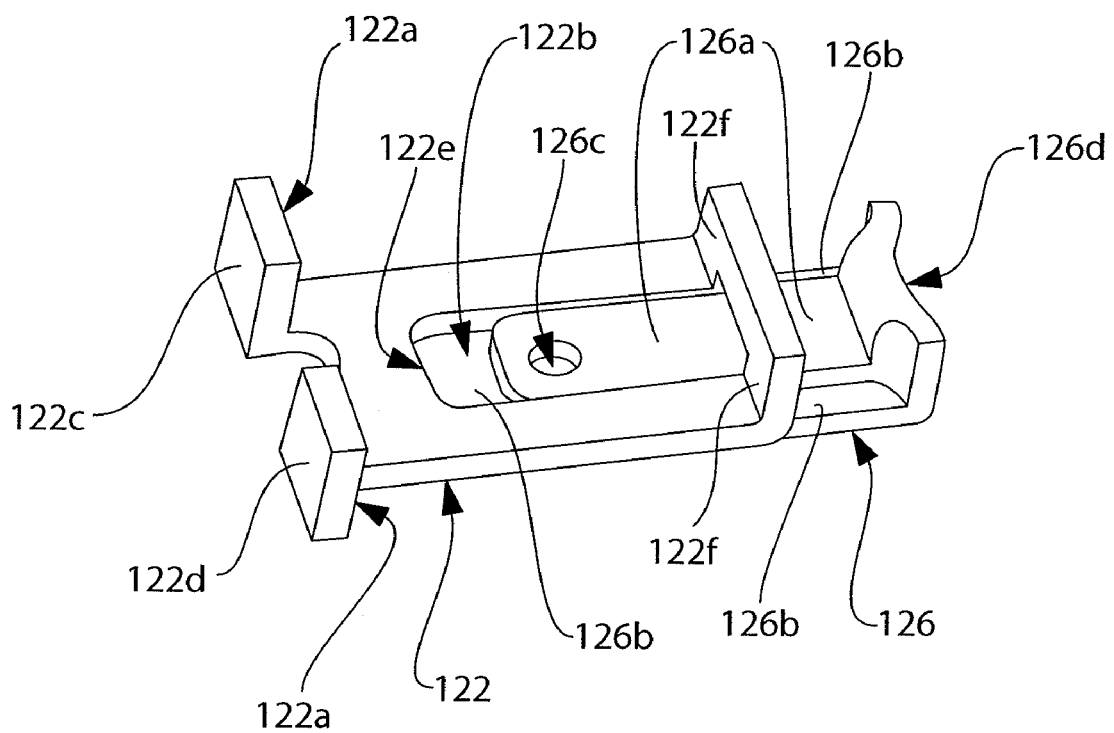

As shown for example in FIG. 21, a finger rest portion 126 includes a central raised portion 126a an a lower face 126b. Central raised portion 126a is slidably received in a slot 122b in movable clamping jaws 122. Travel of clamping jaws 122 is limited and governed by slot 122b which includes a stop portion 122e. Slot 122b is symmetrically disposed with respect to axis 118. Finger rests 122c, 122d are disposed at a free end of movable clamping jaws 122. Finger rest portion 126 is positionally fixed with respect to second member 112, with a threaded screw 124a of screw assembly 124 extending through hole 126c. A knurled knob 124b may be provided as well as a set screw 124c (shown in FIG. 2E) extending into the shaft of screw 124a.

Finger rest portion 126 includes a finger rest surface 126d which provides sufficient surface area for accommodating a portion of a user's finger such as the fleshy tip of a user's thumb. Similarly, finger rests 122c, 122d of movable clamping jaws 122 each provide sufficient surface area for accommodating a portion of another of a user's fingers. Thus, in use, in order to adjust the spacing between arcuate clamping portion 114 and clamping face 122f of movable clamping jaws 122, a user may grasp finger rest portion 126 with his or her thumb disposed on surface 126d and two other fingers disposed on rests 122c, 122d, and squeeze so that the spacing d between arcuate clamping portion 114 and clamping face 122f is increased. Movement of clamping jaws 122 also is limited by the combined lateral distance defined by spacings d, e, particularly because of the fixed position of finger rest portion 126 with respect to second member 112 as well as the maximum travel of surfaces 122*a* of movable clamping jaws 122 with respect to surfaces 112*b* of second member 112.

Thus, an object such as an endoscopic camera may be releasably retained in the space between portion 114 and clamping face 122*f*. Finger rest portion 126 thus serves as a quick-release for such an object. Because clamping end face 122*f* is movable with respect to arcuate clamping portion 114 of second member 112, a variety of sizes and geometries of laparoscopic devices such as a endoscopic camera may be releasably retained within the region between clamping portion 114 and clamping end face 132*a*, 132*b*. Although a single end face 132*a* is shown, other configurations may be used including a bifurcated arrangement of clamping faces, or more than two distinct end faces or extensions such as a three "tine" fork configuration.

In use, when an object such as an endoscopic camera is secured by holder 100, the rotational joints thereof are freely movable. However, once the camera is passed through a hole in a patient's skin, the camera may be aligned to provide the desired view through the use of curvilinear articulating arm assembly 12. Because the size of the entry hole in the patient's skin is limited, such an object disposed therein is unable to move substantially laterally, but may be angulated as by using arm assembly 12.

Arm assembly 12 and holder 100 may be disposed in a sterile sleeve cover so that a sterile environment may be maintained for example when an endoscopic camera is coupled thereto and in use. Sterile covers for holder systems such as system 10 preferably are designed to cover the entire apparatus and slide on easily when articulating arm assembly 12 is in the semi-rigid "gooseneck lamp" mode (i.e. with only lever 682 locked, as will be explained). Such covers, preferably formed of transparent or semi-transparent flexible polymer as known in the art, obviate the need for much cleaning and enable full function and use of system 10 in a sterile field. The scope retained by holder 100 is engaged by opening the spring-loaded slot between face 122*f* and clamping portion 114 and working the mechanism of holder 100 through the cover, invaginating the cover into this slot with the scope then retained. The cover preferably withstands repeated engage/disengage cycles and scope rotations.

A variety of materials may be used to form the holder systems of the present invention. For example, components may be formed of polymer such as injection molded polymer, or metallic materials such as aluminum. Wherein springs are used, the springs for example may be formed of steel.

Although the center of second member 112 of holder 100 may be offset a distance $d_1$ from the central longitudinal axis of coupling portion 102 and body portion 104, in some embodiments first member 108 may be configured so that the center of second member 112 may be aligned to be coaxial with the central longitudinal axis of coupling portion 102 and body portion 104.

Turning to FIGS. 3A-3G, a second exemplary embodiment of a laparoscopic instrument holder 300 according to the present invention is shown. Holder 300 includes a coupling portion 302 in the form of a post that optionally may include a circumferential groove therein (not shown). Coupling portion 302 preferably is configured to be received in portion 82 of free handle 62 of articulating arm assembly 14, as will be described later. Holder 300 includes a body portion 304 with a preferably cylindrical free end portion 306 forming a first rotational joint. In particular, a first member 308 is mounted on end portion 306 so that end portion 306 extends within a bore 308*a* in first member 308. In the preferred exemplary embodiment, there is minimal frictional resistance to rotational movement of portion 306 and first member 308 with respect to one another so that these components are freely rotatable with respect to one another. However, the tolerance between the components preferably is selected to minimize other play therebetween, and the coupling between the components preferably is such that minimal translation of one component with respect to the other component is permitted along their central axis of rotation.

In alternate embodiments, portion 306 and first member 308 are mechanically associated with each other such that frictional engagement of these components resists rotational movement of portion 306 and first member 308 with respect to each other. However, the frictional engagement preferably permits relative rotation of portion 306 and first member 308 when sufficient manual, external force is applied as by a using holder 300 surgeon during a medical procedure.

End portion 306 and first member 308 are disposed preferably at right angles with respect to each other. First member 308 preferably includes a cylindrical free end portion 310 forming a second rotational joint.

Holder 300 further includes a second member 312 that is mounted on end portion 310 so that end portion 310 extends within a bore 312*a* in second member 312. Again, in the preferred exemplary embodiment, there is minimal frictional resistance to rotational movement of portion 310 and second member 312 with respect to one another so that these components are freely rotatable with respect to one another. However, the tolerance between the components preferably is selected to minimize other play therebetween, and the coupling between the components preferably is such that minimal translation of one component with respect to the other component is permitted along their central axis of rotation.

In alternate embodiments, portion 310 and second member 312 are mechanically associated with each other such that frictional engagement of these components resists rotational movement of portion 310 and second member 312 with respect to each other. However, the frictional engagement preferably permits relative rotation of portion 310 and second member 312 when sufficient manual, external force is applied as by a surgeon using holder 300 during a medical procedure.

End portion 310 and second member 312 are disposed preferably at right angles with respect to each other.

Second member 312 includes a clamping portion 314 that may be arcuate such as U-shaped or may be another retaining shape such as V-shaped. In addition, a pair of holes 316 extend into second member 312 and are disposed on either side of central longitudinal axis 318 thereof. Holes 316 are configured and dimensioned to receive end portions of springs 320, which extend out of holes 316. Movable clamping jaws 322 are "spring loaded," with end faces 322*a*, 322*b* abutting ends of respective springs 320. A set screw assembly 324 and respective washer 326 releasably and adjustably couples movable clamping jaws 322 to second member 312. As shown for example in FIG. 3E, which shows a view with screw assembly 324 and washer 326 removed, a slot 328 guides movement of movable clamping jaws 322 along axis 318, with the shaft portion of screw assembly 324 being threadably received in central threaded hole 330 in second member 312. Oval shaped slot 328 permits limited movement, with the shaft of screw assembly 324 being stopped from further movement at either end of slot 328.

Clamping end faces 332*a*, 332*b* that are movable with respect to arcuate clamping portion 314 of second member 312, and thus a variety of sizes and geometries of laparoscopic devices such as a endoscopic camera may be releasably retained within the region between clamping portion 314 and clamping end faces 332*a*, 332*b*. Although end faces 332*a*, 332*b* are shown in a bifurcated arrangement, other configurations may be used including a single clamping face such as a larger end face 332a or 332b, or more than two distinct end faces or extensions such as a three "tine" fork configuration.

In some embodiments, screw assembly 324 may include a threaded screw 324a, a knurled thumb portion 324b, and a set screw 324c (shown in FIG. 3D) extending into the shaft of screw 324a.

Holders 100, 300 thus each incorporate a system of freely articulating joints and that supports a clamp for a laparoscope which may be aligned and attached along the long axis of the laparoscope. The instrument shaft may be held in alignment within the clamp opening by the spring-loaded clamp or in an alternate embodiment by using elastic band(s). The clamping mechanism of holders 100, 300 preferably is of sufficient tension to hold the laparoscope in fixed alignment with the clamp body and yet allow rotation of the laparoscope about its long axis within the clamp. Proper functioning of this mechanism will allow for simple fixation of holder 100, 300 to secure the laparoscope in a steady position without actually locking the individual joints in the universal system. Such a retention is permitted because the laparoscope shaft is firmly attached in three dimensions to the joint at the end of holder 100, 300 and also passes through a second joint (the laparoscopic port) that is fixed in two dimensions at the skin. By positioning holder 100, 300, the camera may be positionally fixed unless the various frictional resistances previously set and controlled are overcome.

This design and method allows instantaneous and free movement and instant "re-locking" of the laparoscope position merely by relying on frictional resistance of the arm and clamp that is easily overcome for example by articulation by a surgeon, when desired, preferably by one handed positioning and re-positioning. Advantageously, this laparoscope holder system 100, 300 is very simple mechanically, yet quick, reliable and easy to use. Also, it is a very quick and simple process to engage or disengage the laparoscope when desired.

The rotational joint provided, for example, by the coupling of end portion 310 and second member 312 preferably allows a 360° range of rotation, because the range of motion required for the laparoscope is extreme. Offsetting the points of rotation of the joints is one preferred design solution.

In use, a straight, rod-like laparoscope extends both above and below the point of attachment of any clamp that is used to grasp it. Typically the laparoscope has power/light cords attached at the outer end that increase bulk in that region. Offsetting the rotational joints advantageously may permit better clearance between the outer end of holder 100, 300 proximate second member 112, 312 and the bulkier external end of the laparoscope.

Referring next to FIGS. 3H to 3O, a third exemplary embodiment of a laparoscopic instrument holder 400 according to the present invention is shown.

Holder 400 includes a coupling portion 402 in the form of a post that optionally may include a circumferential groove therein (not shown). Coupling portion 402 preferably is configured to be received in portion 82 of free handle 62 of articulating arm assembly 14, as will be described later. Holder 400 includes a body portion 404 with a preferably threaded hole 406 formed therein. A rotatable cradle 408 is mounted on a free end 404a of body portion 404, with a washer 410 disposed therebetween. A hole 412 with a upper broadened portion 412a is disposed in cradle 408 and is configured and dimensioned to receive the shaft and head of a threaded screw 414. Rotation of cradle 408 about longitudinal axis 416 is permitted.

In one exemplary embodiment, body portion 404, washer 410, and cradle 408 are mechanically associated with each other such that there is minimal frictional resistance to rotational movement between components so that cradle 408 and screw 414 are freely rotatable with respect to one another (screw 414 includes an unthreaded portion for this purpose). However, the tolerance between the components preferably is selected to minimize other play therebetween, and the coupling between the components preferably is such that minimal translation of one component with respect to the other component is permitted along their central axis of rotation. In alternate embodiments, frictional engagement of these components resists rotational movement of these components with respect to each other. However, the frictional engagement preferably permits relative rotation of portion 404 and first member 408 when sufficient manual, external force is applied as by a surgeon using holder 400 during a medical procedure.

Cradle 408 includes spaced, preferably parallel extensions 418 defining a space 420. Aligned holes 422a, 422b in respective extensions 418 receive a rod-shaped member 424 that extends therethrough. Member 424, for example, may be press-fit in holes 422a, 422b so as to be fixed therein. A first clamping portion 426 with a preferably generally C-shaped or arcuate face 426a is mounted on member 424, such as by member 424 extending through a hole in portion 426. First clamping portion 426 is disposed between extensions 418 and is permitted to swivel on member 424 about swivel or rotational axis 428.

In one exemplary, preferred embodiment, there is minimal frictional resistance to rotational movement of member 424 and first clamping portion 426 with respect to one another so that these components are freely rotatable with respect to one another. However, the tolerance between the components preferably is selected to minimize other play therebetween, and the coupling between the components preferably is such that minimal translation of one component with respect to the other component is permitted along their central axis of rotation.

In alternate embodiments, member 424 and first clamping portion 426 may be mechanically associated with each other such that frictional engagement of these components resists rotational movement of these components with respect to each other. However, the frictional engagement preferably permits relative rotation of member 424 and first clamping portion 426 when sufficient manual, external force is applied as by a surgeon using holder 400 during a medical procedure.

In a preferred embodiment, axes 416, 428 are oriented perpendicular to one another.

Figure 3A:
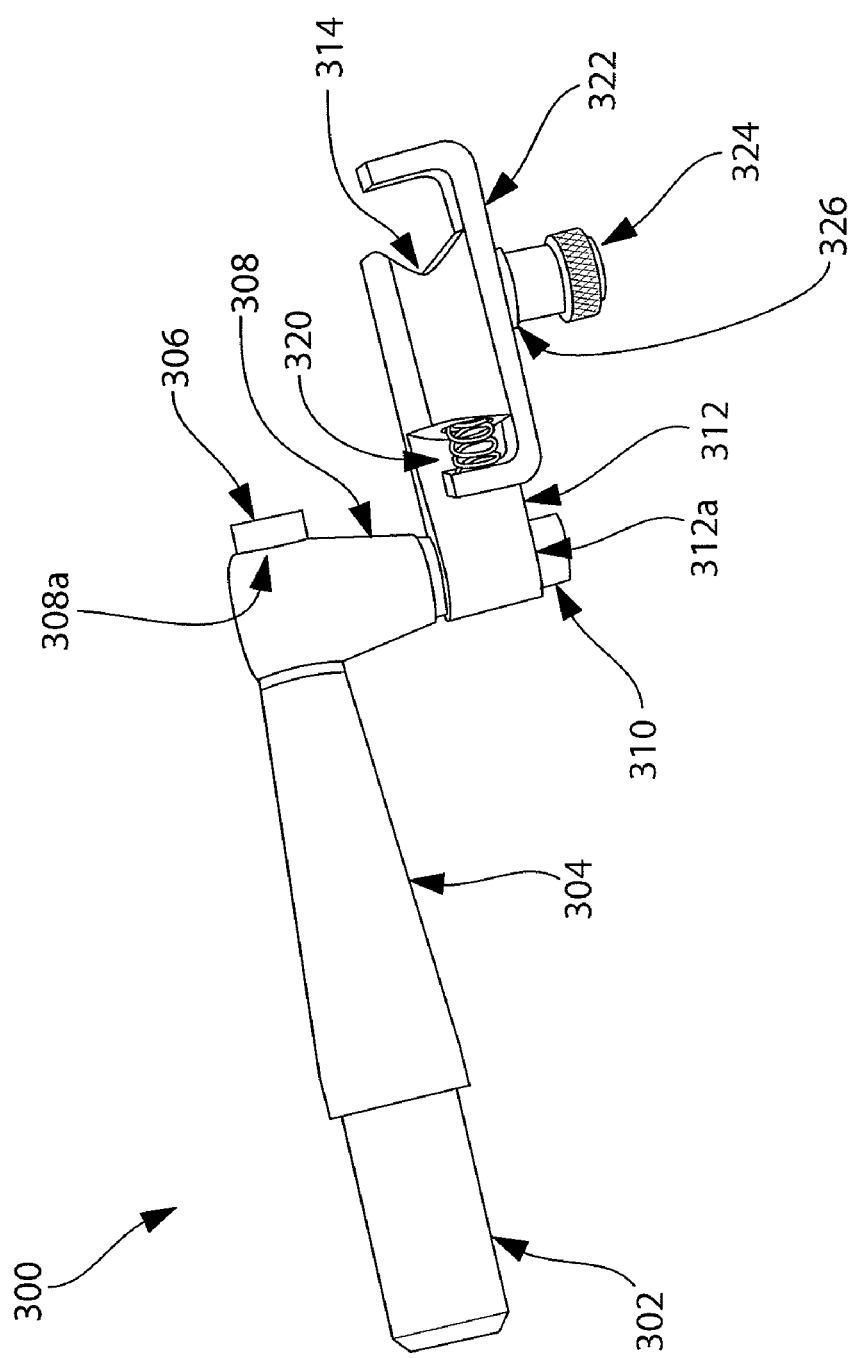
FIGS. 3A-3G show another embodiment of a laparoscopic instrument holder according to the present invention, including (3A) a perspective view, (3B) a front view, (3C) a back view, (3D) a first side view, (3E) a second side view, (3F) a bottom view, and (3G) a top view.
Figure 3B:
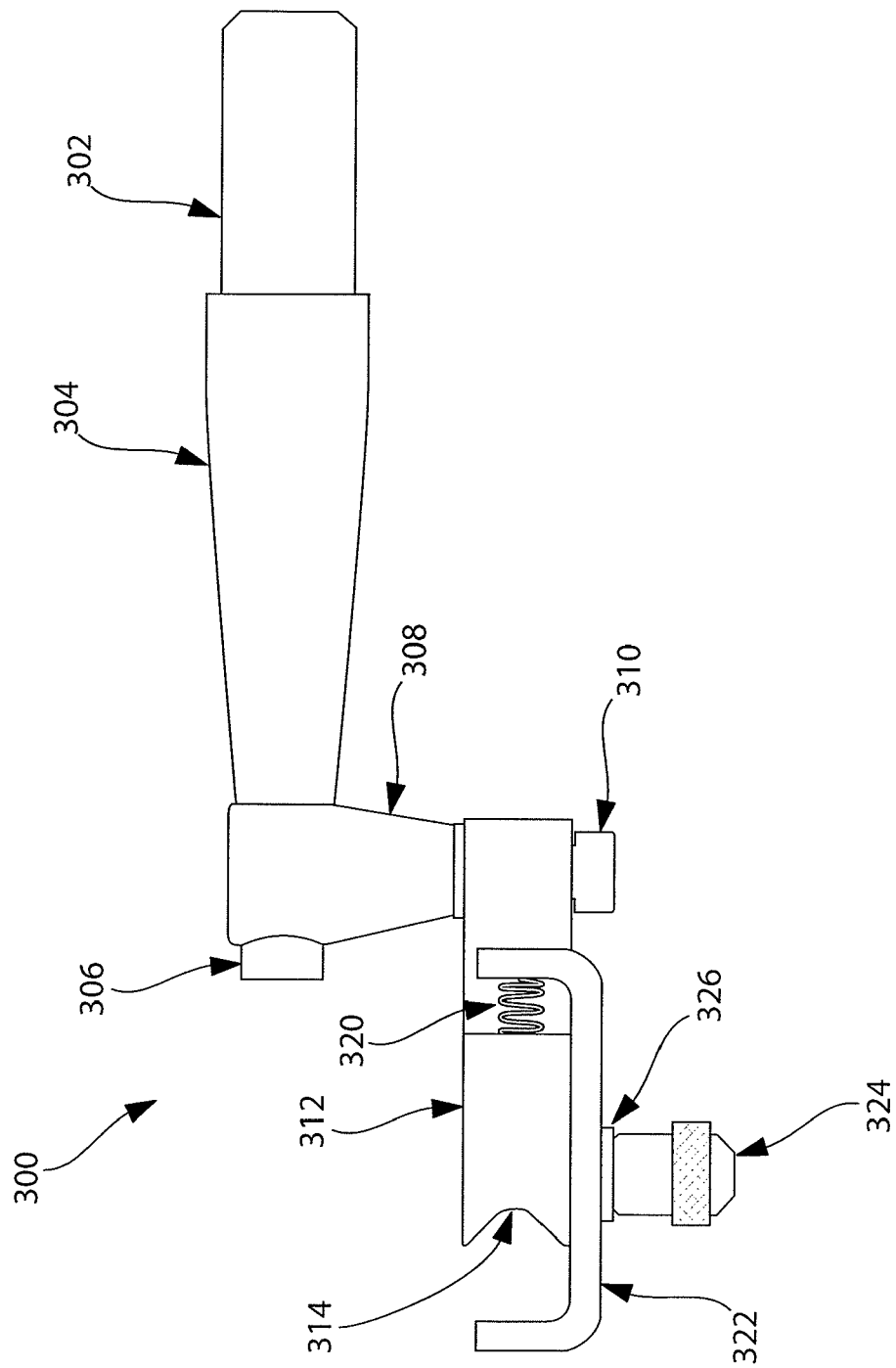
Figure 3C:
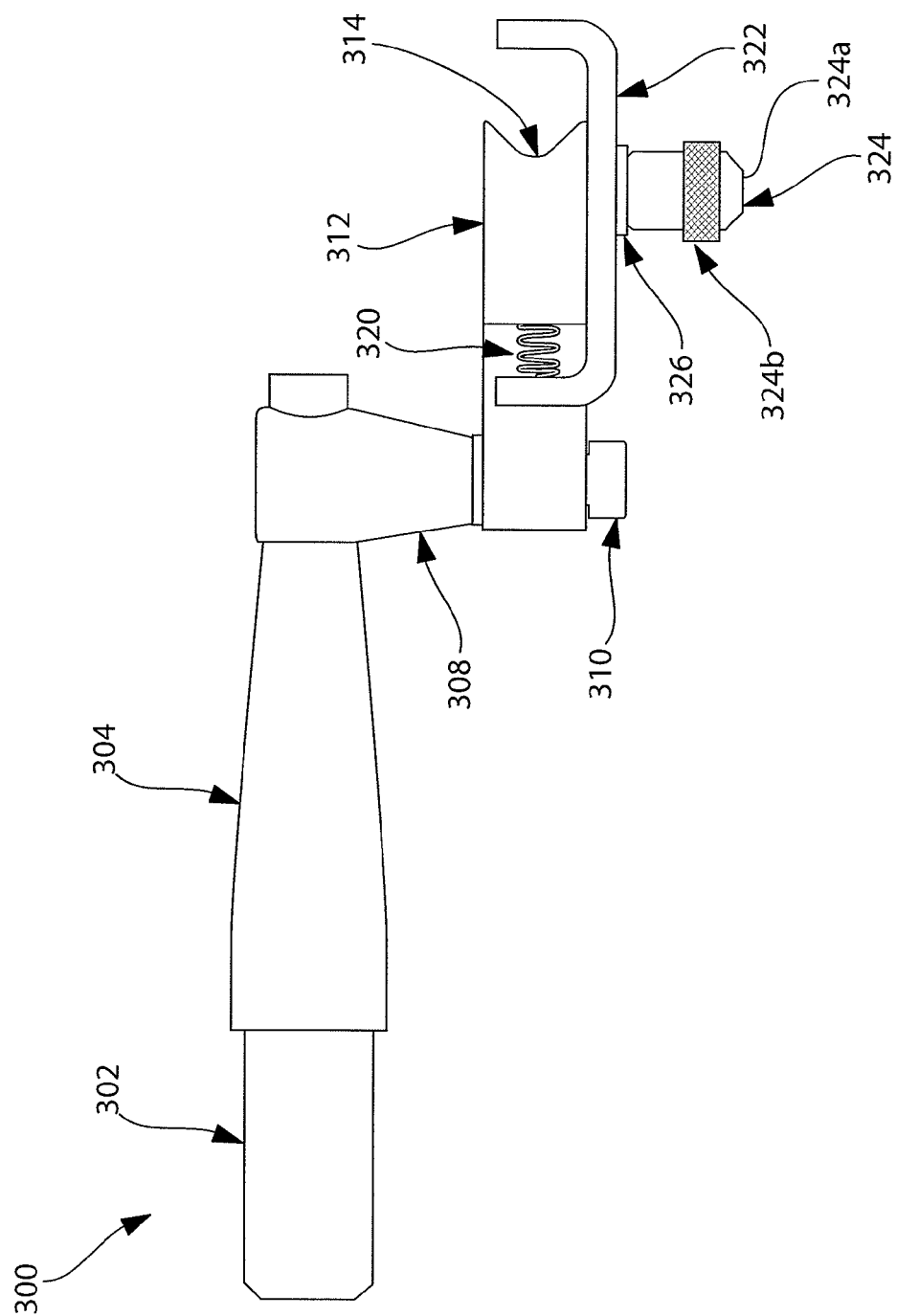
Figure 3D:
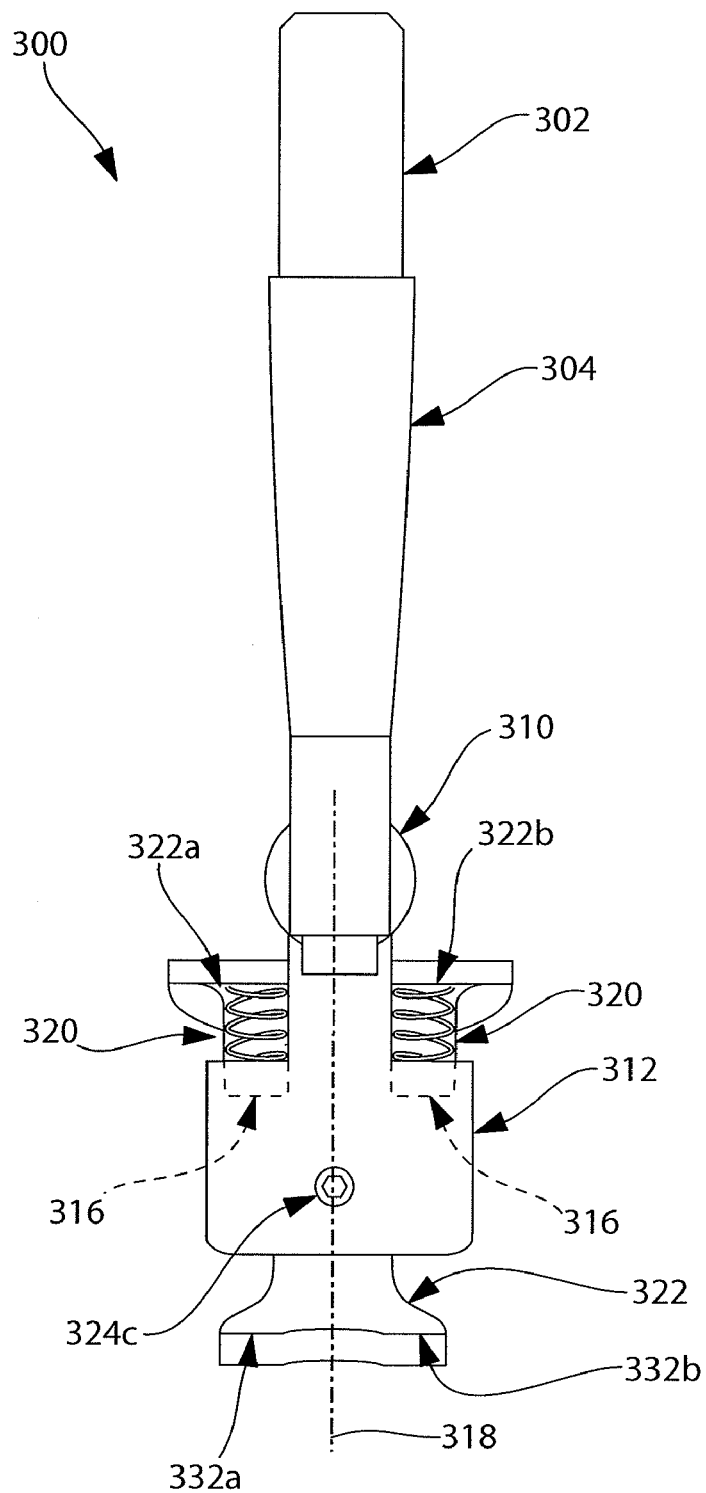
Figure 3E:
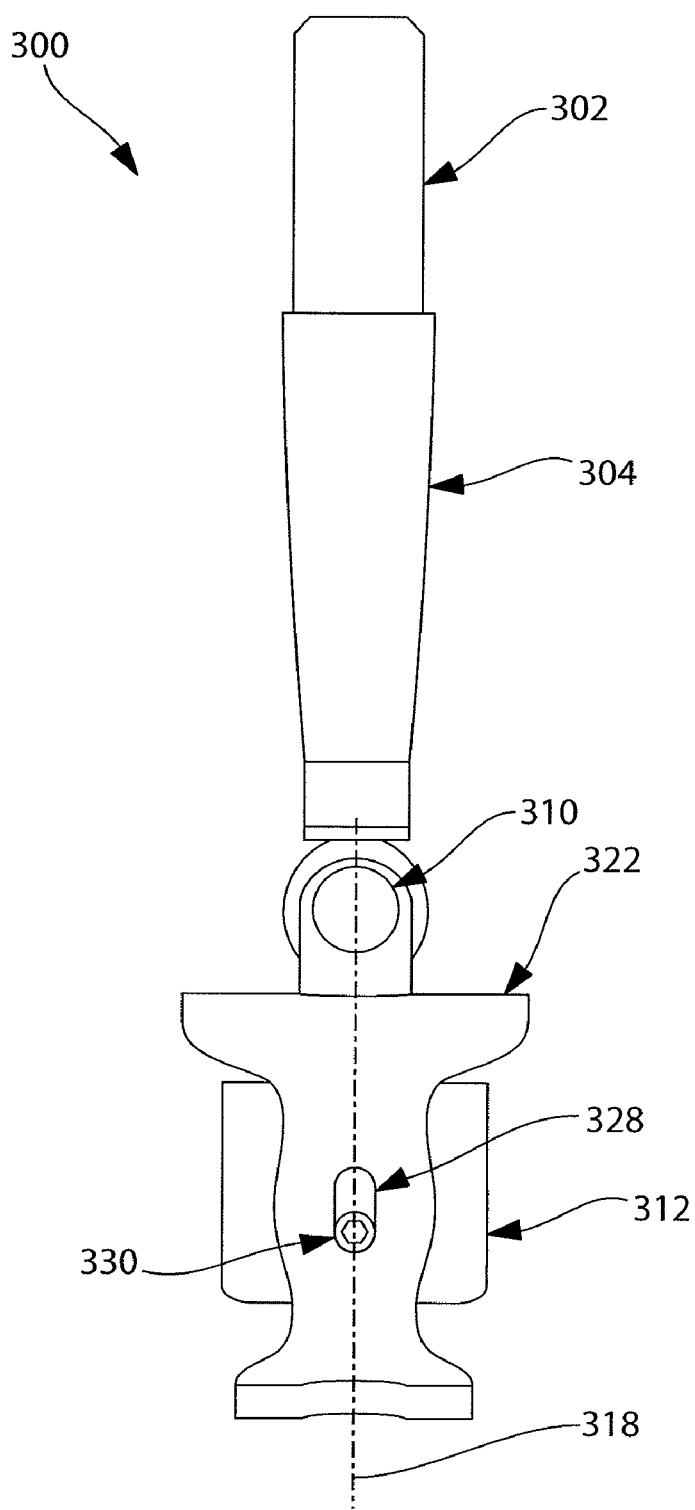
Figure 3F:
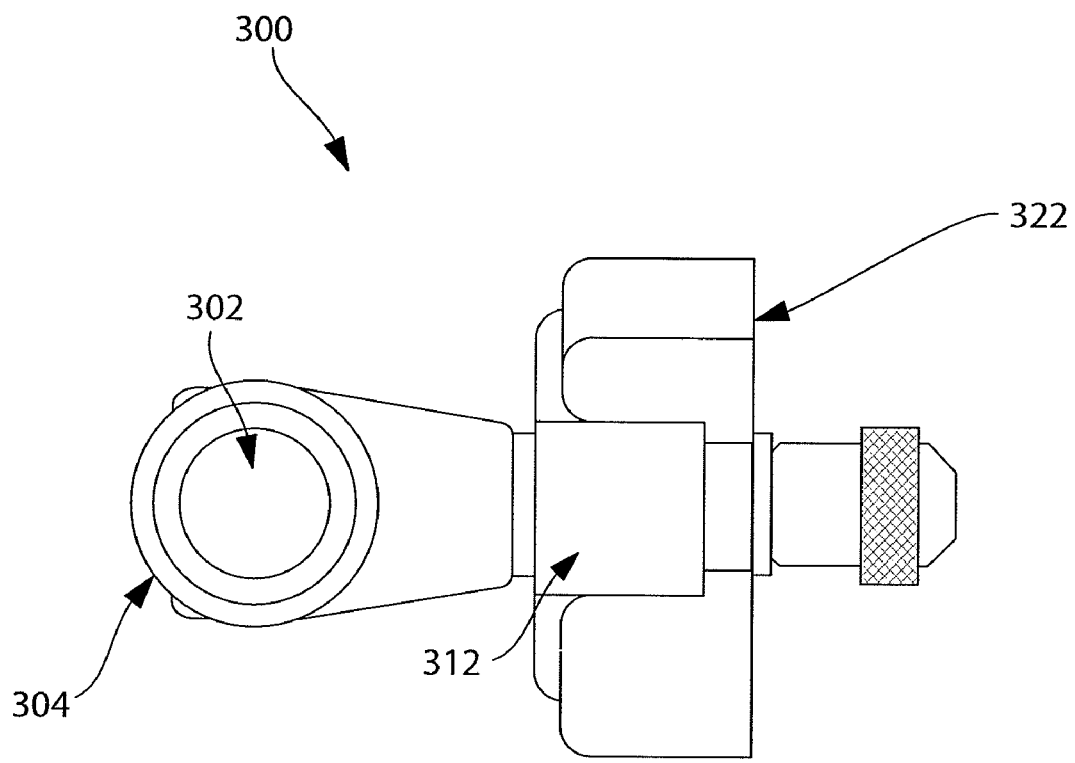
Figure 3G:
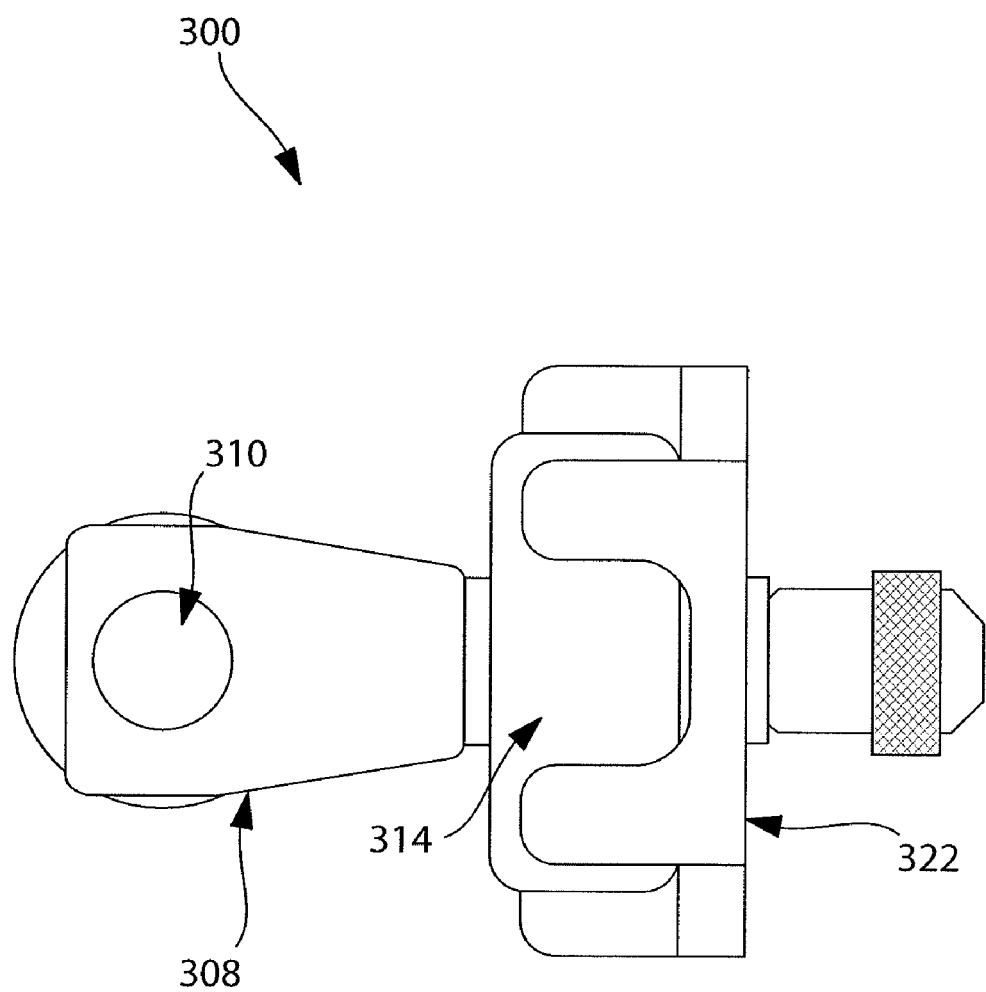
Figure 3H:
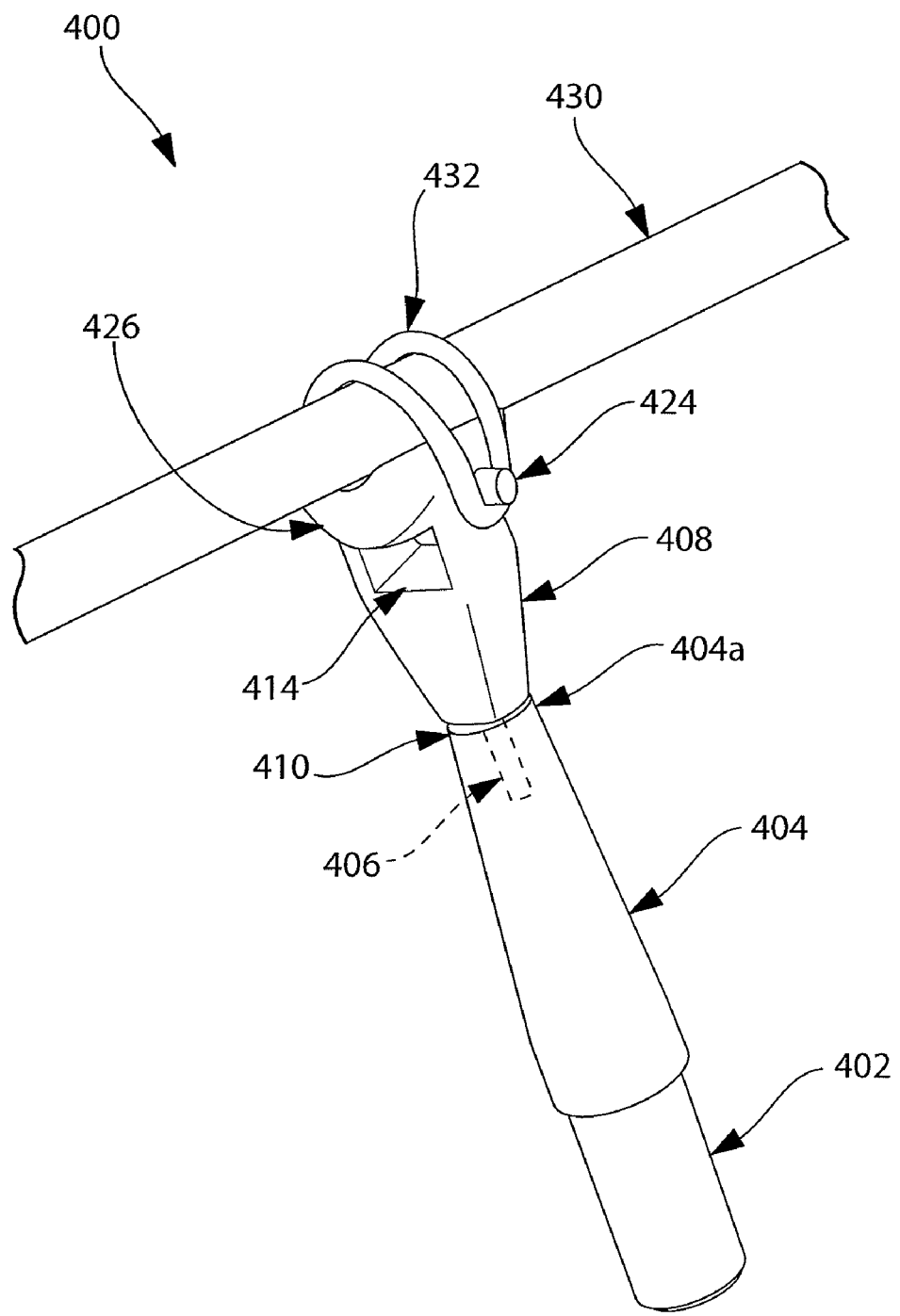
FIGS. 3H-3N show yet another embodiment of a laparoscopic instrument holder according to the present invention, including (3H) a perspective view, (3I) a front view, (3J) a back view, (3K) a first side view, (3L) a second side view, (3M) a bottom view, and (3N) a top view.
Figure 3I:
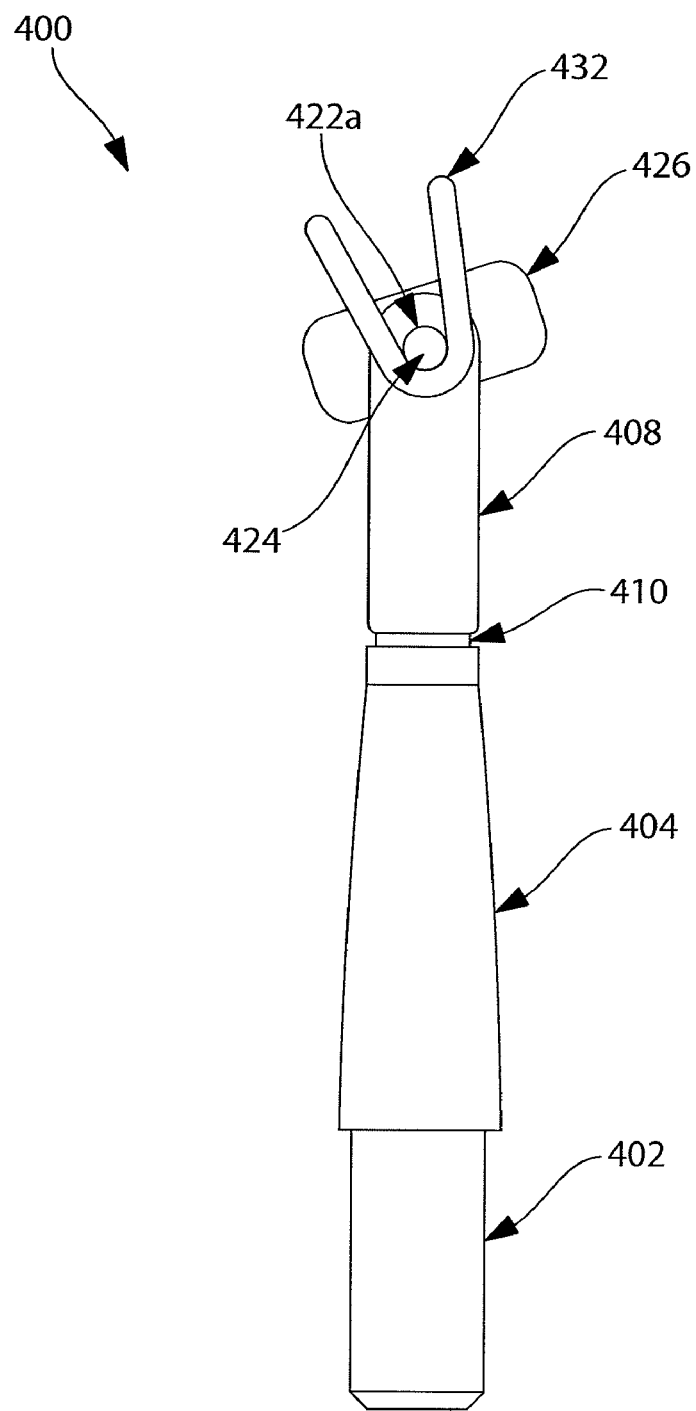
Figure 3J:
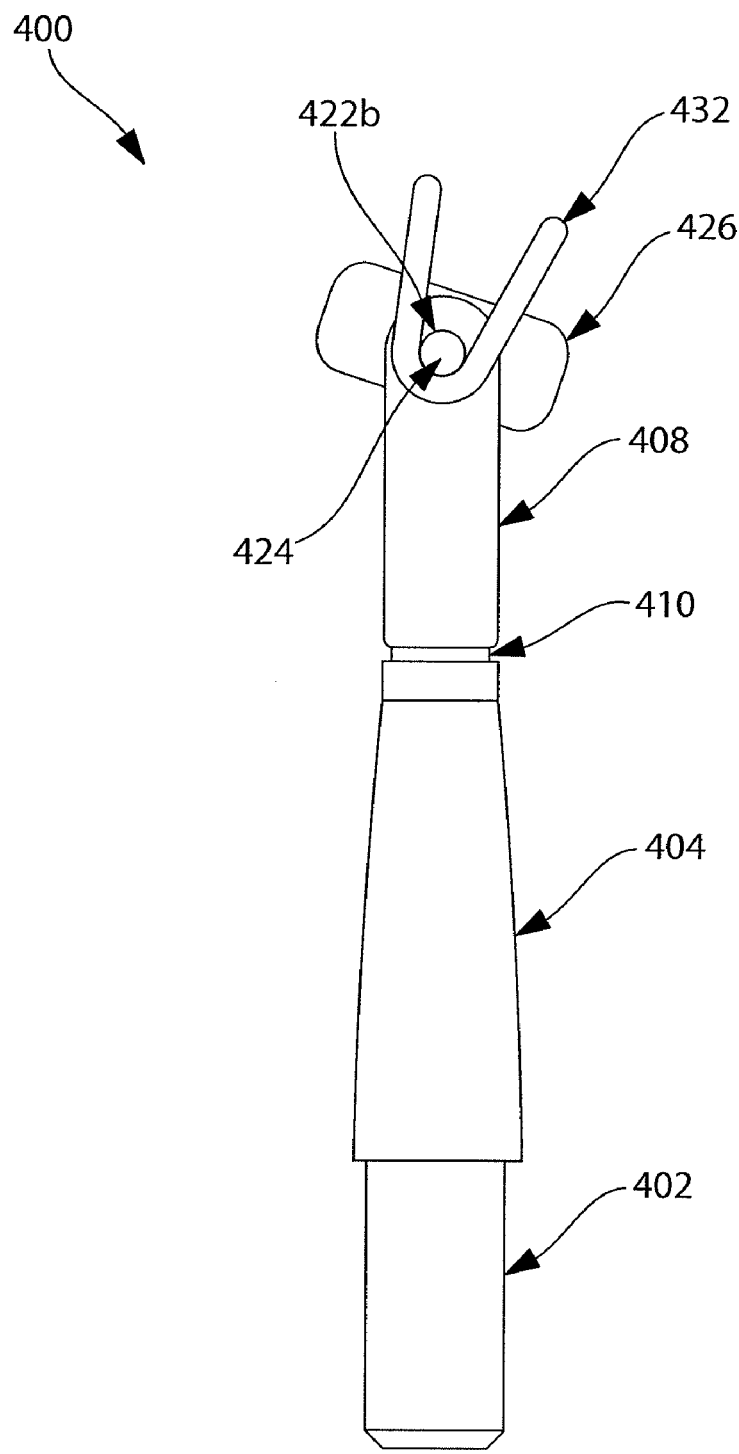
Figure 3K:
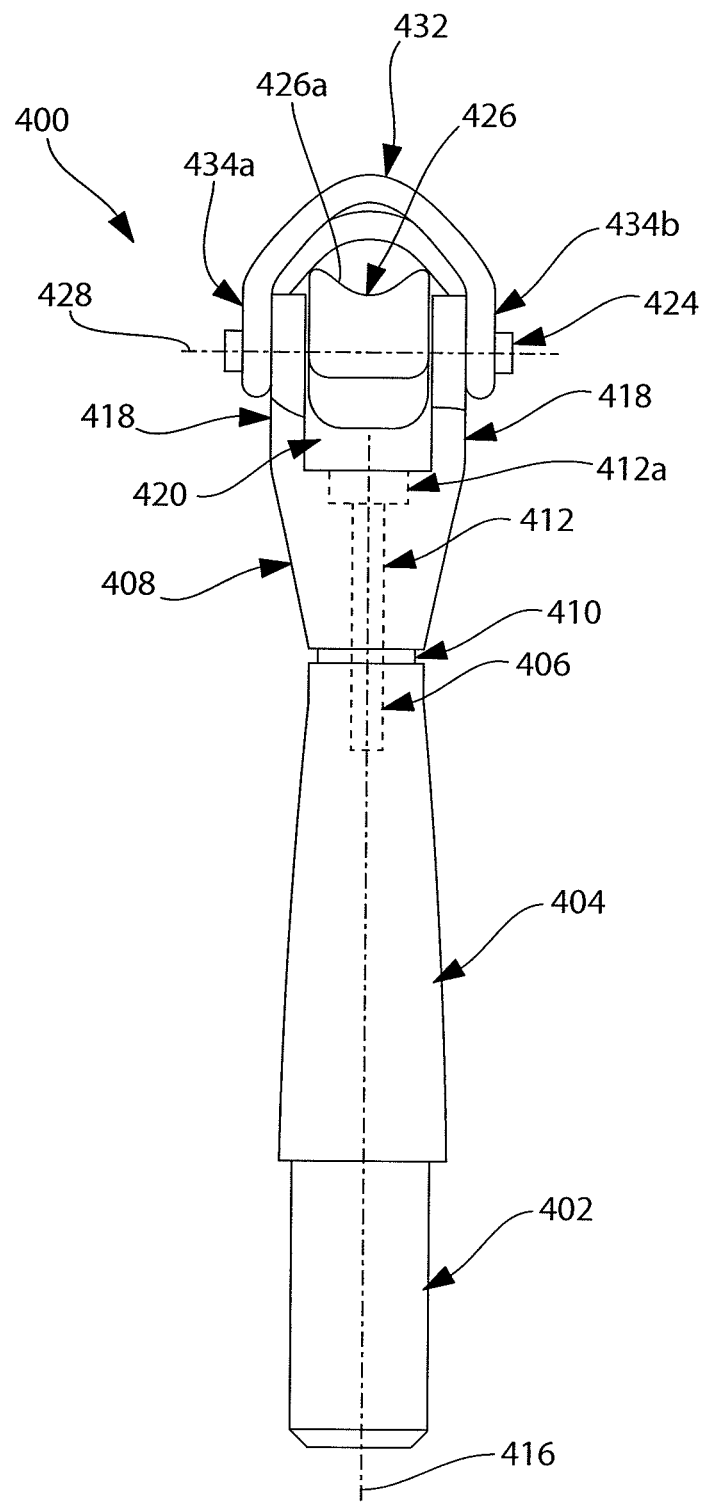
Figure 3L:
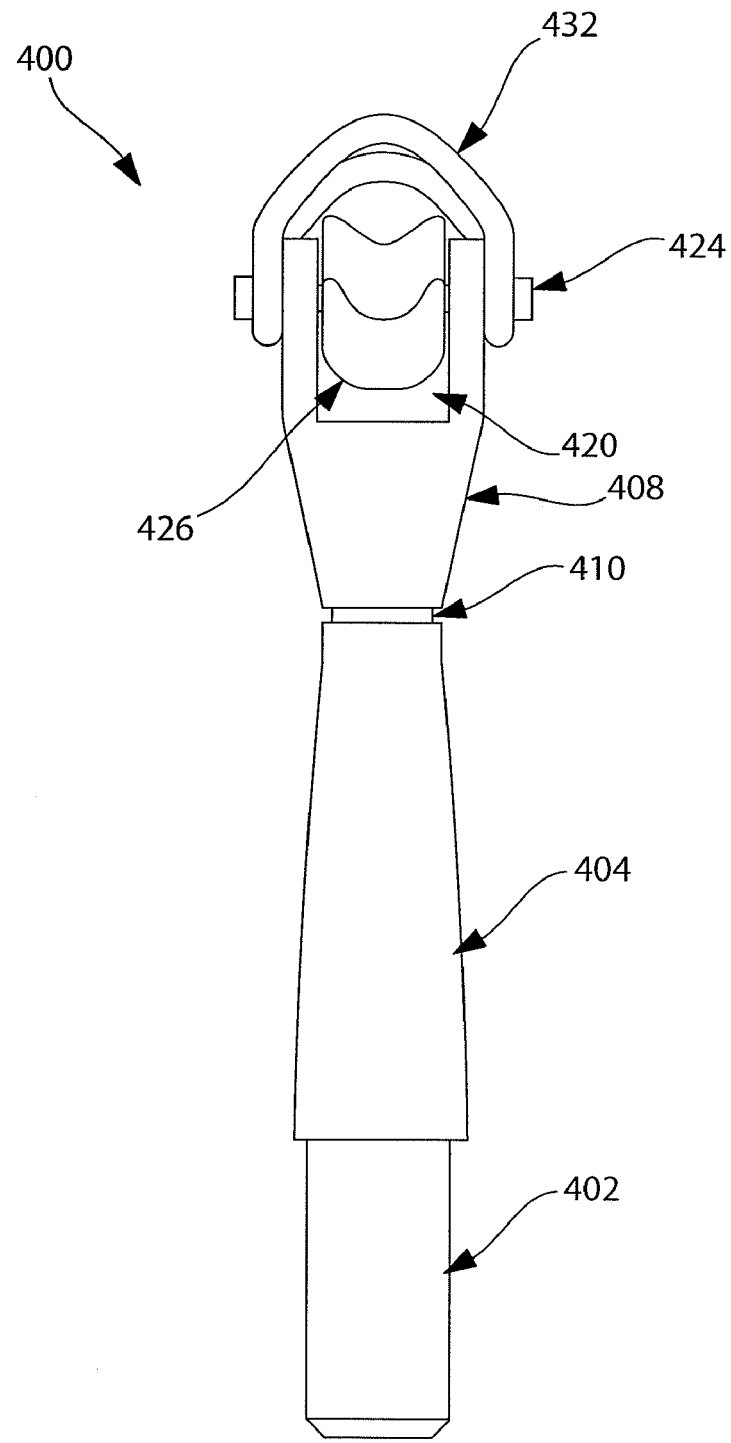
Figure 3M:
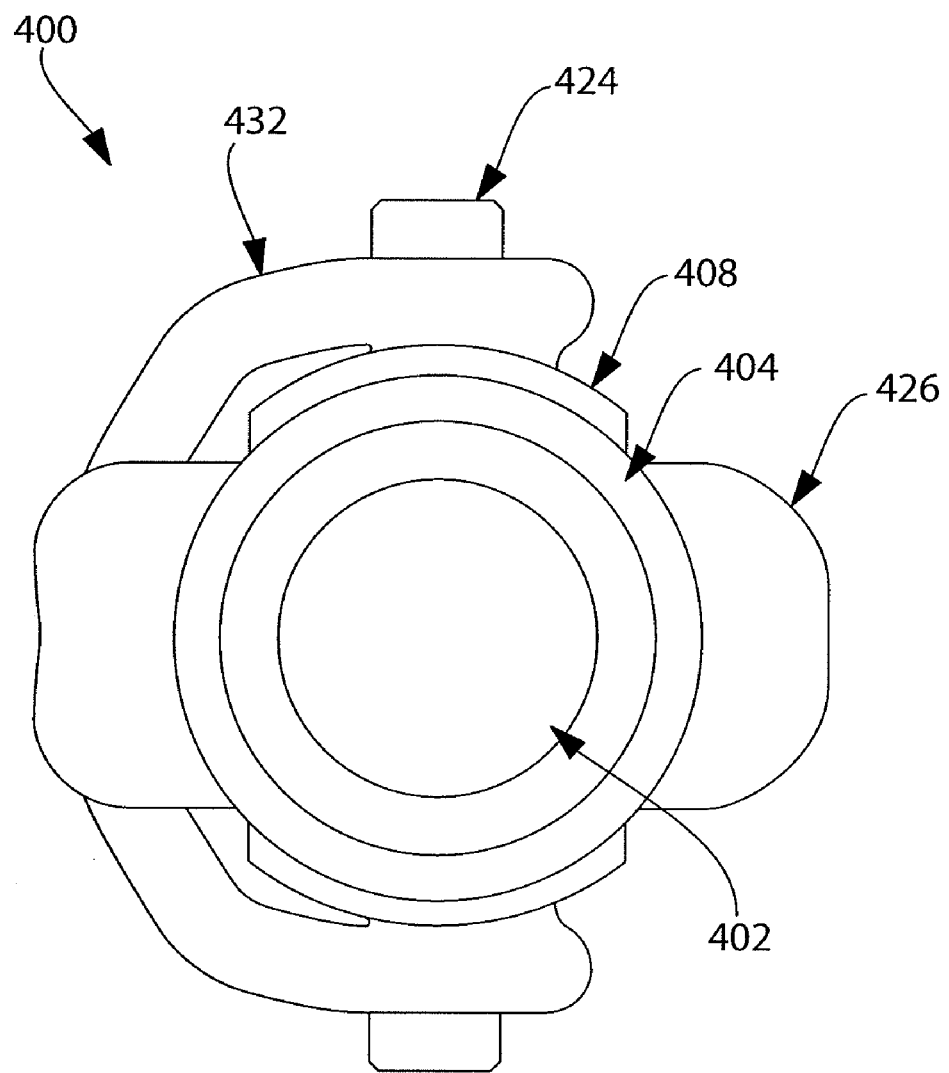
Figure 3N:
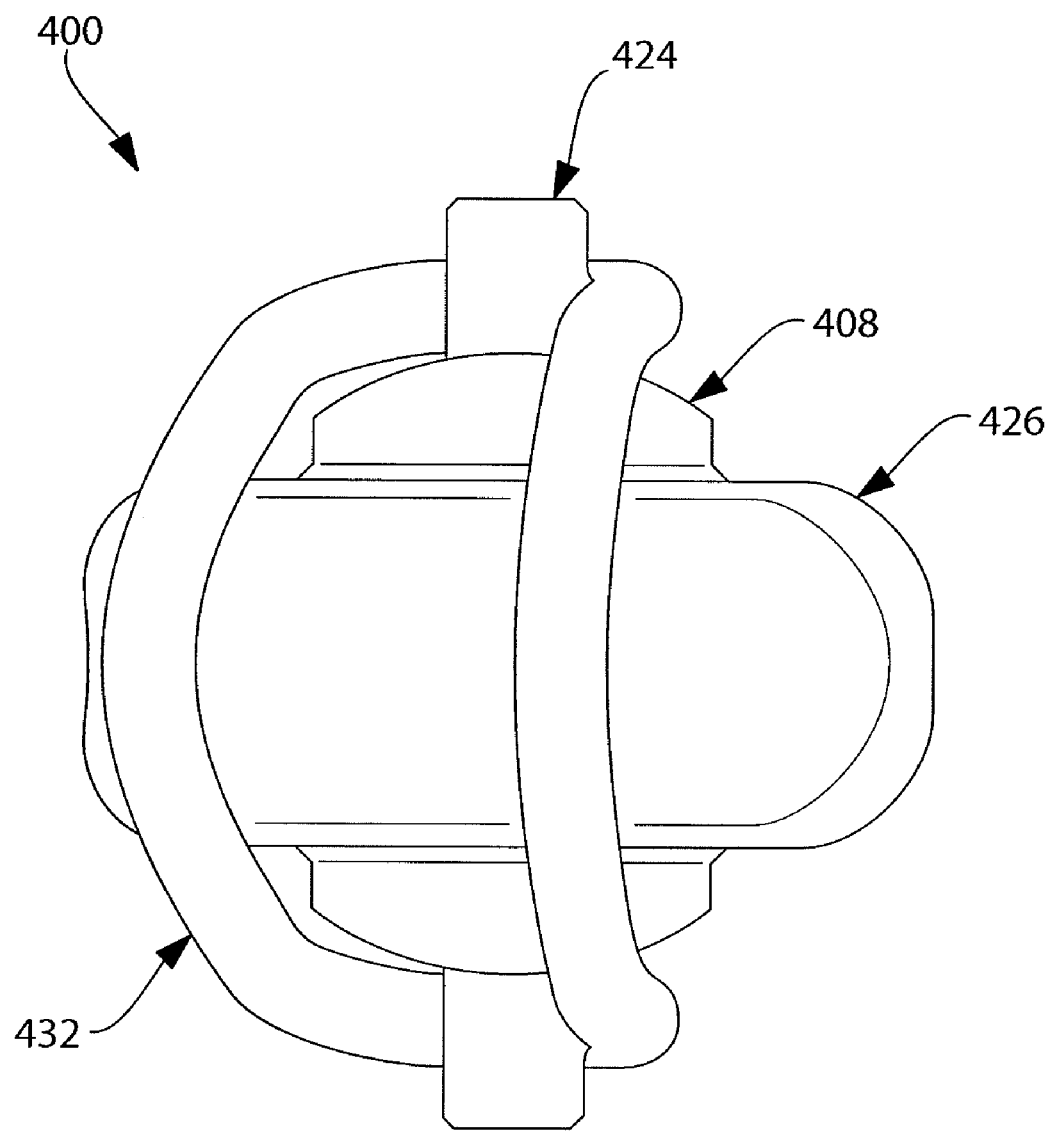

Angulation of first clamping portion 426 on member 424 permits a laparoscopic device such as a endoscopic camera, schematically shown in FIG. 3I1 as component 430, to be selectively positioned by a surgeon in a desired orientation.

Finally, a second clamping portion 432 is provided. Portion 432 preferably is elastic, and in one preferred exemplary embodiment is a resilient rubber o-ring. Advantageously, member 424 extends outward from extensions 418 such that a clamping portion 432 in the form of an o-ring may be demountably coupled proximate ends thereof. Member 424 may include a head or lip at each free end thereof to further assist in captivating clamping portion 432. Thus, a component 430 may be releasably secured to holder 400 by: resting component 430 against first clamping portion 426 on surface 426a, coupling a first loop section 434a of second clamping portion 432 to member 424, extending second clamping portion 432 over component 430, and coupling a second loop section 434b of second clamping portion 432 to member 424.

Although a resilient o-ring is shown, other alternate embodiments include for example a flexible clip.

Figure 30:
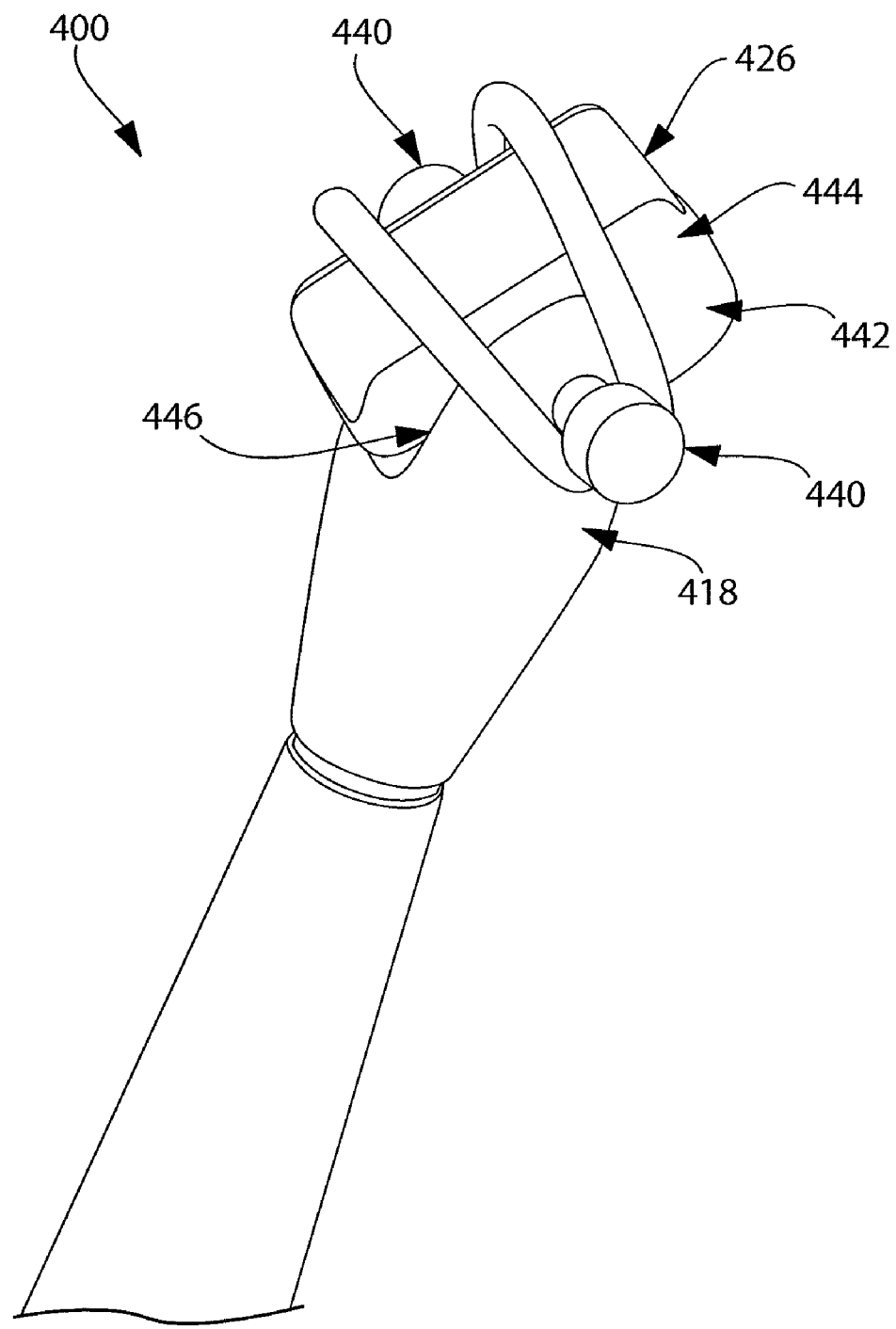

An alternate embodiment of holder 400 is shown in FIG. 30. In this embodiment, member 424 comprises a pair of opposing, aligned set screws 440. Thus, clamping portion 426 swivels on an axis defined by screws 440, with the screws extending in holes in clamping portion 426. In addition, clamping portion 426 further includes a recessed portion 442 and a raised portion 444 separated by arcuate transition 446 on the outer sides of each extension 418. Movement of clamping portion 426, in some embodiments, may in part be guided by transition 446, which also may provide a stop to prevent over-rotation of clamping portion 426 on member 440 but otherwise permits free and loose movement.

Figure 3Q:
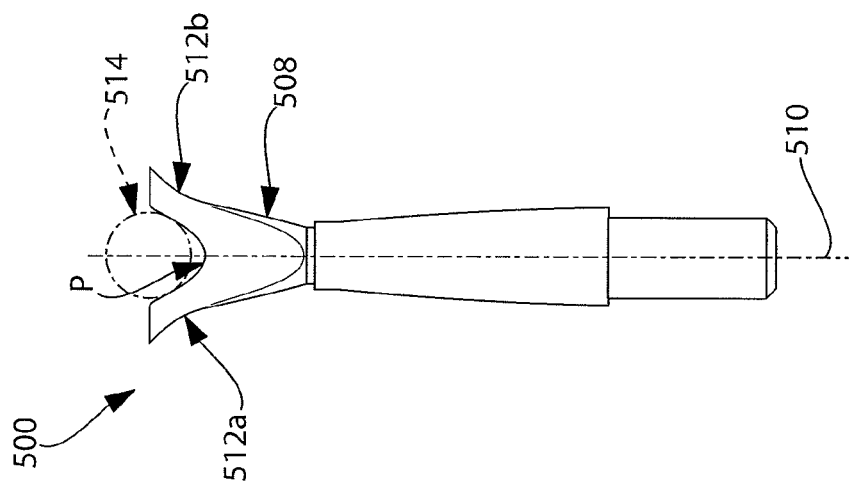
FIGS. 3P-3Q show another embodiment of a laparoscopic instrument holder according to the present invention, including (3P) a perspective view and (3Q) a front view.
Figure 3P:
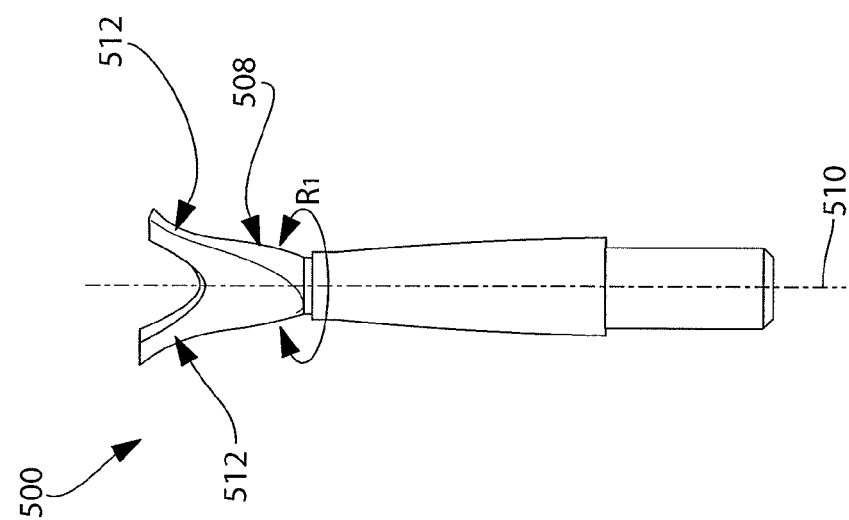

Another embodiment of a holder 500 is shown in FIG. 3P. Holder 500 is similar to holder 400 with the rotatable body, however a one-piece Y-shaped cradle or yoke 508 is provided for use with an elastic clamping band as described above. Rotation is permitted about axis 510 as indicated by $R_1$, and additional rotation is permitted about pivot region P disposed proximate axis 510 at and proximate the center of yoke 512. In particular, an object such as an endoscopic camera 514 my rock transverse to axis 510, for example in a plane through axis 510 and extending into and out of the page. As shown for example in FIG. 3K, an elastic band may be retained proximate regions 512a, 512b, extending over object 514. In the preferred exemplary embodiment, tines 512 are rigid. However, in some alternate embodiments, tines 512 may have limited flexibility in positioning. In particular, a laparoscopic device such as an endoscopic camera could be held in the Y-axis using the elastic band.

Figure 3S:
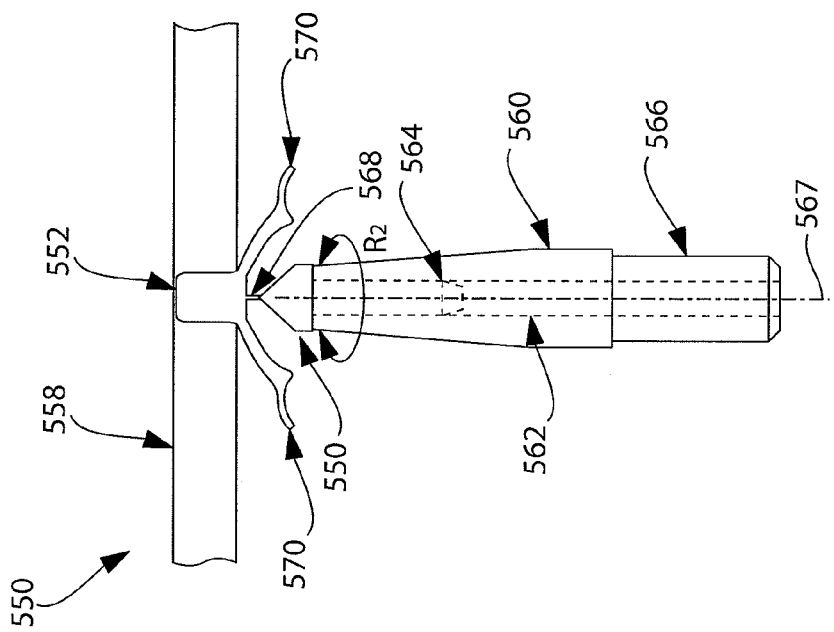
FIG. 3S shows a partial cross-sectional side view of the clamping system of FIG. 3Q.
Figure 3R:
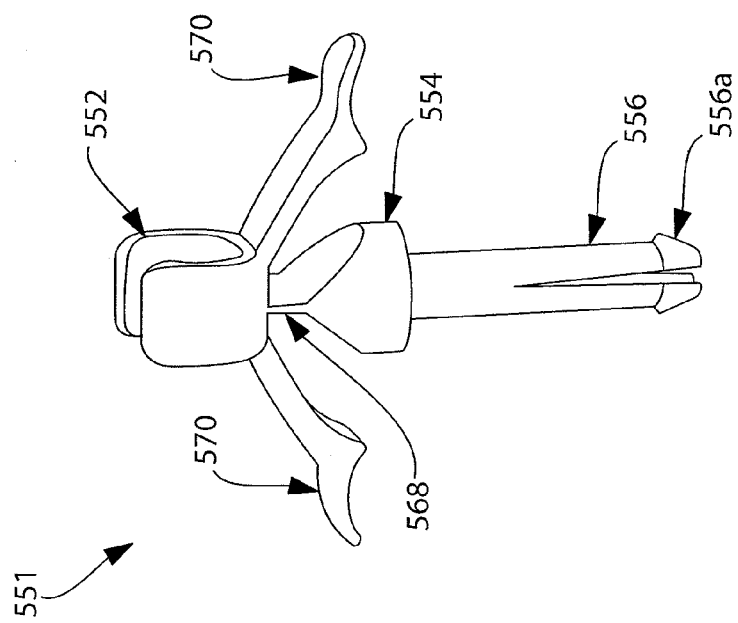
FIG. 3R shows a perspective view of a portion of another clamping system for use with the present invention.

In yet another embodiment, shown in FIGS. 3R-3S, a holder system 550 includes a holder 551 with a clamping portion 552 for receiving a laparoscopic device such as an endoscopic camera (shown schematically as object 558). Clamping portion 552 is mounted at one end of a body 554 with a split shaft 556. Holder 551 is formed of unitary construction, and for example could be mounted on body portion 560 having a preferably unthreaded hole 562. In particular, split shaft 556 may be releasably disposed in hole 562 so that body 554 and clamping portion 552 may rotate with respect to body portion 560. Portion 556a may be used to engage a suitably configured region in hole 562 (such as a ledge 564) to releasably lock clamping system 550 in hole 562. A coupling portion 566 in the form of a post may be provided as previously described with respect to other embodiments. Body 554 may rotate about central axis 567 in direction R2 as shown. In addition, further rotation may be provided by preferably rigid member 568 extending from body 554 to clamping portion 552. Member 568 forms a living hinge and permits rotation in the form of rocking transverse to axis 567 and preferably in the plane of the page for the orientation shown in FIG. 3S. In a preferred exemplary embodiment, member 568 is rigid such that torsion about axis 567 is substantially resisted. Arms 570 serve as levers upon which a user may grasp with his or her fingers to assist in stabilizing the assembly during insertion or withdrawal of an object 558 such as an endoscopic camera from clamping portion 552.

Portions of the holders described above, such as holder 551, for example, could be made injection molded parts that could be made to function as described. Holder 551, for example, may be a single-use, sterile, disposable component and thus in some embodiments a sterile drape for use with system 550 need only cover body portion 560 thereof and not holder 551.

Referring next to FIGS. 4A-4E, another exemplary embodiment of a laparoscopic instrument holder 800 according to the present invention is shown. Holder 800 includes a coupling portion 802 in the form of a post that optionally may include a circumferential groove therein (not shown). Coupling portion 802 preferably is configured to be received in portion 82 of free handle 62 of articulating arm assembly 14, as will be described later. Holder 800 includes a body portion 804 coupled along axis 806 at a first rotational joint 808 to a first joint member 810. In the exemplary embodiment, first rotational joint 808 may permit a 360° range of rotation about axis 806.

In some embodiments, a series of rotational joints may be provided. In the exemplary embodiment, first member 810 is coupled along an axis 812 at a second rotational joint 814 to a second joint member 816. Second rotational joint 814 may permit a 360° range of rotation about axis 812. Second joint member 816 is coupled along an axis 818 at a third rotational joint 820 to a third joint member 822. Third rotational joint 820 may permit a 360° range of rotation about axis 818.

Holder 800 further includes a linear length adjustment portion 824, which will be described shortly. In the exemplary embodiment, portion 824 is coupled along an axis 826 at a fourth rotational joint 828 to third joint member 822. Preferably, fourth rotational joint 828 is disposed proximate a free end of portion 824.

In one preferred exemplary embodiment, axes 806, 812 are disposed at about 90° with respect to each other, axes 812, 818 are disposed at about 90° with respect to each other, and axes 818, 826 are disposed at about 90° with respect to each other. In addition, the combination of rotational joints 808, 814, 820, 828 permit movement in four separate planes, it being possible for at least one pair of said planes (e.g., as defined by joints 808, 820 or as defined by joints 814, 828) to be parallel to one another and it also being possible for there to be two pairs of parallel planes provided by the joints (e.g., as defined by joints 808, 820 and as defined by joints 814, 828). The combination of rotational joints 808, 814, 820, 828 also preferably permits movement in four separate planes which may be nonparallel to one another.

In the exemplary embodiment, linear length adjustment portion 824 forms a sliding mechanism in which a first sliding member 830 is coupled to a second sliding member 832 and slidably associated with one another. Preferably, constant friction sliding is provided by members 830, 832. Also in the exemplary embodiment, members 830, 832 are restricted to move with respect to one another along central sliding axis 834.

Member 830 for example may be coupled to a coupling portion 836 such as with a plurality of screws 838. Preferably, coupling portion 836 is configured and dimensioned to be received and slide in a grooved portion or track 832a formed in member 832. Members 830, 832 may be coupled to one another with a set screw 839 which extends through and is permitted to translate along the length of slot 840 in member 832. The shaft of set screw 839 extends into member 834. In some embodiments, set screw 839 may be tightened so that the head thereof bears against member 832 to adjust the friction between the members 830, 832 with respect to each other.

In alternate embodiments, the shaft of set screw 839 and the width of slot 840 may be sized so that if no coupling portion 836 is provided, movement of members 830, 832 is guided along axis 834.

Another rotational joint 842 is disposed proximate the free end of portion 824 opposite the free end at which rotational joint 828 is disposed. Joint 842 is disposed along an axis 844. In particular, an extension 830a of member 830 is coupled along axis 844 at rotational joint 842 to a joint member 846.

Rotational joint 842 may permit a 360° range of rotation about axis 844. Preferably, axes 834, 844 are parallel and disposed in different planes.

Joint member 846 is coupled along an axis 848 at yet another rotational joint 850 to a laparoscopic device retaining portion 852. Rotational joint 850 may permit a 360° range of rotation about axis 848. Laparoscopic device retaining portion 852 for example may be a clamp formed by a pair of jaw members 852a, 852b that are spring biased toward one another with a spring 852c at a laparoscopic device grasping region 852c1. Preferably, laparoscopic device grasping region 852d is sized to receive a laparoscopic device such as an endoscopic camera, shown schematically as device 854. Thus, grasping region 852d may be sized, for example, to grasp a 5 mm and/or 10 mm laparoscope. In the exemplary embodiment, axes 844, 848 are disposed at about 90° with respect to each other.

Retaining portion 852 preferably may be used to secure the shaft portion of a laparoscopic device such as an endoscopic camera. A sterile sleeve drape may be used to cover the entire apparatus and to be imbricated into grasping region 852d. Preferably, while spring-biased jaw members are configured to hold the laparoscopic device securely, they also permit the device to be manually rotated about its linear axis with enough frictional resistance to prevent undesired rotational movement.

The rotational joints of holder 800 such as rotational joints 814, 816 for example may be formed as follows. A threaded screw 856 is disposed with the head thereof abutting a first washer 858a which optionally rests on a second washer 858b. Washers 858a, 858b rest on a ledge such as ledge 860 in member 816. The shaft of screw 856 extends through coaxial holes 862, 864 in adjacent components such as members 810, 816, and is threadably received in a nut 866 that rests against a washer 868 abutting ledge 870 in member 810. Members 810, 816 may be separated from one another with a washer 872. A sleeve 874 optionally may be provided with a hole therein through which the shaft of screw 856 extends and is guided. Sleeve 874 may be disposed proximate the head of screw 856 or remote from the head.

Thus, laparoscopic device 854 may be positioned as desired using the combined freedom of movement provided by rotational joints 808, 814, 820, 828, 842, 850, linear length adjustment portion 824, as well as the rotation provided by coupling portion 802 when received in portion 82 of free handle 62 of articulating arm assembly 14.

In one preferred exemplary embodiment, holder 800 moves with five degrees of freedom, with the sixth degree being accommodated by rotation of laparoscopic device 854 within laparoscopic device retaining portion 852. Preferably, frictional movement is provided by rotational joints 808, 814, 820, 828, 842, 850, linear length adjustment portion 824, as well as coupling portion 802 when received in portion 82 of free handle 62 of articulating arm assembly 14. Preferably, the friction is sufficient to hold the laparoscopic device regardless of orientation but selected so that the device is easily movable for reorientation through manual manipulation by a user. Higher frictional resistance to allow for movement of the working envelope may be provided by curvilinear articulating arm assembly 12, as described herein. It should be noted, however, that the ease of movement between relatively moving components may be selected as desired as a function of the friction between said components. Thus, different embodiments of holder 800 may be provided with different amounts of friction for rotational joints 808, 814, 820, 828, 842, 850, linear length adjustment portion 824, as well as coupling portion 802.

Figure 4A:
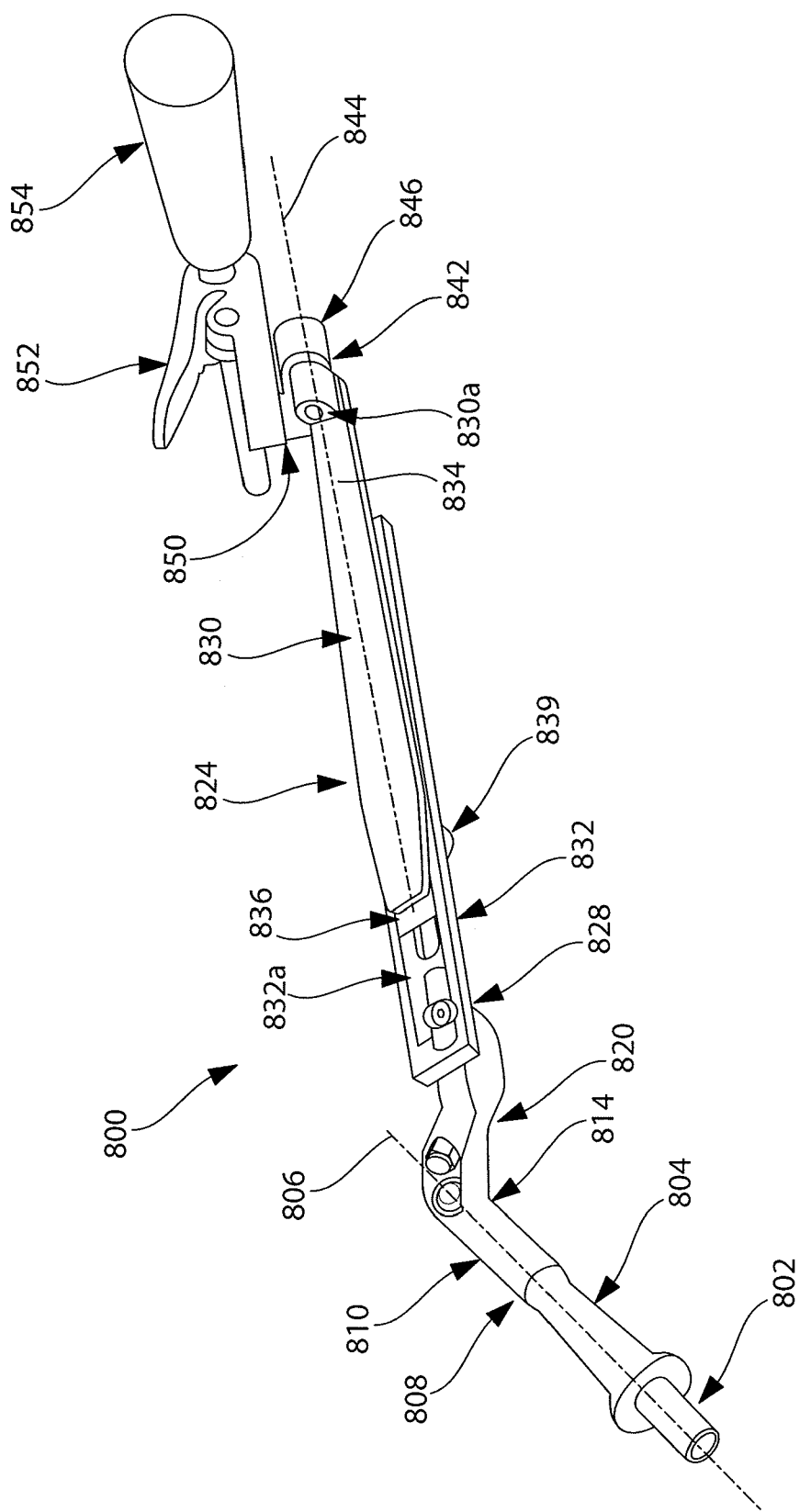
FIGS. 4A-4E show another embodiment of a laparoscopic instrument holder according to the present invention, including (4A) a perspective view with a laparoscopic instrument retained by said holder, (4B) a partial perspective view, (4C) a partial cross-sectional perspective view, (4D) another perspective view, and (4E) another partial cross-sectional perspective view.
Figure 4B:
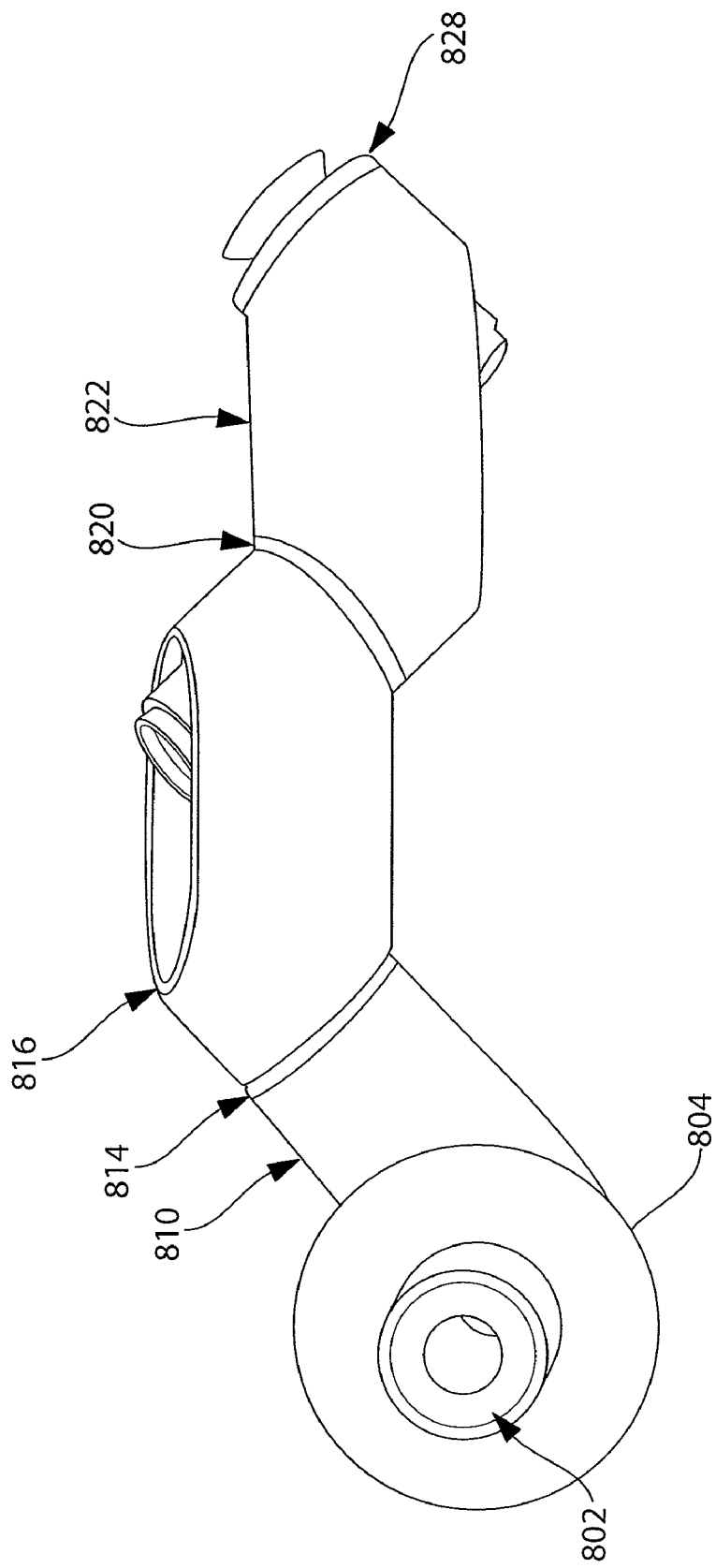
Figure 4C:
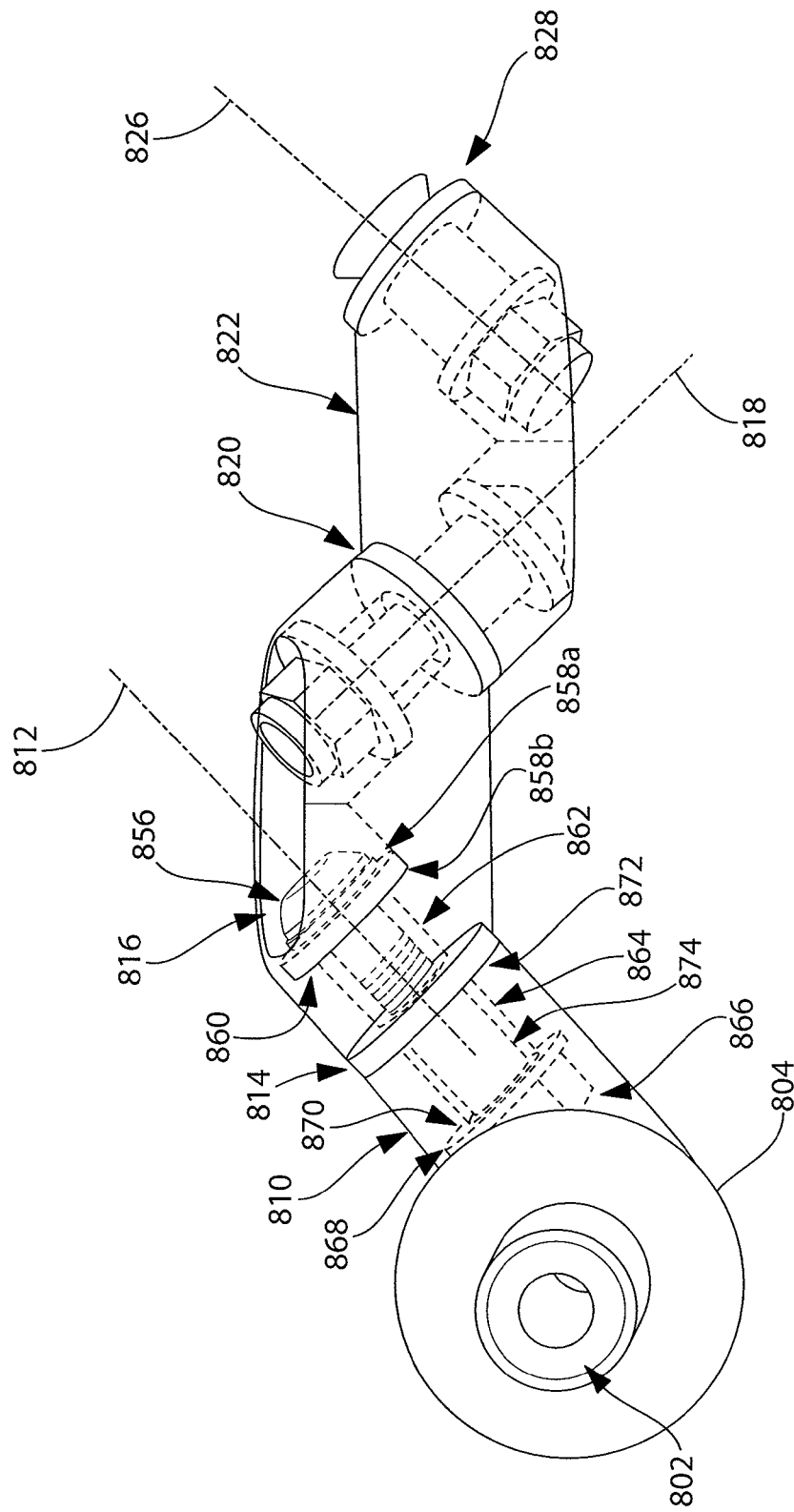
Figure 4D:
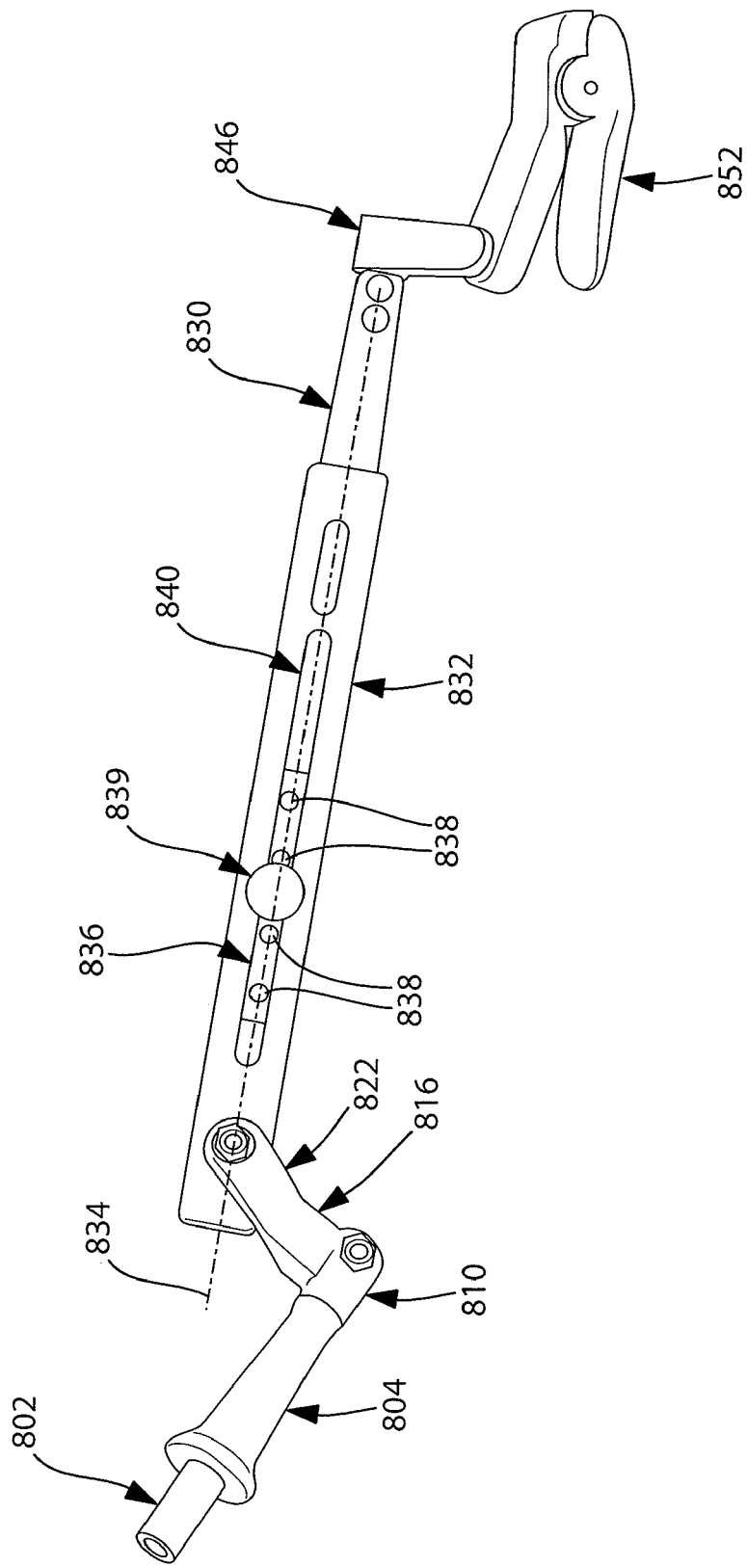
Figure 4E:
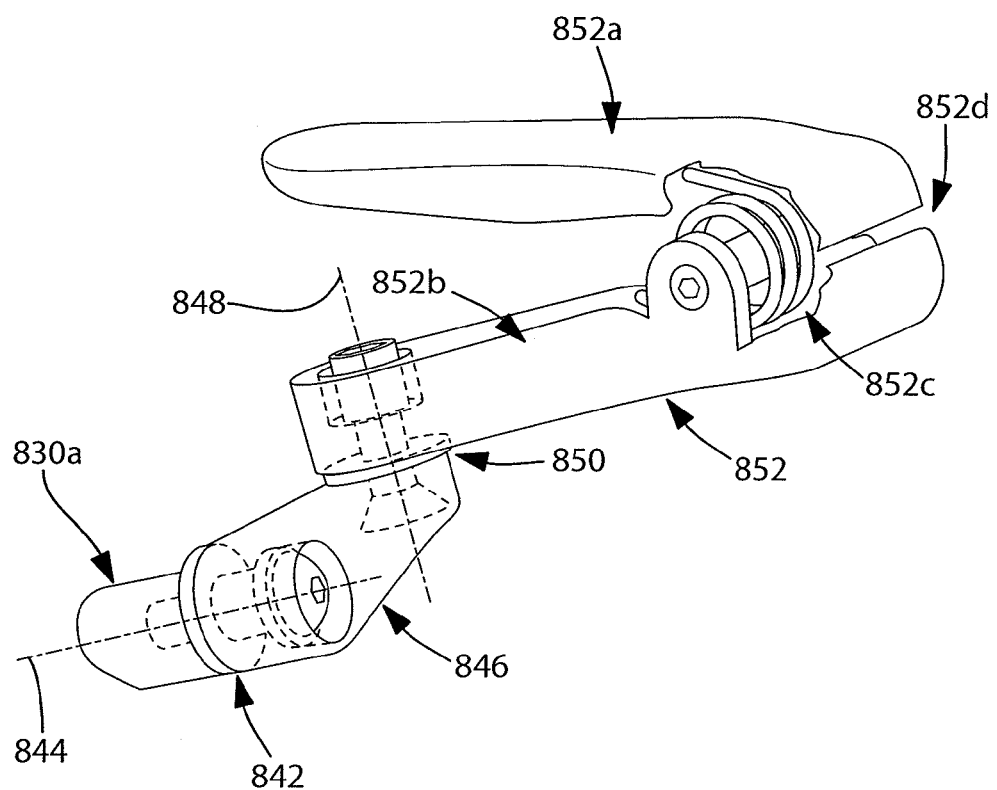
Figure 4F:
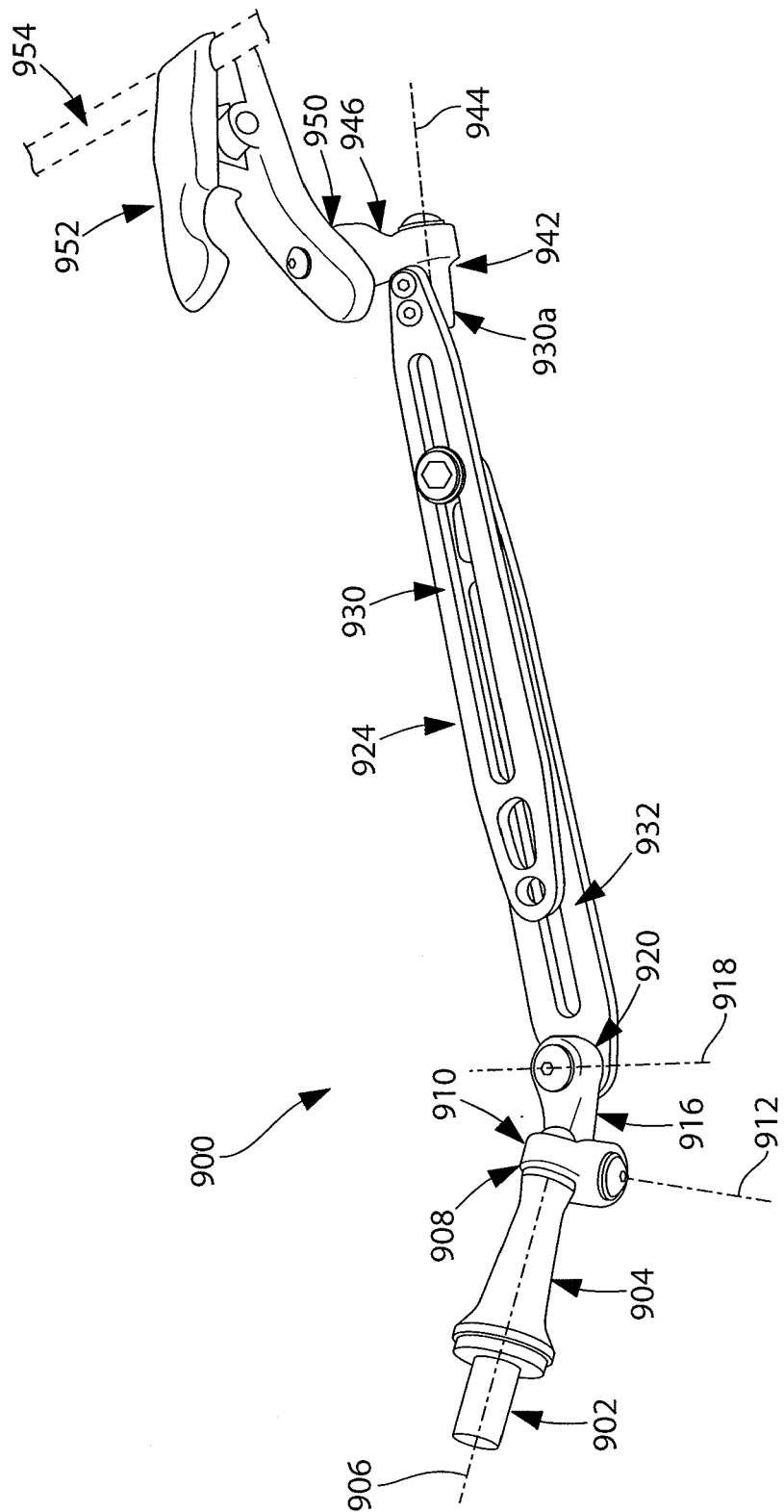
FIGS. 4F-4U show another embodiment of a laparoscopic instrument holder according to the present invention, including (4F) a perspective view with a laparoscopic instrument retained by said holder, (4G) a partial perspective view including several rotational joints, (4H) a partial cross-sectional perspective view including the rotational joints of the previous figure, (4I) another partial perspective view including the rotational joints of the previous figure, (4J) a partial bottom view of the linear length adjustment portion of the holder, (4K) a partial top view thereof, and (4L) a partial cross-sectional side view thereof, (4M) a partial cross-sectional side view of a coupling assembly, (4N) a partial perspective view of several rotational joints, (4O) another partial cross-sectional perspective view of several rotational joints and clamp, (4P) a side view of a clamp, (4Q) another side view of the clamp, and (4R to 4U) partial perspective views of the clamp.
Figure 4G:
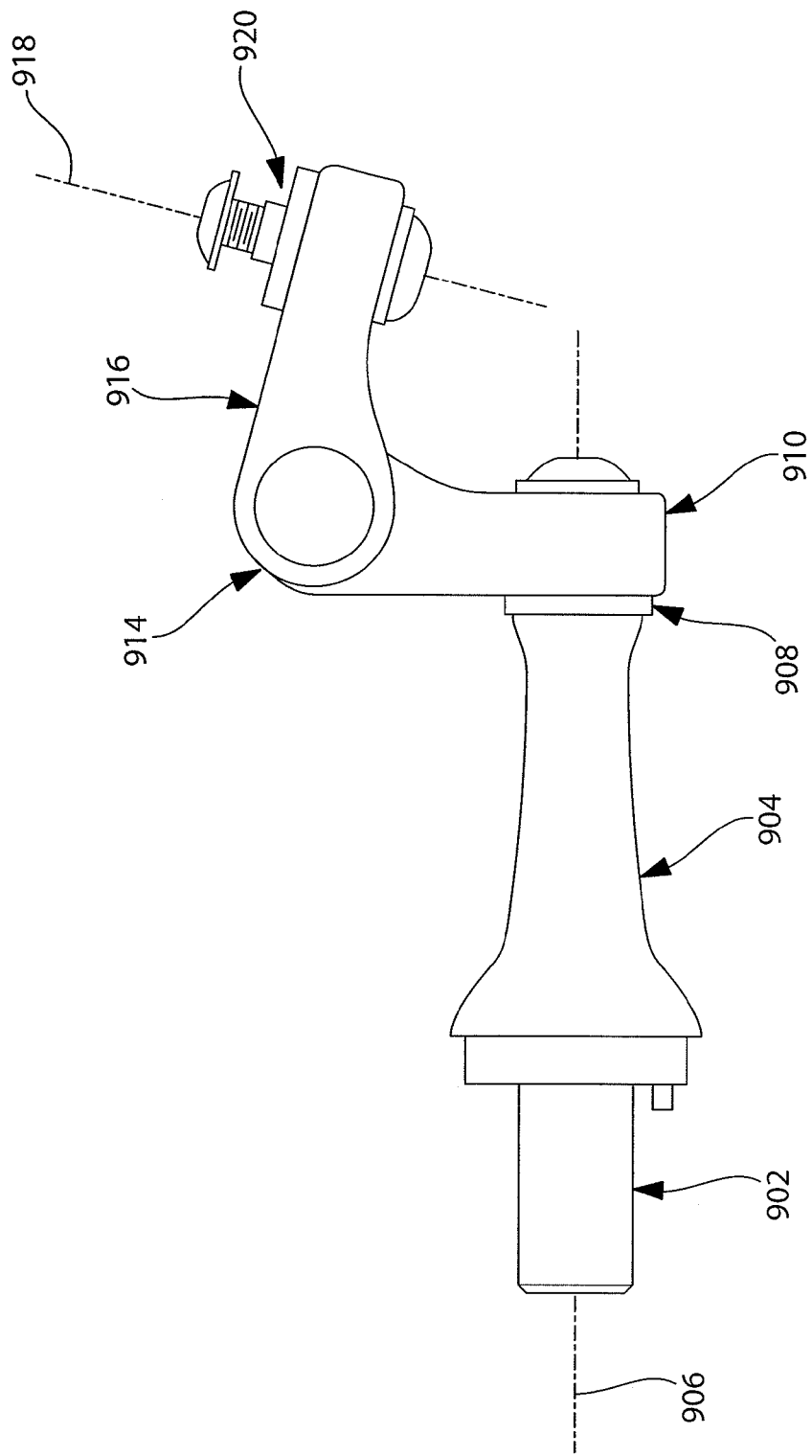
FIGS. 4V-4W show an embodiment of a rotational joint for use with laparoscopic instrument holders of the present invention, including (4V) a partial side view and (4W) a partial cross-sectional side view.
FIGS. 4X-4Z show another exemplary embodiment of a coupling portion for use with laparoscopic instrument holders of the present invention, including (4X) a first side view, (4Y) a second side view, and (4Z) a partial cross-sectional perspective view.
Figure 4H:
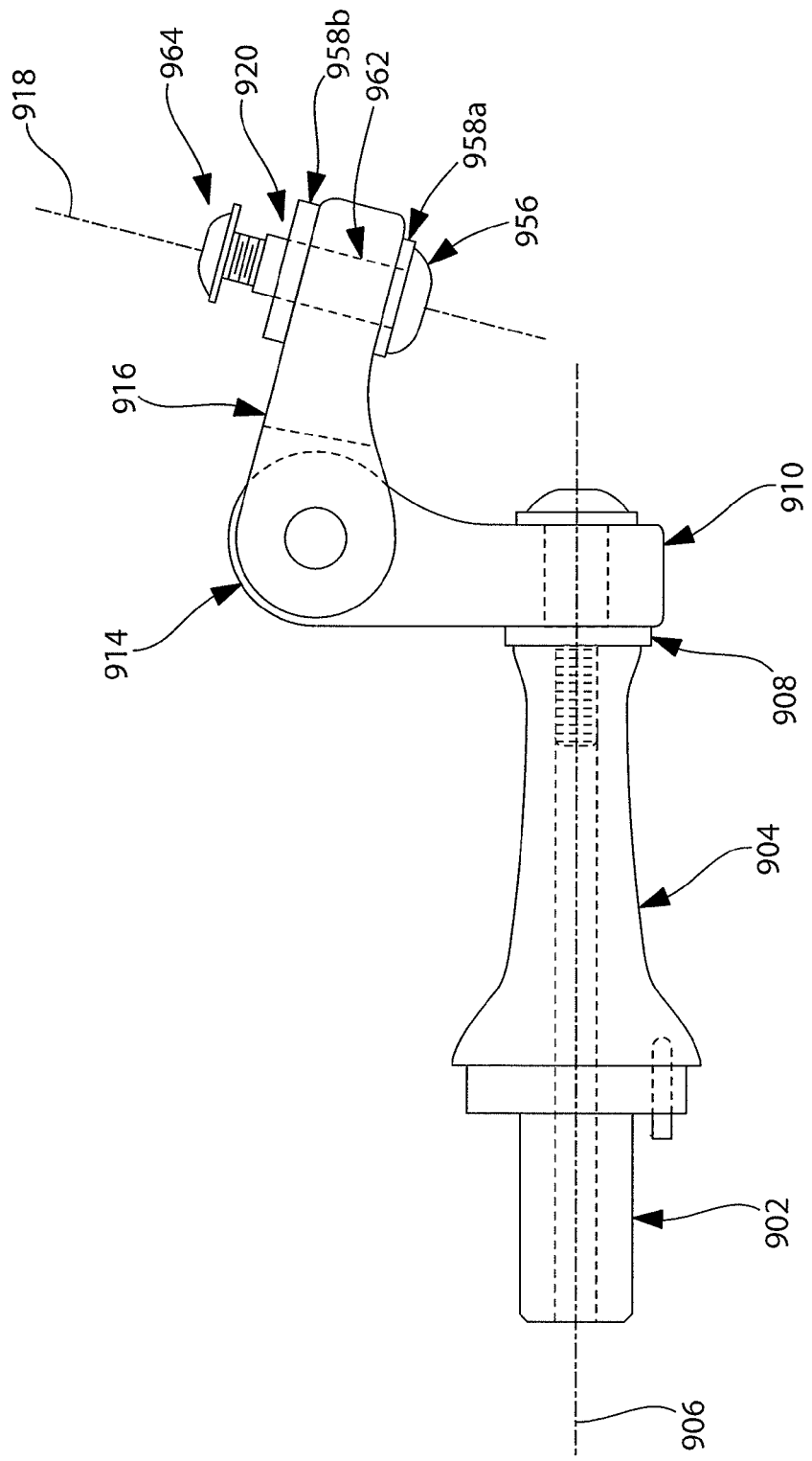
Figure 4I:
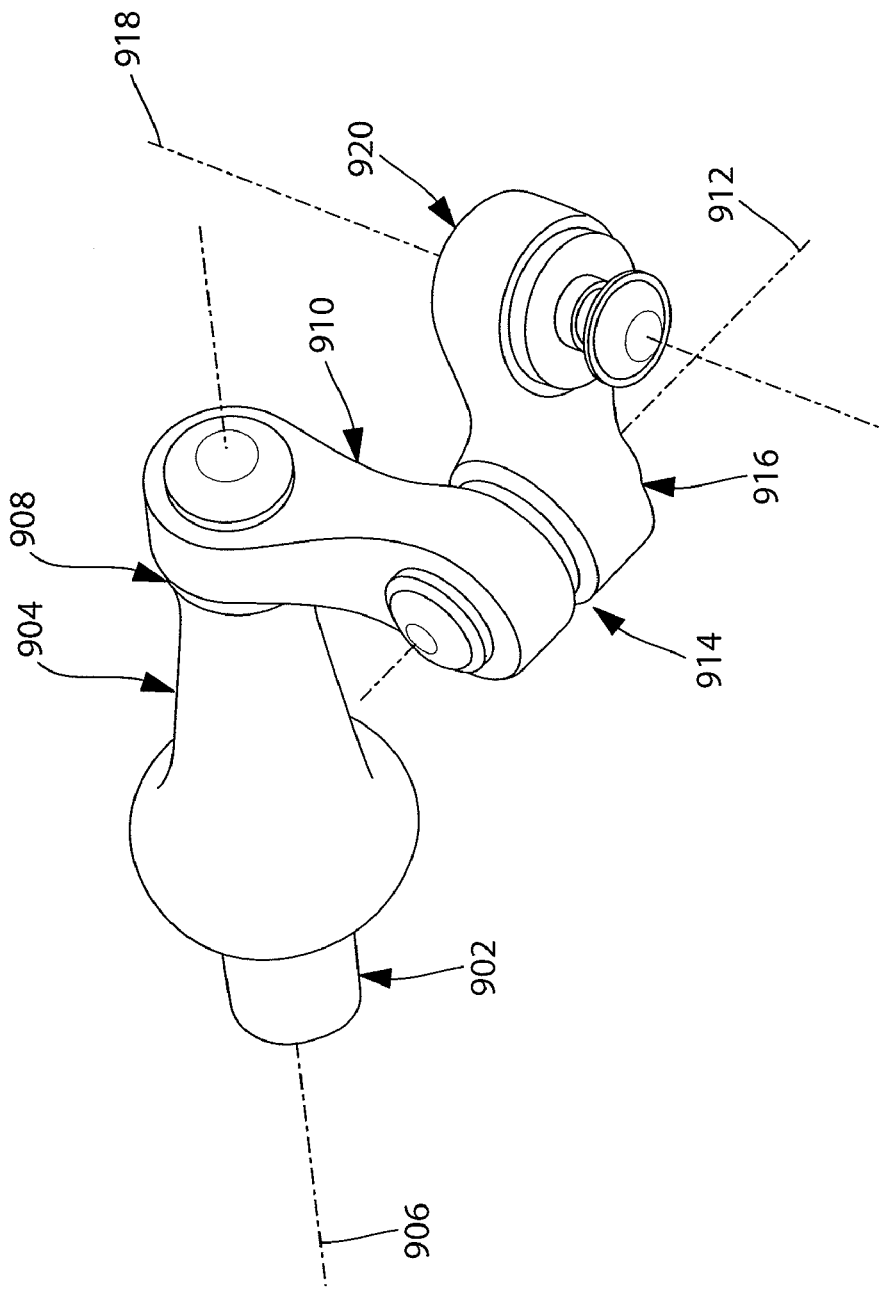
Figure 4J:
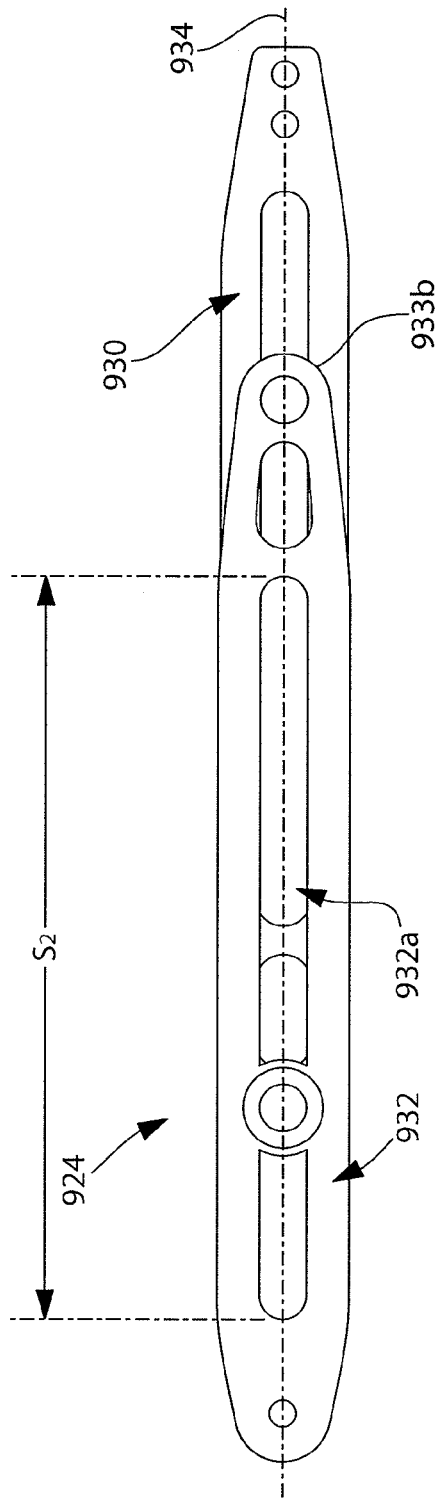
Figure 4K:
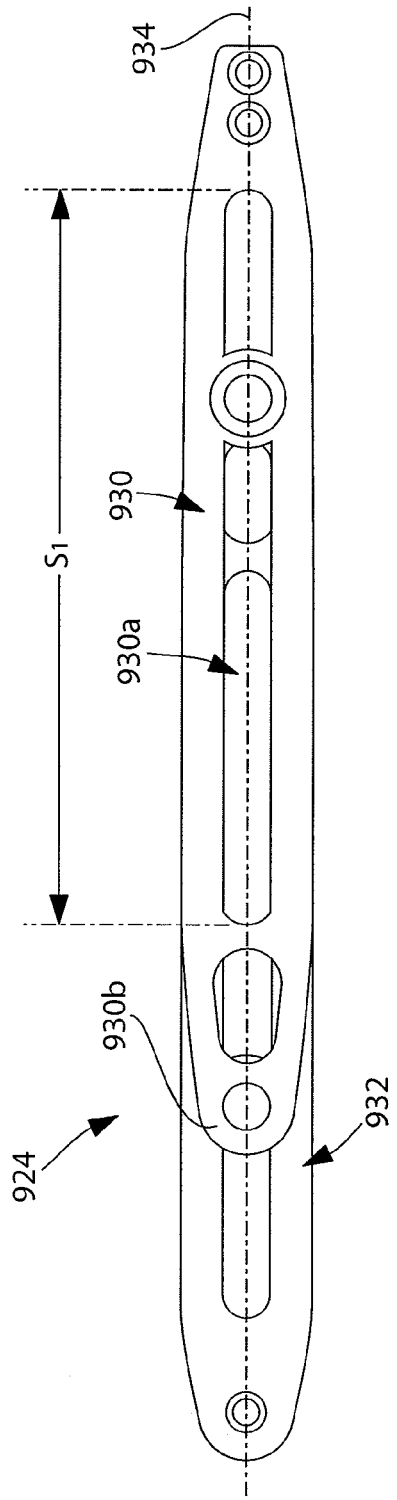
Figure 4L:
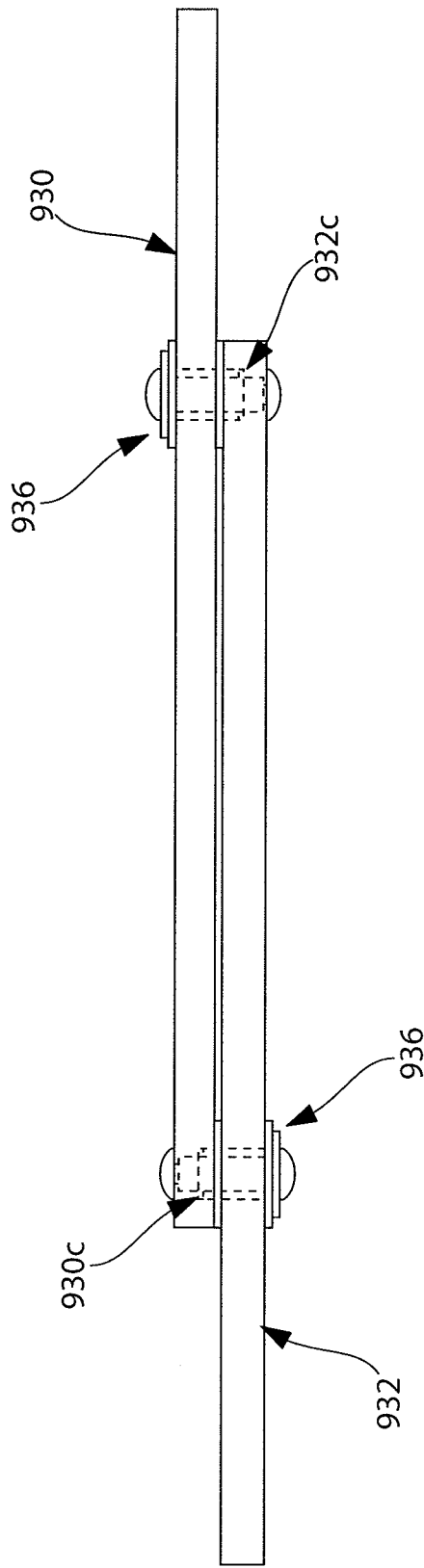
Figure 4M:
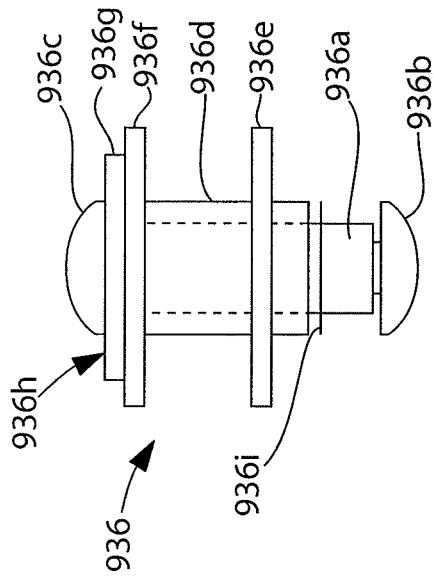
Figure 4N:
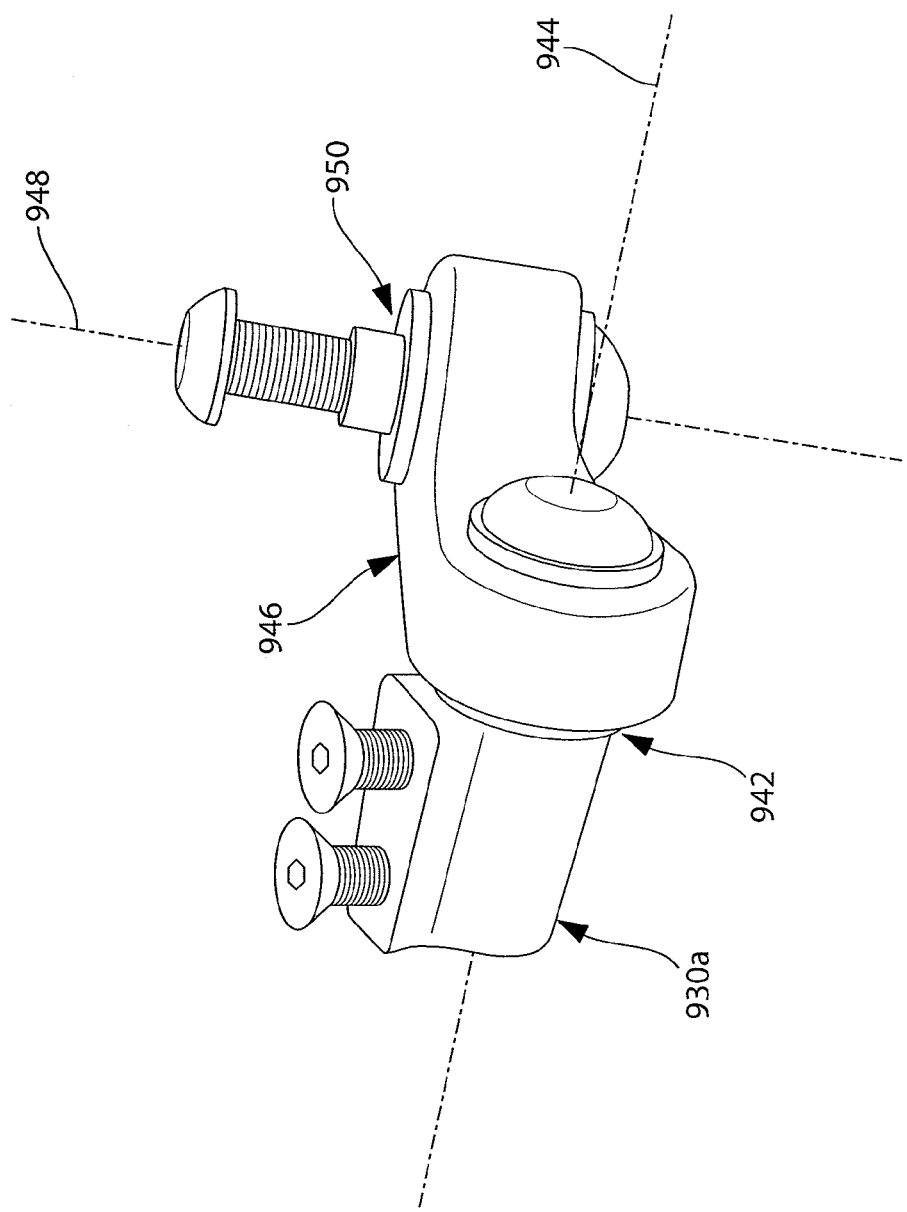
Figure 4T:
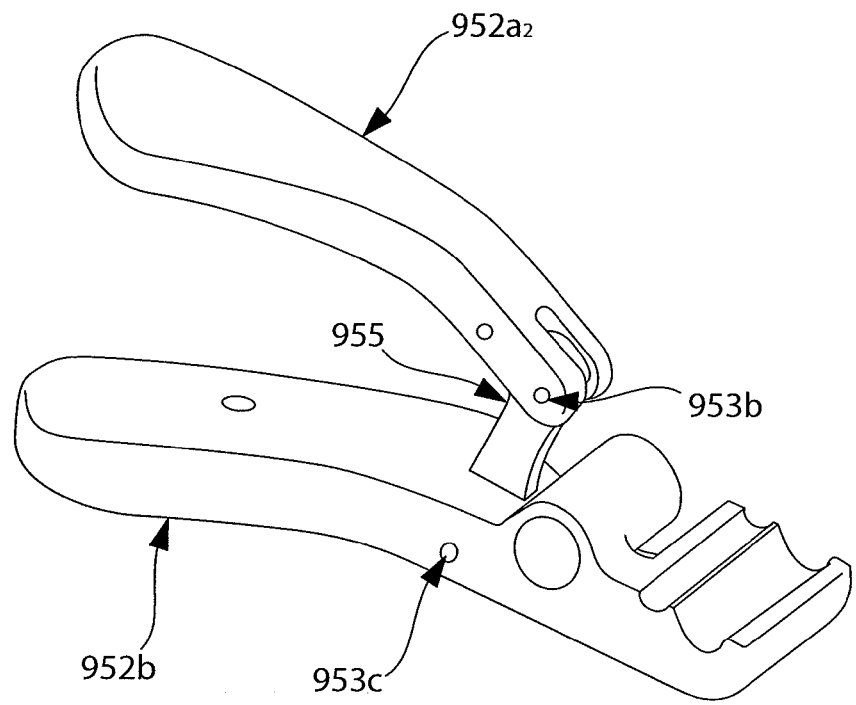
Figure 4U:
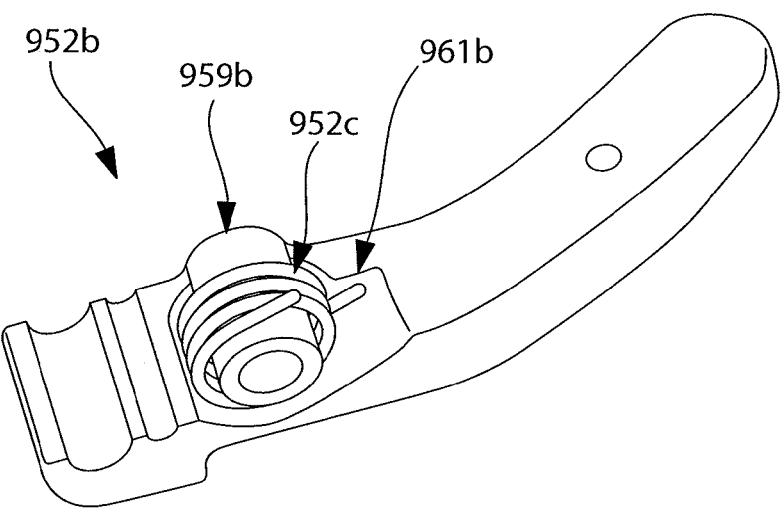

Turning next to FIGS. 4F-4U, yet another exemplary embodiment of a laparoscopic instrument holder 900 according to the present invention is shown. Holder 900 includes a coupling portion 902 in the form of a post that optionally may include a circumferential groove therein (not shown). Coupling portion 902 preferably is configured to be received in portion 82 of free handle 62 of articulating arm assembly 14, as will be described later. Holder 900 includes a body portion 904 coupled along axis 906 at a first rotational joint 908 to a first joint member 910. In the exemplary embodiment, first rotational joint 908 may permit a 360° range of rotation about axis 906.

In some embodiments, a series of rotational joints may be provided. In the exemplary embodiment, first member 910 is coupled along an axis 912 at a second rotational joint 914 to a second joint member 916. Second rotational joint 914 may permit a 360° range of rotation about axis 912. Second joint member 916 is coupled along an axis 918 at a third rotational joint 920 to a linear length adjustment portion 924, which will be described shortly. Third rotational joint 920 may permit a 360° range of rotation about axis 918. Preferably, third rotational joint 914 is disposed proximate a free end of portion 924.

In one preferred exemplary embodiment, axes 906, 912 are disposed at about 90° with respect to each other, and axes 912, 918 are disposed at about 90° with respect to each other. In addition, the combination of rotational joints 908, 914, 920 permits movement in three separate planes, it being possible for at least one pair of said planes (e.g., as defined by joints 908, 920) to be parallel to one another. The combination of rotational joints 908, 914, 920 also preferably permits movement in three separate planes which may be nonparallel to one another.

In the exemplary embodiment, linear length adjustment portion 924 forms a sliding mechanism in which a first sliding member 930 is coupled to a second sliding member 932 and slidably associated with one another. Preferably, constant friction sliding is provided by members 930, 932. Also in the exemplary embodiment, members 930, 932 are restricted to move with respect to one another along central sliding axis 934. Advantageously, linear length adjustment portion 924 permits a user to reposition a laparoscopic device 954, for example into and out of an opening in a patient, with gross movement in a linear direction, as compared to angulation. For example, linear length adjustment portion 924 may permit about 6 inches of linear movement of a device 954 held by holder 900.

Member 930 may be provided with a first slot 930a and member 932 may be provided with a second slot 932a, with each of slots 930a, 932a being disposed centrally along axis 934. First and second slots 930a, 932a each may have a length $S_1$, $S_2$, respectively, along axis 934, and lengths $S_1$, $S_2$ may be about the same as one another. In an exemplary preferred embodiment, lengths $S_1$, $S_2$ each may be about 5.5 inches. In the preferred exemplary embodiment, members 930, 932 are coupled to each other by coupling assemblies 936 extending from fixed positions with respect to and proximate free ends 930b, 932b thereof.

Each coupling assembly 936 includes a female threaded round standoff 936a that threadably receives truss head Phillips machine screws 936b, 936c at opposing ends thereof. Standoff 936a extends through a plain bearing 936d which is sized to slide and be guided in a respective slot 930a, 930b generally constrained for movement along axis 934. Bearing 936d extends through a plastic thrust bearing 936e positioned between members 930, 932. A member 930, 932 is captivated between plastic thrust bearing 936e and a second plastic thrust bearing 936f. A stainless steel round flat washer 936g and a curved disc spring 936h are provided between bearing 936f and the head of screw 936c as shown, with bearing 936d abutting washer 936f. Spring 936h maintains tension between thrust bearings 936e, 936g. Finally, another curved disc spring 936i is provided and seats in a recess 930c or 932c of a member 930, 932, respectively. Curved disc spring 936i allows for greater machining tolerances for recesses 930c, 932c and preferably keeps bearing 936d in contact with washer 936f. Coupling assemblies 936 thus allow some adjustment of tensioning so that a desired level of force permits movement of members 930, 932 with respect to one another. By loosening or tightening each of assemblies 936, frictional resistance to sliding or telescoping of members 930, 932 with respect to each other may be selected.

Another rotational joint 942 is disposed proximate the free end of portion 924 opposite the free end at which rotational joint 920 is disposed. Joint 942 is disposed along an axis 944. In particular, an extension 930a of member 930 is coupled along axis 944 at rotational joint 942 to a joint member 946. Rotational joint 942 may permit a 360° range of rotation about axis 944. Preferably, axes 934, 944 are parallel and disposed in different planes.

Figure 40:
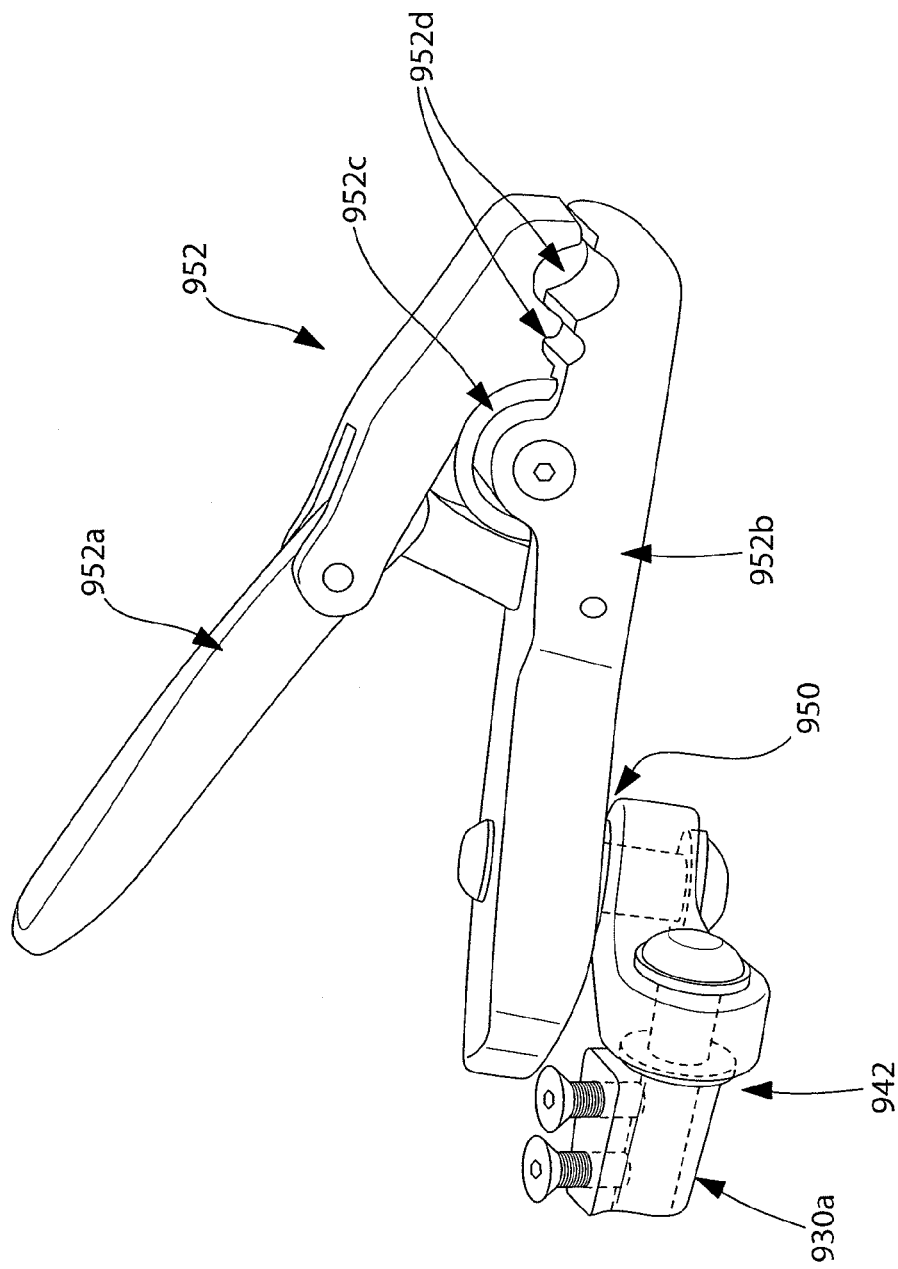

Joint member 946 is coupled along an axis 948 at yet another rotational joint 950 to a laparoscopic device retaining portion 952. Rotational joint 950 may permit a 360° range of rotation about axis 948. Laparoscopic device retaining portion 952, for example, may be a clamp formed by a pair of jaw members 952a, 952b with a laparoscopic device grasping region 952d formed by jaw portions that are spring biased toward one another and handle regions that are spring biased away from one another, the biasing accomplished using a spring 952c. Preferably, laparoscopic device grasping region 952d is sized to receive a laparoscopic device such as an endoscopic camera, shown schematically as device 954. Thus, grasping region 952d may be sized, for example, to grasp a 5 mm and/or 10 mm laparoscope (as shown in FIG. 40, two cylindrical regions are sized for this purpose). In the exemplary embodiment, axes 944, 948 are disposed at about 90° with respect to each other.

In order to provide sufficient clamping strength so that a laparoscopic device 954 may be securely and releasably retained within grasping region 952d of retaining portion 952, without undesired slippage or rotation, a strong spring mechanism is provided. In particular, as shown in FIGS. 4P-4U, spring 952c in part elastically biases jaw members 952a, 952b toward one another so that grasping region 952d is in a closed position. In the preferred exemplary embodiment, spring 952c is a Type 302 stainless steel torsion spring providing a torque of about 21 in.-lbs. (McMaster-Carr part number 9287K103 with the following characteristics: 90° deflection angle clockwise wound, spring outer diameter about 0.9 inch, wire diameter about 0.1 inch, length about 3.5 inches, maximum rod outer diameter about 0.5 inch, body length/spring length at torque about 0.6 inch, and about 3.25 active coils). However, in alternate embodiments, other elastic members instead of a torsion spring may be used and other spring characteristics may be specified as long as proper retention is provided in region 952d. Thus, even forces due to power cords, etc., that may be associated with a laparoscopic device 954 may be sufficiently countered while device 954 is disposed in grasping region 952d.

Because of the substantial torque provided by spring 952c to securely retain a laparoscopic device 954 in grasping region 952d, a user may need very significant hand strength to be able to compress the handle portions of jaw members 952a, 952b toward one another. To enhance usability in view of the torque of spring 952c, jaw member 952a has a forked, bifurcated design with a first portion $952a_1$ having a U-shaped region that receives a second portion $952a_2$. A first pin 953a pivotally associates portions $952a_1$ and $952a_2$ to one another, while a second pin 953b pivotally associates second portion $952a_2$ to lever link 955. Lever link 955 is further pivotally associated with jaw member 952b with a third pin 953c. A boss 959a of first portion $952a_1$ with a through hole therein is received in the through hole of a boss 959b of jaw member 952b and these jaw members 952a, 952b are coupled to one another with a screw 957a that extends in the through hole of boss 959a and tightly abuts a coaxial set screw 957b. Spring 952c is disposed about boss 959b with one leg resting against ledge 961a and the other leg resting against ledge 961b of jaw members 952a, 952b, respectively. During operation, in order to open grasping region 952d, a user may grasp in one hand and squeeze (1) portion $952a_1$ of jaw 952a which forms a first handle region and (2) jaw member 952b which forms a second handle region. The use of a jaw member 952a having portions $952a_1$ and $952a_2$ as well as lever link 955 provides a mechanical advantage to the user when changing the size of the openings in grasping region 952d, e.g. to allow insertion or release of a laparoscopic device 954 therein. Preferably, the mechanical advantage is such that the turning force applied by a user to move jaw members 952a, 952b with respect to one another is less than half the turning force otherwise required for the spring 952c.

In an exemplary preferred embodiment, when jaw members 952a, 952b are closed as shown in FIGS. 4P and 4Q, portion $952a_2$ is separated from portion 952b by an angle J of about 35°.

Retaining portion 952 preferably may be used to secure the shaft portion of a laparoscopic device such as an endoscopic camera. A sterile sleeve drape may be used to cover the entire apparatus and to be imbricated into grasping region 952d. Preferably, while spring-biased jaw members are configured to hold the laparoscopic device securely, they also permit the device to be manually rotated about its linear axis with enough frictional resistance to prevent undesired rotational movement.

The rotational joints of holder 900 such as rotational joints 914, 920 for example may be formed as follows. An internally threaded bolt 956 is disposed with the head thereof abutting a first washer 958a. The washer 958a abuts a first side of a joint member such as member 916 while a second washer 958b abuts an opposite side of member 916 with bolt 956 extending therethrough. The shaft of bolt 956 extends through hole 962 and a coaxial hole in an adjacent component such as member 932. An externally threaded bolt 964 is threadably received in internally threaded bolt 956.

Figure 4V:
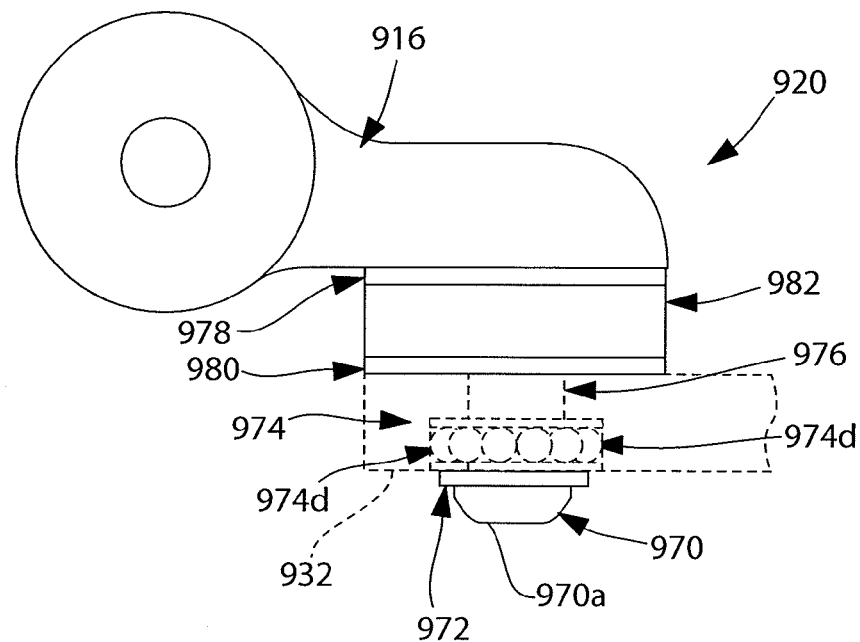
Figure 4W:
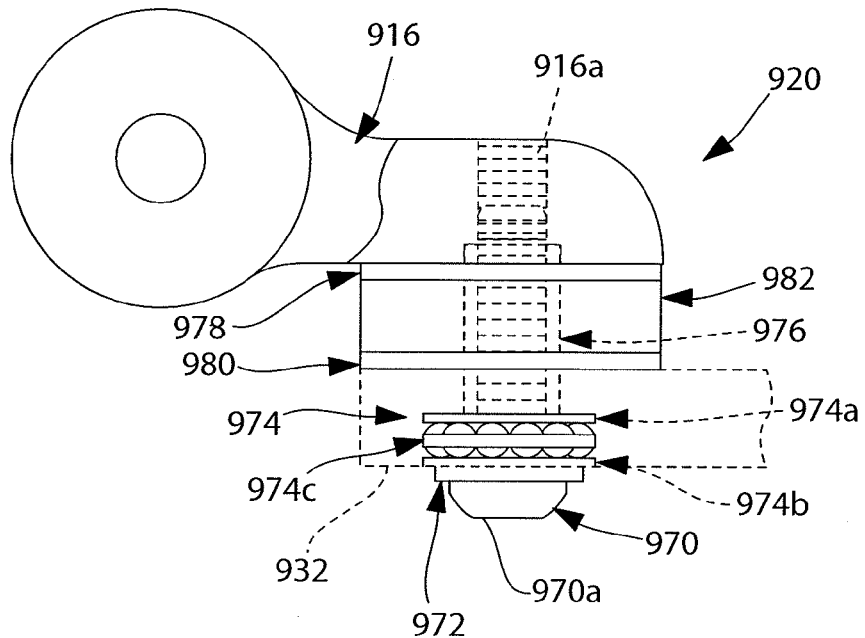

In another exemplary embodiment, the rotational joints of holder 900 such as rotational joints 908, 914, 920, 942, 950 for example may be formed with thrust bearings as follows. Although in FIGS. 4V and 4W an exemplary rotational joint 920 is shown, the construction of this joint also may reflect the construction of exemplary rotational joints 908, 914, 942, 950 according to this embodiment. Rotational joint 920 couples joint member 916 and sliding member 932 (shown in phantom). Joint 920 includes a central screw 970 which is threadably received in a threaded hole 916a in joint member 916. A Belleville or conical washer 972 abuts head 970a of screw 970 as well as a steel ball thrust bearing 974 (which for example may be carbon steel or stainless steel). Washer 972 creates a spring tension to broaden the window of adjustability of holder 900 during assembly and accommodates slight wear that may occur in operation of holder 900. In turn, thrust bearing 974 is mounted on a sleeve 976 which extends from within a central opening in thrust bearing 974 to within a recessed region in joint member 916. Rotational joint 920 further includes a pair of washers 978, 980, preferably formed of stainless steel, and a spacer 982 disposed therebetween, together mounted on sleeve 976. Washer 978 abuts and preferably is bonded to joint member 916 while washer 980 abuts and preferably is bonded to sliding member 932. Washers 978, 980 may rotate freely with respect to spacer 982. Spacer 982 for example may be formed of Delrin® AF Blend (Acetal homopolymer, PTFE-filled). As is known in the art, a high performance miniature steel ball thrust bearing 974 for example may be formed of a pair of precision chrome-steel washers 974a, 974b and a ball cage 974c that is bronze or stainless steel with steel balls 974d disposed therein (e.g., McMaster-Carr part number 7806K63). In use, rotational joint 920 advantageously accommodates thrust loads—it can accommodate axial thrust along the axis of the "shaft" it supports—while also providing desired rotational movement between joint member 916 and sliding member 932. Although a steel ball thrust bearing 972 is shown, other types of thrust bearing constructions instead may be used, and also other types of bearings instead may be used. Moreover, although rotational joint 920 with thrust bearing 972 has been shown in the exemplary context of joint member 916 and sliding member 932, in the present embodiment such joint constructions with thrust bearings may be used in one or more, and preferably each of rotational joints 908, 914, 920, 942, 950.

Figure 4X:
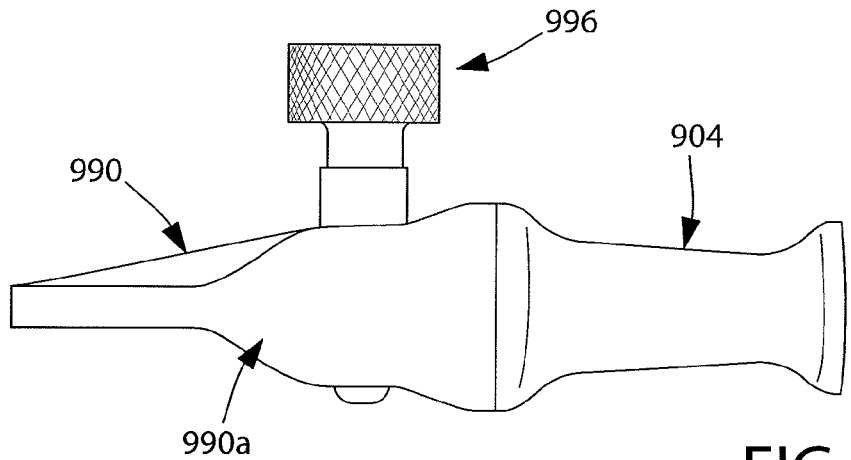
Figure 4Y:
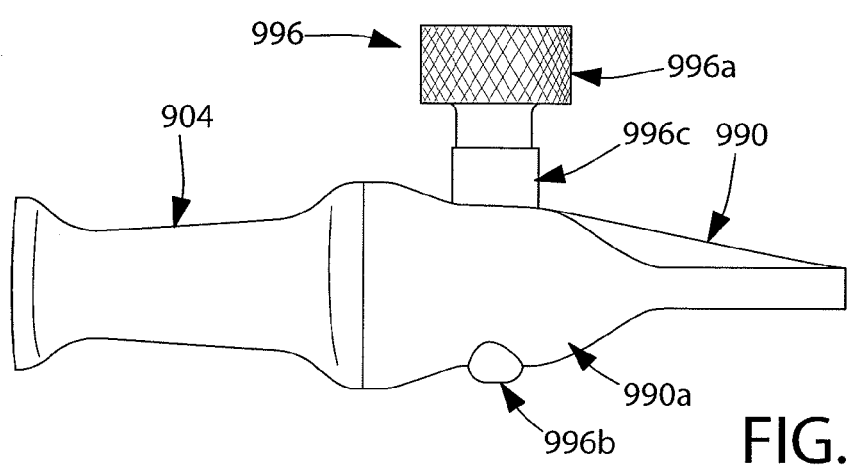
Figure 4Z:
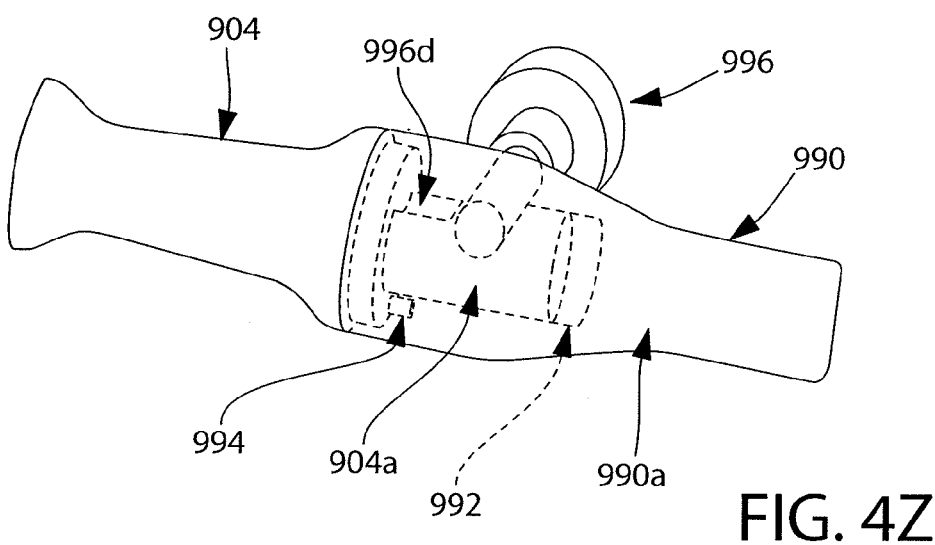

While holder 900 for example is shown in FIGS. 4F and 4G with a coupling portion 902 in the form of a post that couples to body portion 904, another exemplary embodiment of a coupling portion 990 coupled to body portion 904 is shown in FIGS. 4X-4Z. Coupling portion 990 is configured, for example, as an adaptor for coupling holder 900 to other types of arrangements as known in the art. Thus, holder 900 may be attached to a variety of positioning arms not limited for example to the curvilinear articulating arm assembly 12 in FIG. 1. Portion 990 includes a central hole 992 that receives a projection 904a extending from an end of body portion 904. Body portion 904 and coupling portion 990 are further aligned with a pin 994 extending in holes in portions 904, 990 that are coaxial when in alignment with one another. An interface lock 996 extends into member 990a of coupling portion 990 and is rotatably associated with projection 904a of body portion 904. Interface lock 996 for example may include a knurled knob portion 996a, a cylindrical post 996b, a sleeve 996c, and a set screw 996d. Exemplary operation of such an interface lock 996 is described elsewhere herein with respect to an interface lock 683 shown in FIG. 6U.

Thus, laparoscopic device 954 may be positioned as desired using the combined freedom of movement provided by rotational joints 908, 914, 920, 942, 950, linear length adjustment portion 924, as well as the rotation provided by coupling portion 902 when received in portion 82 of free handle 62 of articulating arm assembly 14.

Preferably, frictional movement is provided by rotational joints 908, 914, 920, 942, 950, linear length adjustment portion 924, as well as coupling portion 902 when received in portion 82 of free handle 62 of articulating arm assembly 14, as described with respect to holder 800 above. Preferably the friction is sufficient to hold the laparoscopic device regardless of orientation but selected so that the device is easily movable for reorientation through manual manipulation by a user. Preferably, when a user positions a laparoscopic device 954 using holder 900, the rotational and linear movements provided by the components of holder 900 provide a generally uniform feel to the user. In other words, during manual manipulation of a device 954 coupled to holder 900, it feels to the user as though the user encounters the same degree of resistance to movement of the laparoscopic device 954 regardless of the direction in which device 954 is moved/oriented. In one exemplary preferred embodiment, rotational joints 908, 914, 920 proximate coupling portion 902 for interfacing with articulating arm assembly 14 may have about two times the frictional resistance to movement as rotational joints 942, 950 proximate laparoscopic device retaining portion 952.

Next, with reference to FIGS. 5A-5H, yet another exemplary embodiment of a laparoscopic instrument holder 1000 according to the present invention is shown. As with previous embodiments, in an exemplary embodiment holder 1000 includes three rotational axes at a proximal end and two rotational axes at a distal end. Holder 1000 includes a coupling portion 1002 in the form of a post. Coupling portion 1002 preferably is configured to be received in portion 82 of free handle 62 of articulating arm assembly 14, as will be described later. Holder 1000 includes a body portion 1004 coupled along axis 1006 at a first rotational joint 1008 to a first joint member 1010. In the exemplary embodiment, first rotational joint 1008 may permit a 360° range of rotation about axis 1006.

In some embodiments, a series of rotational joints may be provided. In the exemplary embodiment, first member 1010 is coupled along an axis 1012 at a second rotational joint 1014 to a second joint member 1016. Second rotational joint 1014 may permit a 360° range of rotation about axis 1012. Second joint member 1016 is coupled along an axis 1018 at a third rotational joint 1020 to a linear length adjustment portion 1024, which will be described shortly. Third rotational joint 1020 may permit a 360° range of rotation about axis 1018. Preferably, third rotational joint 1014 is disposed proximate a free end of portion 1024.

In one preferred exemplary embodiment, axes 1006, 1012 are disposed at about 90° with respect to each other, and axes 1012, 1018 are disposed at about 90° with respect to each other. In addition, the combination of rotational joints 1008, 1014, 1020 permits movement in three separate planes, it being possible for at least one pair of said planes (e.g., as defined by joints 1008, 1020) to be parallel to one another. The combination of rotational joints 1008, 1014, 1020 may permit movement in three separate planes which may be nonparallel to one another.

In the exemplary embodiment, linear length adjustment portion 1024 forms a sliding mechanism in which a generally tubular first sliding member 1030 is coupled to a generally tubular second sliding member 1032 and are slidably associated with one another. Portion 1024 forms an extendable section of holder 1000 that for example provides adjustability to the length of holder 1000. In the exemplary embodiment, members 1030, 1032 are restricted to move with respect to one another along central sliding axis 1034. Advantageously, linear length adjustment portion 1024 permits a user to reposition a laparoscopic device 1054, for example into and out of an opening in a patient, with gross movement in a linear direction, as compared to angulation. For example, linear length adjustment portion 1024 may permit about 5 or about 6 inches of linear movement of a device 1054 held by holder 1000.

Figure 5A:
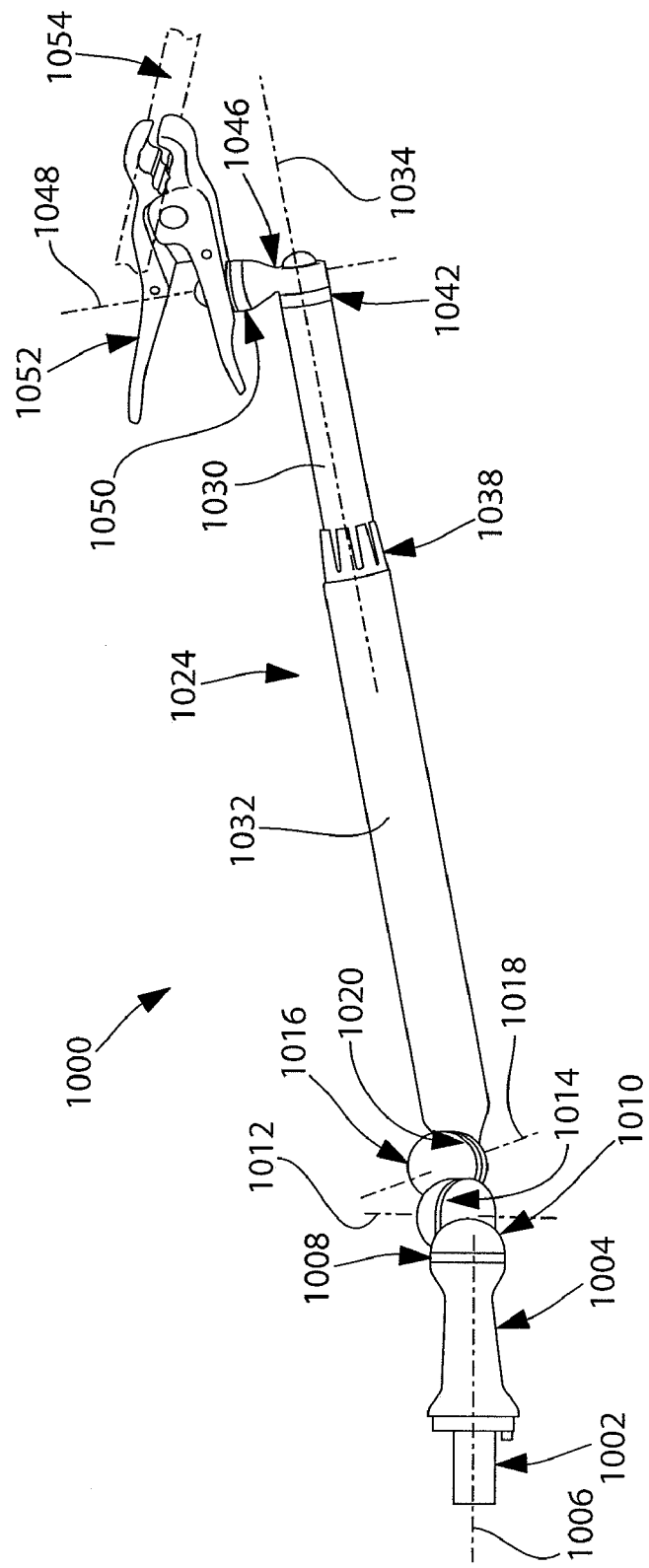
FIGS. 5A-5H show another embodiment of a laparoscopic instrument holder according to the present invention, including (5A) a perspective view with a laparoscopic instrument retained by said holder, (5B) a first partial side view, (5C) a second partial side view, (5D) a third partial side view, (5E) a partial cross-sectional side view of a piston member couple to a sliding member, (5F) a partial perspective view of several rotational joints, (5G) a partial perspective view of a rotational joint with joint members, and (5H) a partial perspective view of a clamp.
Figure 5B:
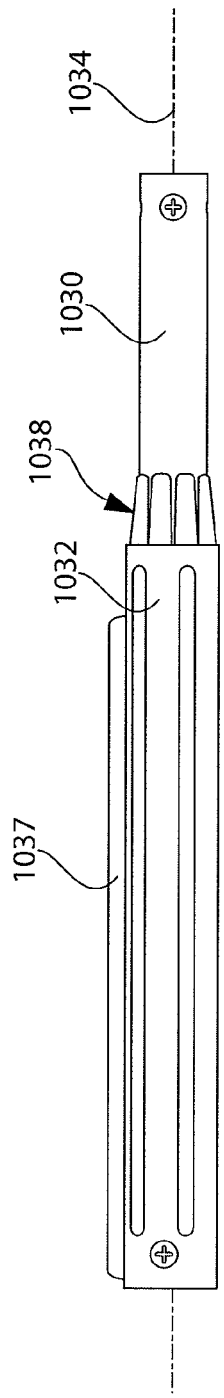
Figure 5C:
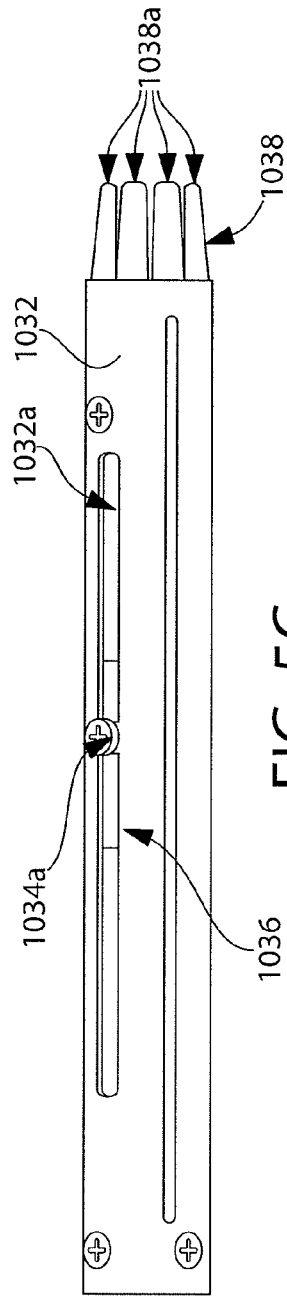
Figure 5D:
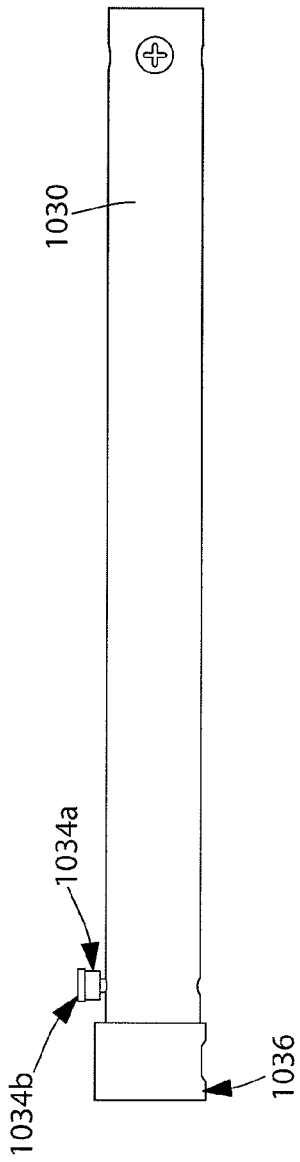

Member 1030 preferably is received within, and telescopes with respect to member 1032. As shown in FIG. 5C, member 1032 is hollow and is provided with a slot 1032a. A roller key 1034a is secured to member 1030 with a rivet 1034b; a piston member 1036 is coupled to a free end of member 1030 (see FIG. 5E) and rivet 1034b extends in a coaxially disposed holes 1036*a*, 1030*a* in members 1036, 1030 respectively. Roller key 1034*a* coupled to member 1030 is movable within slot 1032*a* of member 1032 and preferably is a miniature high precision stainless steel ball bearing. A cover 1037 may be secured to member 1032 over slot 1032*a*, for example, for safety and aesthetic reasons. Member 1032 also may be provided with a bushing 1038 to provide support for member 1030 and to assist in preventing a sterile sleeve drape covering holder 1000 from being caught during movement of member 1030 with respect to member 1032. Bushing 1038 includes a plurality of fingers 1038*a* disposed radially with respect to axis 1034. Advantageously, the use of fingers 1038*a* allows an adequate interference fit to be provided with minimal drag between fingers 1038*a* and the outer surface of member 1030 to prevent the sterile sleeve drape covering holder 1000 from being inadvertently caught during movement. Bushing 1038 may be formed, for example, of Delrin® AF Blend (Acetal homopolymer, PTFE-filled).

Figure 5E:
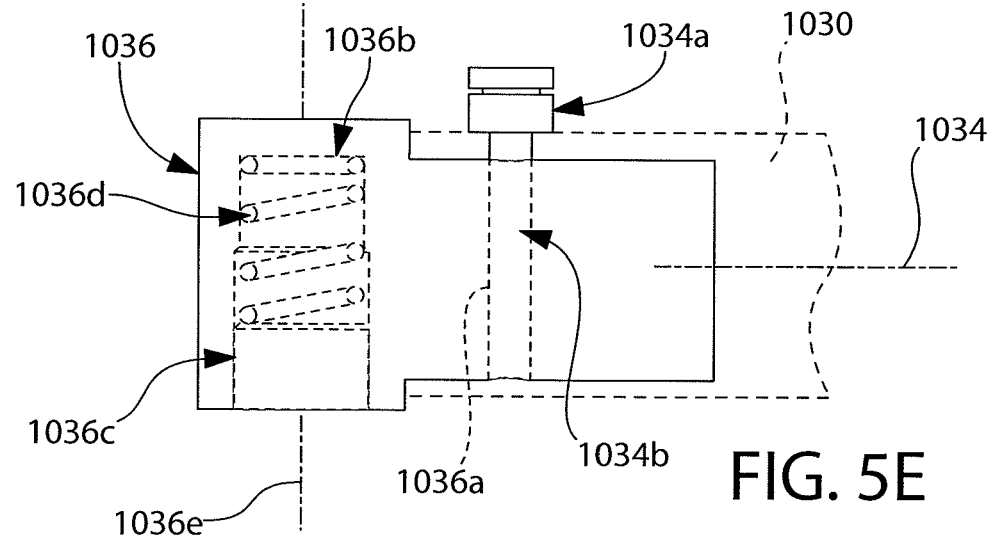
Figure 5F:
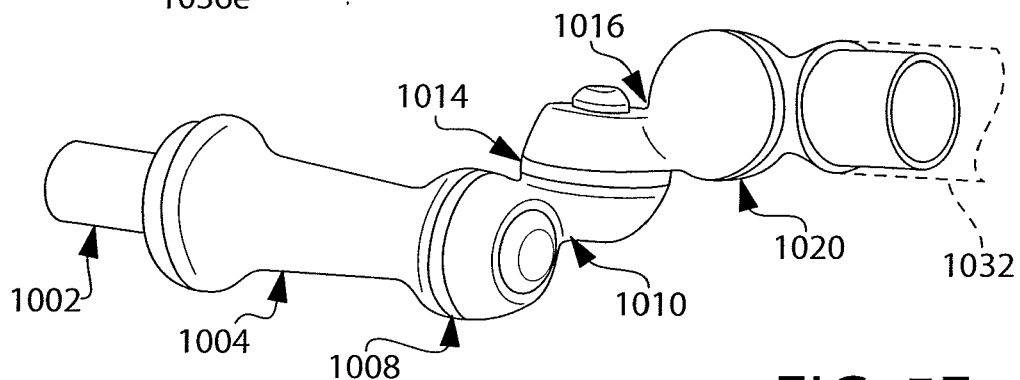

As shown in FIG. 5E, piston member 1036 is spring-loaded. In particular, a spring 1036*b* and a plunger 1036*c* are disposed within a hollow cylindrical region 1036*d* in piston member 1036 for movement along axis 1036*e*. Preferably axis 1036*e* is disposed perpendicular to axis 1034. By providing the spring/plunger arrangement, a consistent drag force by may be provided for movement of members 1030, 1032 with respect to each other as plunger 1036*c* bears against the inner wall of member 1032. In an exemplary embodiment, the following components and materials may be used: spring 1036*b* may be stainless, ½" long×0.36" OD×0.032" wire; the plunger may be 0.43" long with an OD of 0.375 and may be made of Delrin® AF Blend; the depth of the hole in the piston may be ¾" and the diameter of the piston may be 0.86", sized for clearance to the ID of member 1032.

Turning back to FIG. 5A, another rotational joint 1042 is disposed proximate the free end of member 1030 opposite the free end of member 1032 at which rotational joint 1020 is disposed. Joint 1042 is disposed along axis 1034. Rotational joint 1042 may permit a 360° range of rotation about axis 1034. Joint member 1046 is coupled along an axis 1048 at yet another rotational joint 1050 to a laparoscopic device retaining portion 1052. Rotational joint 1050 may permit a 360° range of rotation about axis 1048. Laparoscopic device retaining portion 1052, for example as shown in FIG. 5H, may be a clamp formed by a pair of jaw members 1052*a*, 1052*b* with a laparoscopic device grasping region 1052*d* formed by jaw portions that are spring biased toward one another and handle regions that are spring biased away from one another, the biasing accomplished using a spring 1052*c*. Preferably, laparoscopic device grasping region 1052*d* is sized to receive a laparoscopic device such as an endoscopic camera, shown schematically as device 1054. Preferably, grasping region 1052*d* is formed by material softer than aluminum to prevent marring or denting of surfaces of delicate laparoscopic device 1054 which typically is thin-walled. In the exemplary preferred embodiment, polyurethane covers 1052*e* are provided. Covers 1052*e* for example may be formed of 85 or 95 durometer polyurethane, permitting devices 1054 to even be twisted out of grasping region 1052*d* without damage occurring. In the exemplary embodiment, axes 1034, 1048 are disposed at about 90° with respect to each other.

Further details concerning retaining portion 1052 were previously provided in the context of retaining portion 952 of a previous embodiment.

Thus, retaining portion 1052 preferably may be used to secure the shaft portion of a laparoscopic device such as an endoscopic camera. A sterile sleeve drape may be used to cover the entire apparatus and to be imbricated into grasping region 1052*d*. Preferably, while spring-biased jaw members are configured to hold the laparoscopic device securely, they also permit the device to be manually rotated about its linear axis with enough frictional resistance to prevent undesired rotational movement.

Figure 5G:
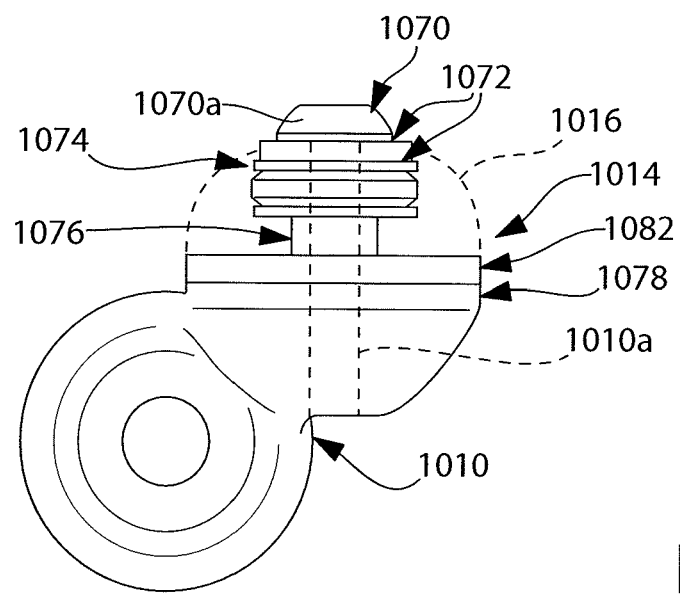
Figure 5H:
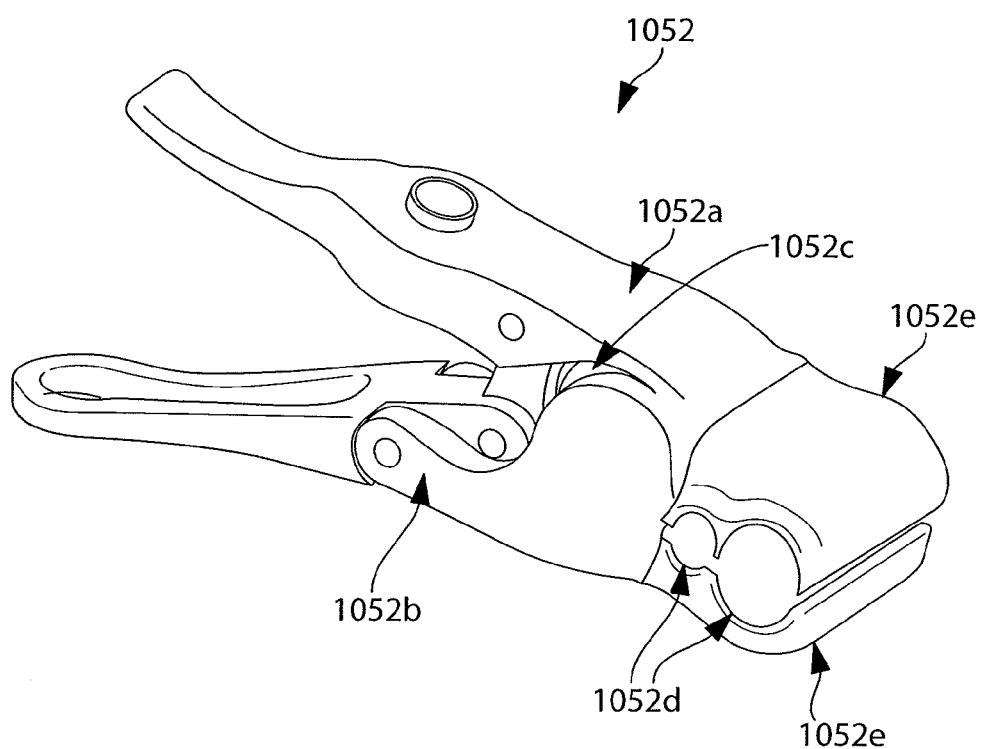
Figure 51:
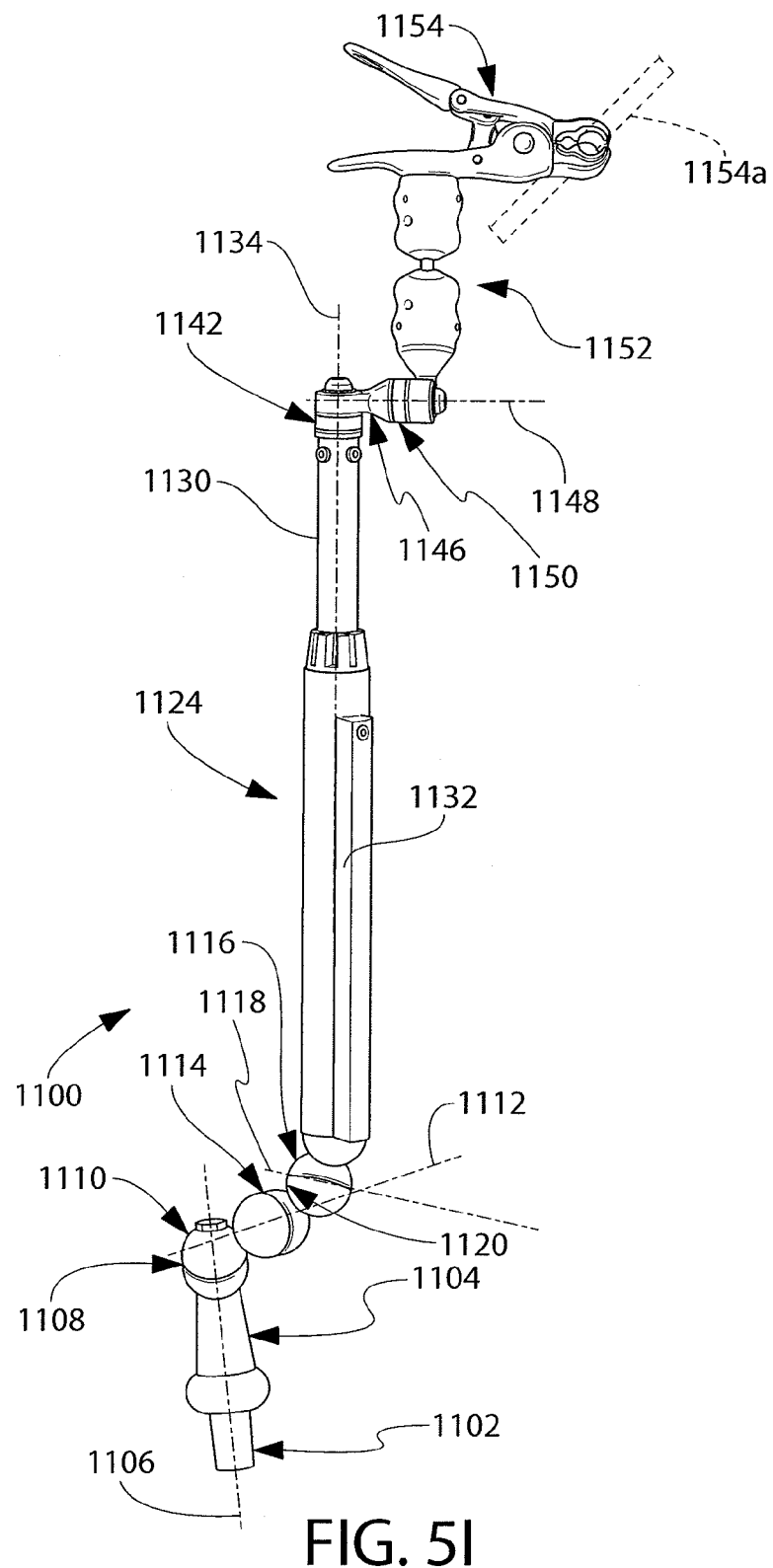
Figure 5J:
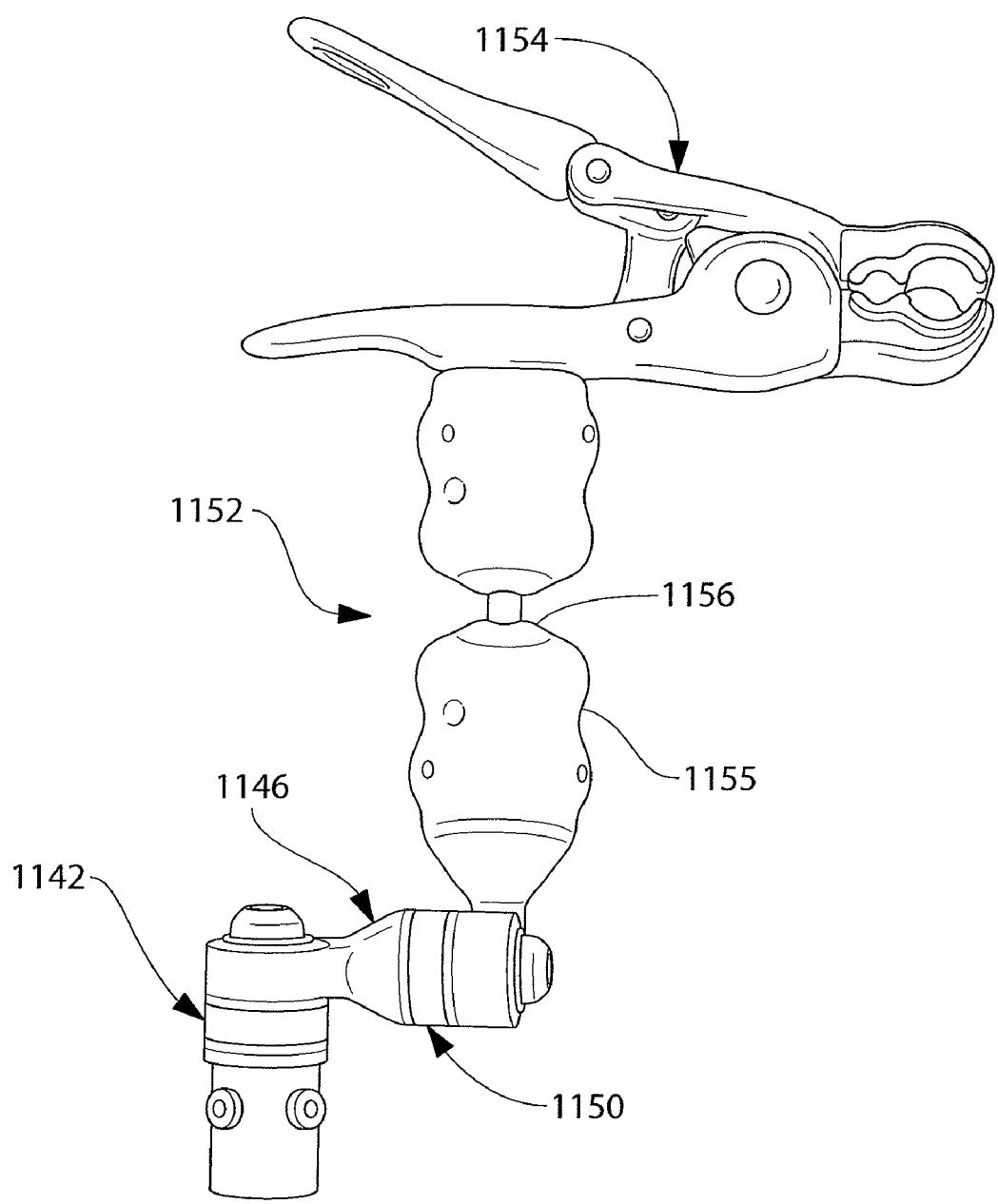
Figures 5K, 5L:
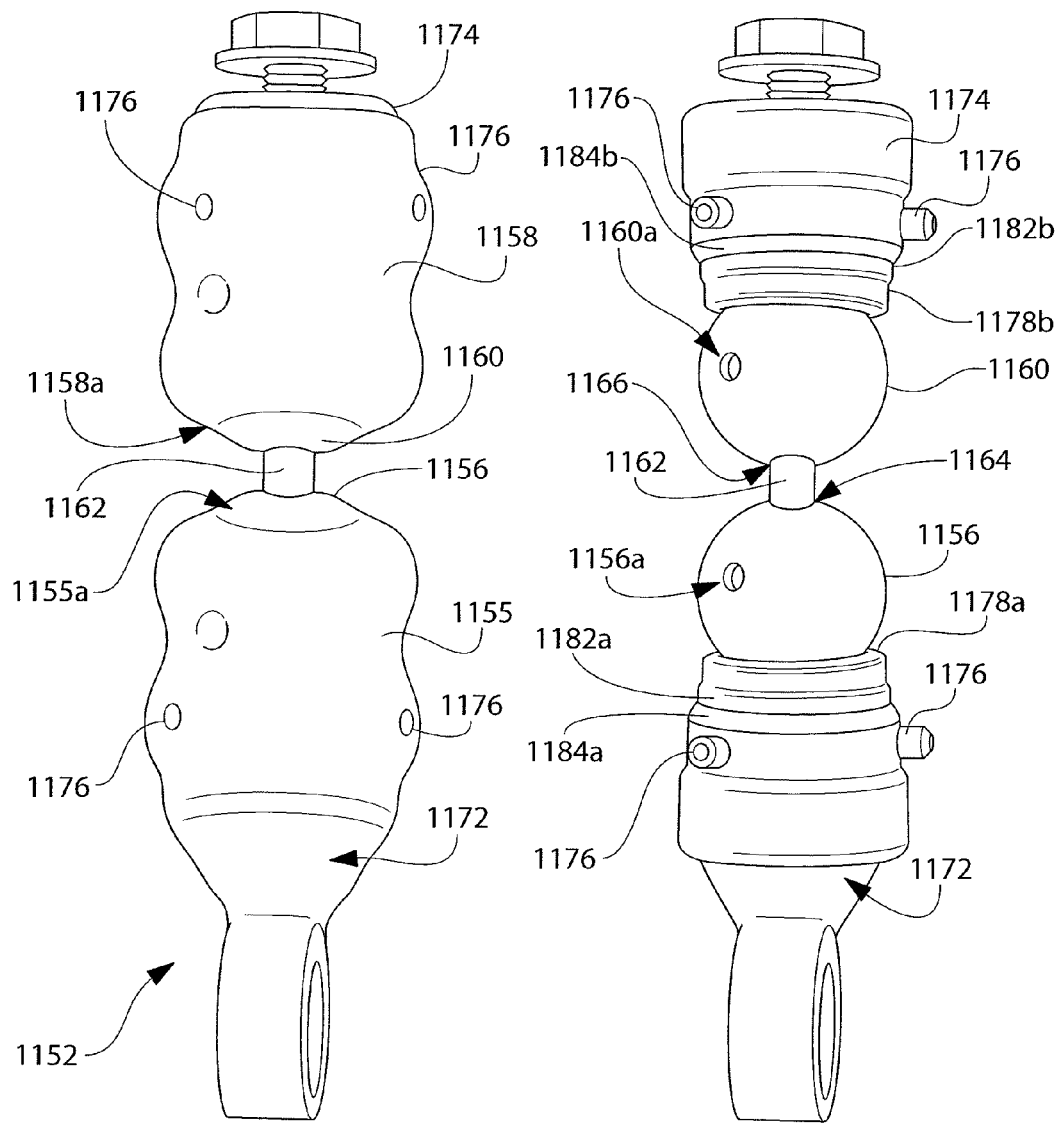

An exemplary rotational joint 1014 is shown in FIG. 5G. Each of joints 1008, 1014, 1020 for example may have the same construction, and joint 1014 is described in particular. Although similar to these joints, the joints 1042, 1050 proximate retaining portion 1052 have similar constructions to joint 920 shown in FIGS. 4V-4W a previously described (e.g., with two stainless steel washers and a Delrin® AF Blend spacer therebetween that is not bonded to its surroundings). However, as will be described, components in these various joints may be formed of different materials depending on whether the joint is located near the proximal or distal end of holder 1000.

In a preferred exemplary embodiment, joint 1014 may include a thrust bearing. Rotational joint 1014 couples joint member 1010 to joint member 1016 (shown in phantom). Joint 1014 includes a central screw 1070 which is threadably received in a threaded hole 1010*a* in joint member 1010. A pair of Belleville or conical washers 1072 are disposed proximate head 1070*a* of screw 1070 as well as a high performance miniature steel ball thrust bearing 1074 that for example may be formed of a pair of precision chrome-steel washers 974*a*, 974*b* and a ball cage 974*c* that is bronze or stainless steel with steel balls 974*d* disposed therein (e.g., McMaster-Carr part number 7806K63). In turn, thrust bearing 1074 is mounted on a sleeve 1076 which extends from within a central opening in thrust bearing 1074 to within a recessed region in joint member 1016. Rotational joint 1014 further includes a washer 1078 preferably formed of stainless steel and a spacer 1082 adjacent sleeve 1076. Washer 1078 abuts joint member 1010. Washer 1078 preferably is bonded to joint member 1010 while spacer 1082 preferably is bonded to joint member 1016, it being possible for washer 1078 and spacer 1082 to rotate with respect to each other. The use of such a joint with a thrust bearing was described previously with respect to joint 920 of another embodiment, and the previous description also applies to this embodiment.

In a preferred exemplary embodiment, members 1030, 1032 are formed of 6061-T6 aluminum due to the strength to weight ratio of this material. However, other materials could be used for example thin wall steel. Washers such as washers 1072 may be formed of stainless steel.

The spacers such as spacer 1082 in rotational joints 1008, 1014, 1020 at the proximal end may be formed of Multifil™ sliding bearing material which is polytetrafluoroethylene (PTFE)-based and available from GGB North America LLC. Advantageously, the Mutifil material has low stiction for the present application—it shows almost no signs of "sticking" in the operating conditions of holder 1000. On the other hand, the spacers in the rotational joints at the distal end such as joints 1042, 1050 may be formed of Delrin® AF Blend (Acetal homopolymer, PTFE-filled). Different materials were used for the spacers at the proximal and distal ends for several reasons. First, Multifil was only available in a limited range of thicknesses. Because the spacers at the proximal end were of relatively large diameters (1⅛ inch), forces against the spacers could be spread over this relatively large area thus allowing a "smaller" thickness of spacer to be used without risking plastic deformation. The spacers at the distal end proximate retaining portion 1052 have comparatively small diameters (¾ inch), and thus "larger" spacer thickness was needed to accommodate forces on these spacers without risking plastic deformation. Multifil was not available in the thickness needed for the spacers at the distal end and thus another material (Delrin® AF Blend) was chosen. Second, stiction appeared to be more of an issue in joints at the proximal end near body portion 1004 (than in joints proximate retaining portion 1052); Multifil thus was the preferred material for addressing stiction concerns.

In an exemplary embodiment, holder 1000 may have a fully telescoped length of about 19.5 inches as measured from the first rotational joint 1008 at the proximal end proximate body portion 1004 to the center of the clamp jaw cover 1052e; the unextended length of holder 1000 may be about 14.25 inches. Thus, telescoping action may provide about 5 to about 5.5 inches of adjustment in length of holder 1000.

Joints 1008, 1014, and 1020 each are set to about 2 ft-lbs of torque, while joint 1042 is set to about 0.8 ft-lbs of torque and joint 1050 is set to about 1.2 ft-lbs of torque. The telescoping action of members 1030, 1032 may be set to have about an axial force of about 1 lb.

In use, the port in a patient into which a device 1054 is introduced may serve as a fulcrum. The clamp of holder 1000 preferably is capable of holding about ¼ lb. of weight from device 1054 when holder 1000 is fully extended. Although a typical endoscopic scope may weigh about ¼ lb., various cables associated with the scope increase the weight that must be supported. However, support is further provided by the port formed in the body into which the scope is inserted, helping to assist in accommodating the additional weight.

The rotational joints described herein, for example, may permit limited rotation such as rotation through an angle of about 180° or an angle of about 270°, or may permit about 360° of rotation about an axis of the rotational joint.

Next, an exemplary method of using holder 900 is described although this method applies to other holders described herein such as holder 1000. In use, the position of holder 900 should be checked for suitable working range near the planned camera port site. The optimum attachment point for the articulating arm assembly 14 for example on a surgical bed railing should be determined after the patient is positioned and asleep and before the prep. Initially, linear length adjustment portion 924 need not be telescoped, although portion 924 should be fully extended for draping. Assembly 14 should be oriented to near vertical for prepping and draping the patient and the arm. The drape for assembly 14 preferably should be placed after the skin prep but before the final large procedure drape is placed. A separate skirt/half-sheet drape may be clipped around the base of the system after the large patient drape is placed. Assembly 14 then should be contoured closely to the patient to minimize its footprint and brought adjacent to the camera port. In use, the assembly 14 should be closely contoured to the patient and holder 900 disposed approximately parallel to the skin (perpendicular to the port) to minimize interference and clutter. Also, although it is possible that in one combination joints 910, 914, 920 may be aligned generally in the same plane, it is desirable to have at least one of these joint out of plane relative to the others to start. If the laparoscopic device 954 is an endoscopic camera, preferably the shaft of the device is grasped in clamp 952 as close as possible to the camera body. A laparoscopic device 954 coupled to holder 900 may be moved, for example, in six degrees of freedom with the combination of rotational joints 942, 950 and grasping region 952d of clamp 952 which permits rotation of device 954 therein.

Referring now to FIGS. 5I-5N, a further exemplary embodiment of a laparoscopic instrument holder 1100 according to the present invention is shown. Holder 1100 is similar to holder 1000 but instead includes ball and socket joints proximate the laparoscopic device retaining portion, as will be described. Otherwise, the description of holder 1000 above applies to holder 1100.

Exemplary holder 1100 includes three rotational axes at a proximal end, two rotational axes at a distal end, and separately two ball joints for rotational motion at the distal end permitting articulation with respect to an axis defined by a shaft as will be described.

Holder 1100 includes a coupling portion 1102 in the form of a post. Coupling portion 1102 preferably is configured to be received in portion 82 of free handle 62 of articulating arm assembly 14, as described separately herein. Holder 1100 includes a body portion 1104 coupled along axis 1106 at a first rotational joint 1108 to a first joint member 1110. In the exemplary embodiment, first rotational joint 1108 may permit a 360° range of rotation about axis 1106.

In the exemplary embodiment, first member 1110 is coupled along an axis 1112 at a second rotational joint 1114 to a second joint member 1116. Second rotational joint 1114 may permit a 360° range of rotation about axis 1112. Second joint member 1116 is coupled along an axis 1118 at a third rotational joint 1120 to a linear length adjustment portion 1124, as described previously with respect to linear length adjustment portion 1024 of holder 1000. Third rotational joint 1120 may permit a 360° range of rotation about axis 1118. Preferably, third rotational joint 1114 is disposed proximate a free end of portion 1124.

In one preferred exemplary embodiment, axes 1106, 1112 are disposed at about 90° with respect to each other, and axes 1112, 1118 are disposed at about 90° with respect to each other. In addition, the combination of rotational joints 1108, 1114, 1120 permits movement in three separate planes, it being possible for at least one pair of said planes (e.g., as defined by joints 1108, 1120) to be parallel to one another. The combination of rotational joints 1108, 1114, 1120 may permit movement in three separate planes which may be nonparallel to one another.

In the exemplary embodiment, linear length adjustment portion 1124 forms a sliding mechanism for telescoping action of portions 1130, 1132 with respect to each other, as described previously with respect to holder 1000.

Another rotational joint 1142 is disposed proximate the free end of member 1130 opposite the free end of member 1132 at which rotational joint 1120 is disposed. Joint 1142 is disposed along axis 1134. Rotational joint 1142 may permit a 360° range of rotation about axis 1134. Joint member 1146 is coupled along an axis 1148 at yet another rotational joint 1150 to a ball and socket joint portion 1152, which in turn is coupled to a laparoscopic device retaining portion 1154. Rotational joint 1150 may permit a 360° range of rotation about axis 1148. Laparoscopic device retaining portion 1154 for example may be similar to portion 1052 described previously with respect to holder 1000, and is shown in FIG. 5I with a laparoscopic device 1154a retained therein.

Figures 5M, 5N:
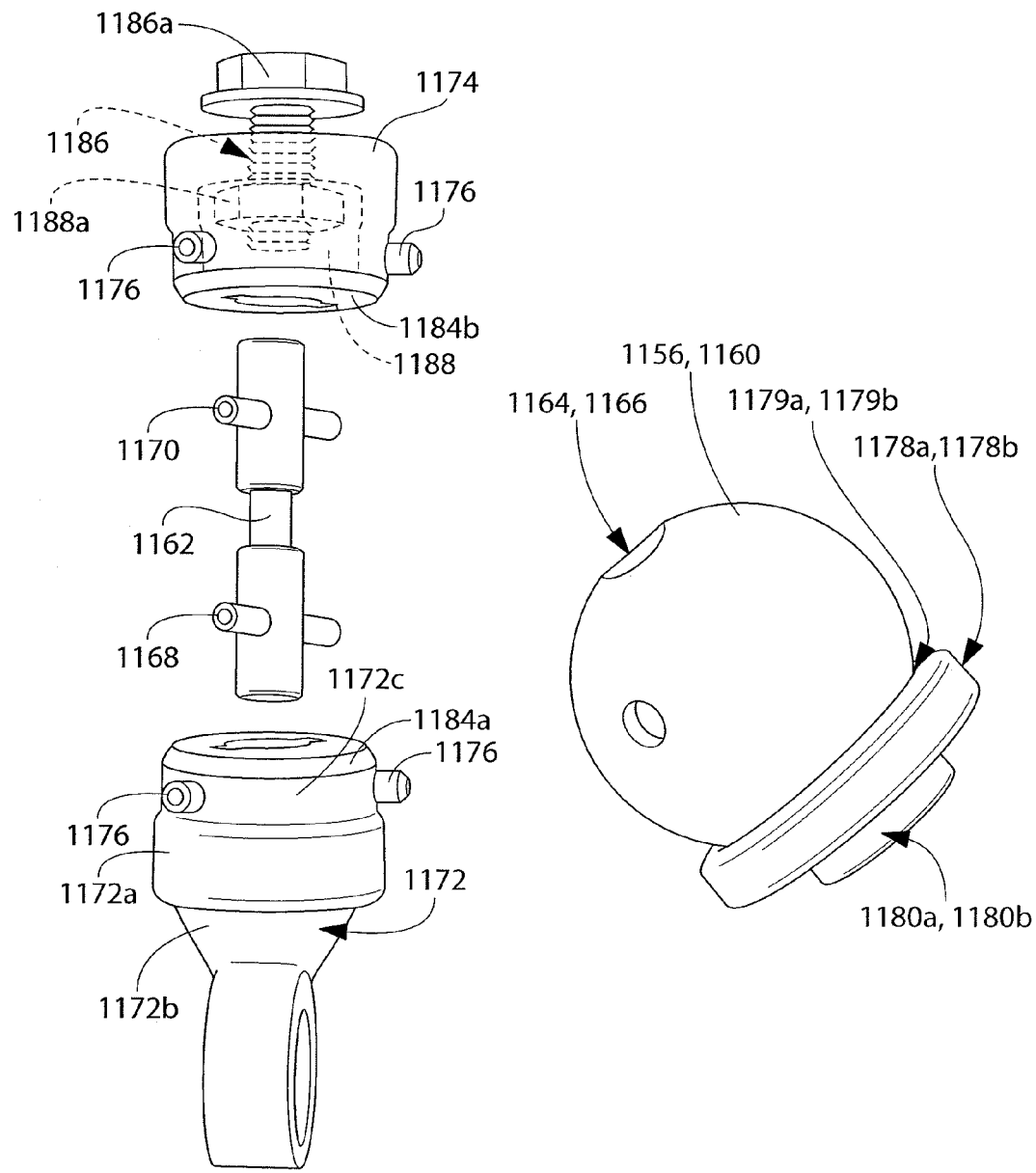

Turning particularly to FIGS. 5J-5N, ball and socket joint portion 1152 next will be described. In the exemplary embodiment, ball and socket joint portion 1152 includes a pair of ball and socket joints, although in other embodiments a single ball and socket joint or more than two ball and socket joints may be provided. Exemplary portion 1152 thus includes a first socket 1155 for receiving a first ball 1156 as well as a second socket 1158 for receiving a second ball 1160. Balls 1156, 1160 are rigidly coupled to one another by a shaft 1162 received in opposing bores 1164, 1166, respectively. Shaft 1162 is secured to balls 1156, 1160 by pins 1168, 1170 that extend respectively in through holes 1156a, 1160a. As shown in FIG. 5M, pins 1168, 1170 also extend through shaft

1162. Pins 1168, 1170 may be secured to balls 1156, 1160 and/or shaft 1162 such as with a press fit.

Each of sockets 1155, 1158 have an opening 1155*a*, 1158*a* through which balls 1156, 1160 respectively protrude. In use, for example, the movement of socket 1155 with respect to ball 1156 is limited by the size of the opening 1155*a* because the internal rim defining opening 1155*a* limits the movement of shaft 1162. In one preferred exemplary embodiment, each of sockets 1155, 1158 can be angulated by as much as about 45° transverse to shaft 1162, while sockets 1155, 1158 also may have a 360° range of rotation about shaft 1162.

Socket 1155 is secured to a member 1172, while similarly socket 1158 is secured to a member 1174, for example by the components being threadably coupled to each other. First portion 1172*a* preferably has outer threading and is associated with internal threading on socket 1155. Thus, the threadable association of first portion 1172*a* of member 1172 and socket 1155 permits socket 1155, particularly the internal rim defining opening 1155*a* thereof, to bear against ball 1156 with a user selected degree of tightness. A similar adjustment system may be used with respect to socket 1158 and member 1174.

Set screws 1176 also serve to prevent rotation and for example lock socket 1155 to member 1172, as well as lock socket 1158 to member 1174. In the exemplary embodiment, three sets screws 1176 are disposed about 120° apart from one another for each socket. For example, set screws 1176 are threadably associated with threaded holes in socket 1155 (as shown for example in FIG. 5K) and bear against portion 1172*c* of member 1172. A similar locking system may be used with respect to socket 1158 and member 1174.

A series of washers also may be provided for each ball and socket pair. For example, balls 1156, 1160 each may be disposed on a washer 1178*a*, 1178*b*. Washers 1178*a*, 1178*b* may have a concave, recessed portion 1179*a*, 1179*b* of generally spherical contour for receiving a ball 1156, 1160 and against which the ball may rotate. Washers 1178*a*, 1178*b* further may include a central protrusion 1180*a*, 1180*b*, respectively, for receiving another washer 1182*a*, 1182*b*. In turn, washers 1182*a*, 1182*b* may abut washers 1184*a*, 1184*b*. In the preferred exemplary embodiment, washers 1178*a*, 1178*b* are formed of aluminum and are provided to spread load respectively on balls 1156, 1160 to avoid point loading. Washers 1182*a*, 1182*b* may be formed for example of urethane and act as springs to maintain pressure. Finally, washers 1184*a*, 1184*b* may be formed for example of stainless steel and serve to spread load on washers 1182*a*, 1182*b*, respectively. Sockets 1155, 1158 are configured and dimensioned to retain the series of washers therein.

As can be seen in FIG. 5M, member 1174 may include a central hole 1186 for receiving a bolt 1186*a* and a recessed portion 1188 in which a nut 1188*a* may be threadably associated with bolt 1186*a*. Clamp 1154 may be secured to member 1174 with the combination of bolt 1186*a* and nut 1188*a*.

Although not shown in detail, member 1172 may be formed of a first portion 1172*a* coupled to a second portion 1172*b* for example with a centrally disposed bolt housed therein, although alternatively these portions may be integrally formed.

The ease of motion of sockets 1155, 1158 with respect to their balls 1156, 1160, respectively, may be adjusted, for example, based on the amount of threaded engagement of a socket with respect to its associated member 1172, 1174.

Holders 100, 300, 400, 500, 800, 900, 1000, 1100 and clamping system 550 preferably may be provided with a full cover sleeve drape. Devices 100, 300, 400, 500, 550, 800, 900, 1000, 1100 may be formed as a single use, pre-sterilized device, or as a sterilizable, re-usable device, or as a non-sterile re-usable device that is covered by a sterile drape/cover when required. Portions of devices 100, 300, 400, 500, 550, 800, 900, 1000, 1100 may be disposable.

In one exemplary, preferred embodiment, the holders of the present invention may be designed to create a minimum footprint or minimum interference within the surgical field and be easily sterilized or protected by a sterile cover. The holders preferably are long enough to reach from an attachment point on or proximate the location of a bedside railing to well past the skin entry port of a patient to allow for a full range of movement of the laparoscope, and to have enough pathway variability to clear other objects in the surgical field.

Some embodiments of holders may have several modes of operation. One mode may be free movement with little resistance at the free end. A second mode may be moderate resistance at the free end. This may be most useful when holding an endoscopic camera. In this instance, the resistance in this second mode preferably should be sufficient to maintain camera position in the absence of additional external force while at the same time being weak enough to allow a complete range of three-dimensional manipulation by the surgeon or assistant using only one hand without the need to adjust any locking or unlocking mechanism. A third mode may be fully locked with high resistance to movement at the free end. This mode may be particularly useful in the case where greater force may be required, such as retraction of an internal structure or organ. In this circumstance, an instrument connection other than, or in addition to the rotational joints disclosed herein, may be used.

As described above, coupling portion 302 of holder 300 and coupling portion 402 of holder 400 preferably are configured to be received in portion 82 of free handle 62 of articulating arm assembly 14. This articulating arm assembly now will be described.

Figure 6A:
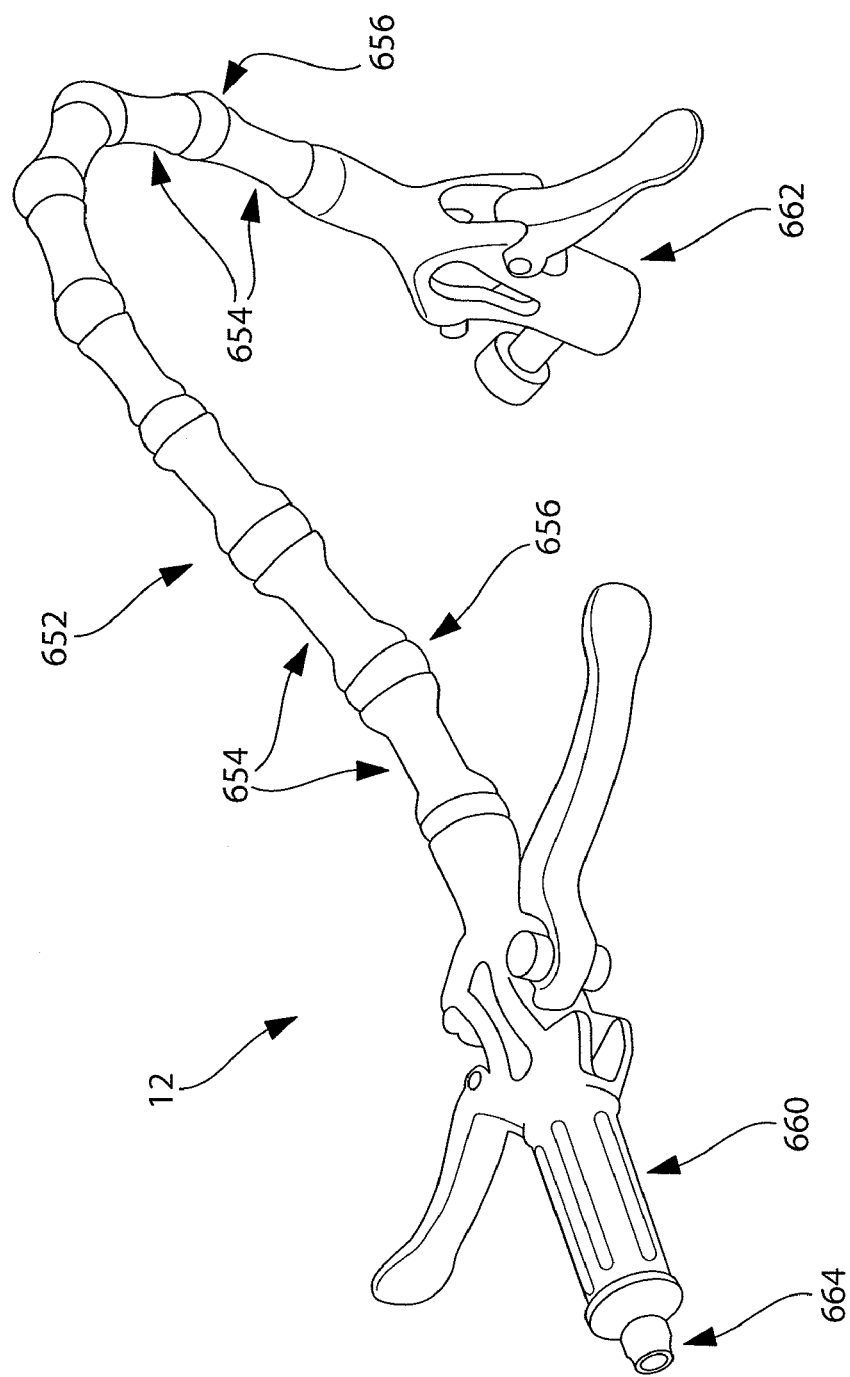
FIGS. 6A-6C show the curvilinear articulating arm assembly of FIG. 1, including (6A) a perspective view, (6B) a partial cross-sectional perspective view, and (6C) a partial side view.
Figure 6B:
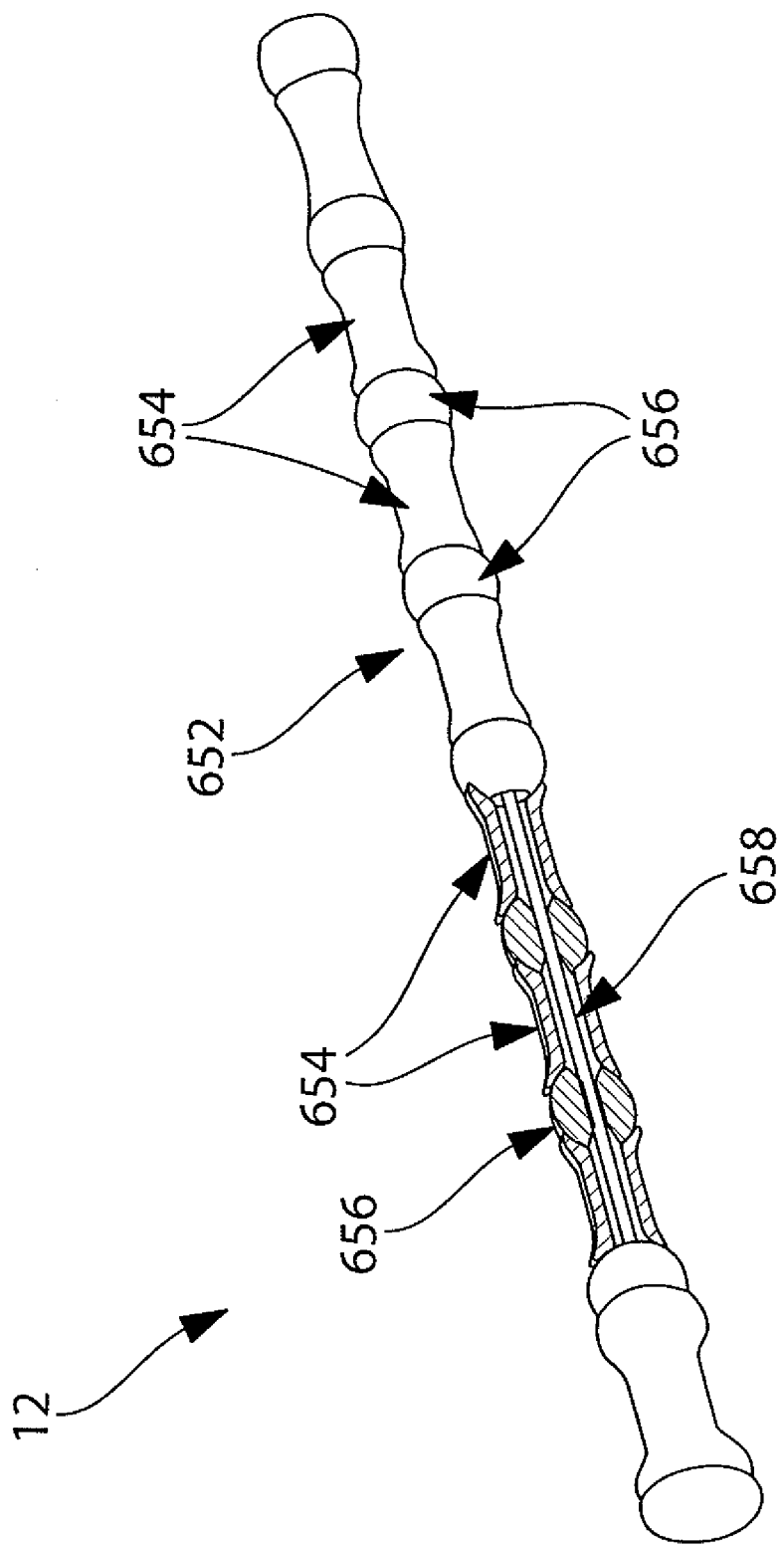
Figure 6C:
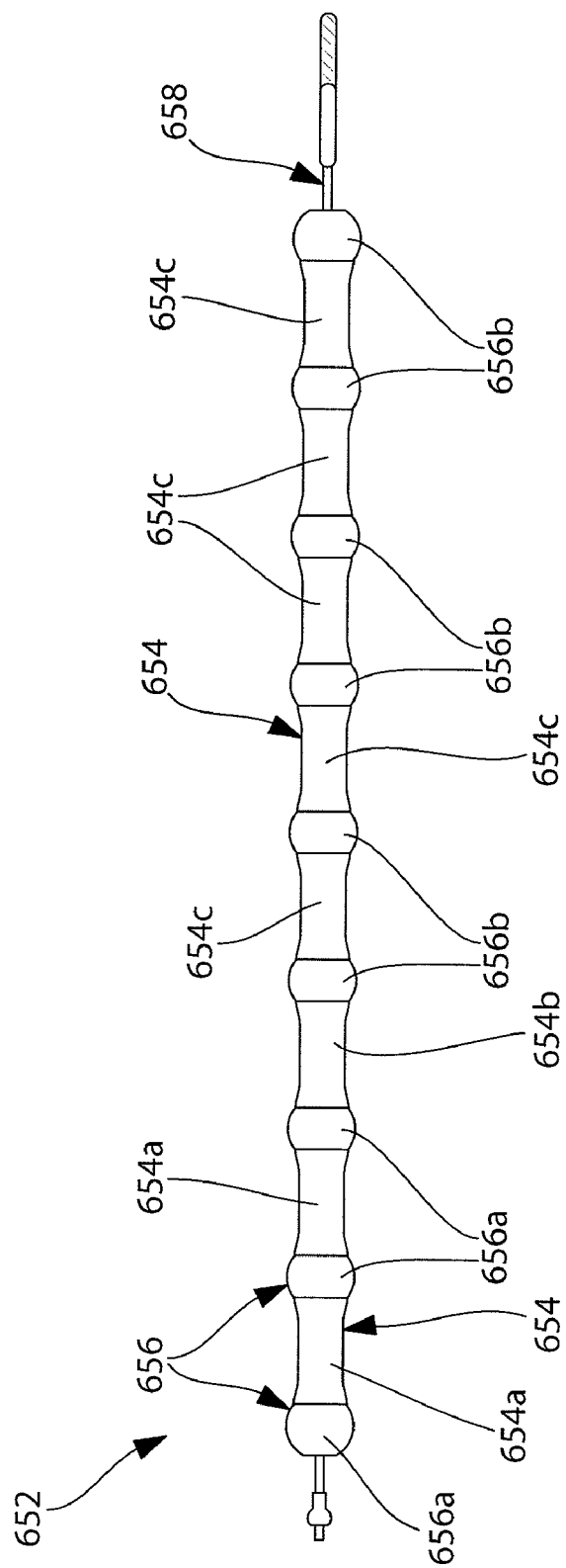
Figure 6D:
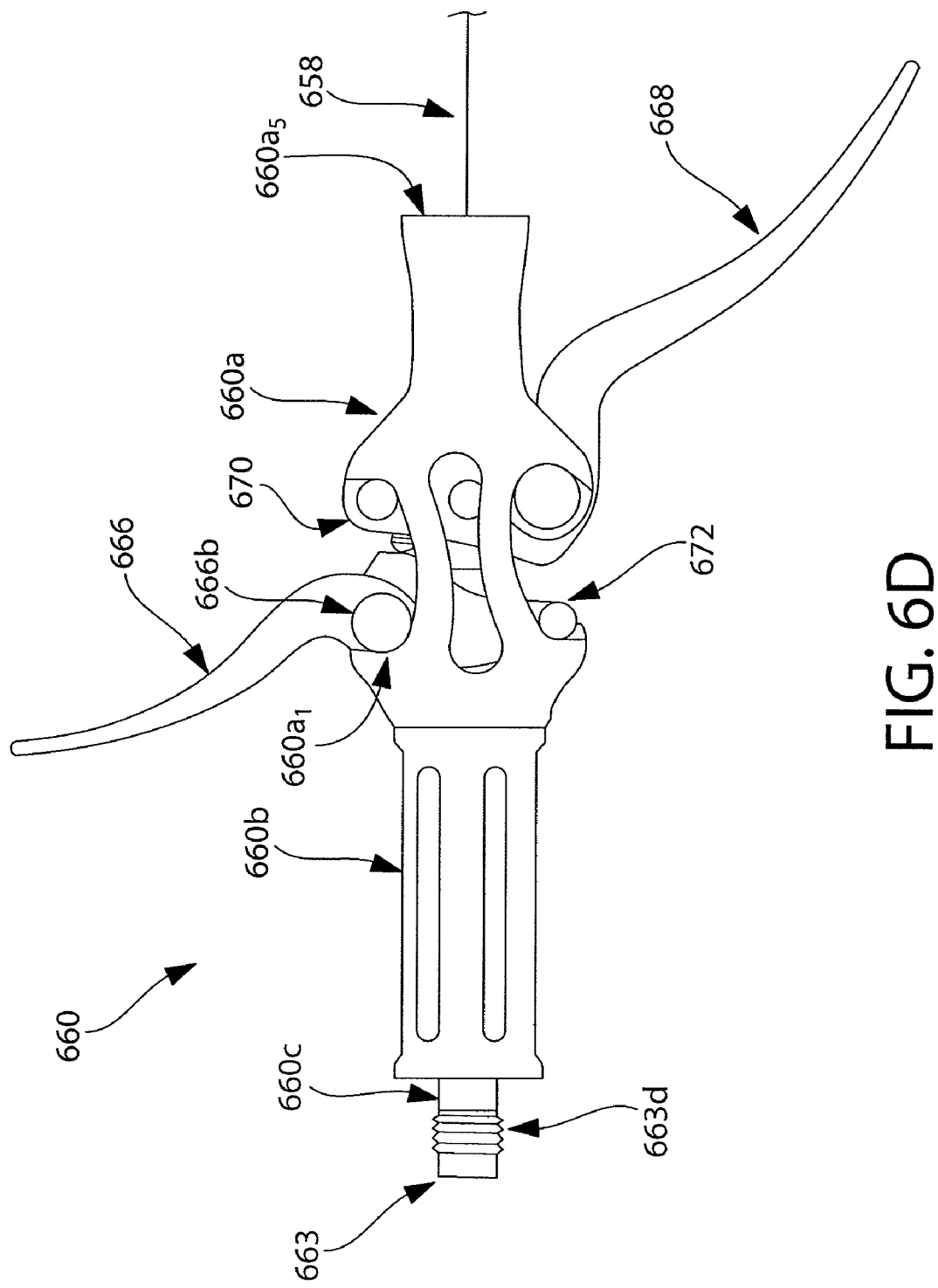
Figure 6E:
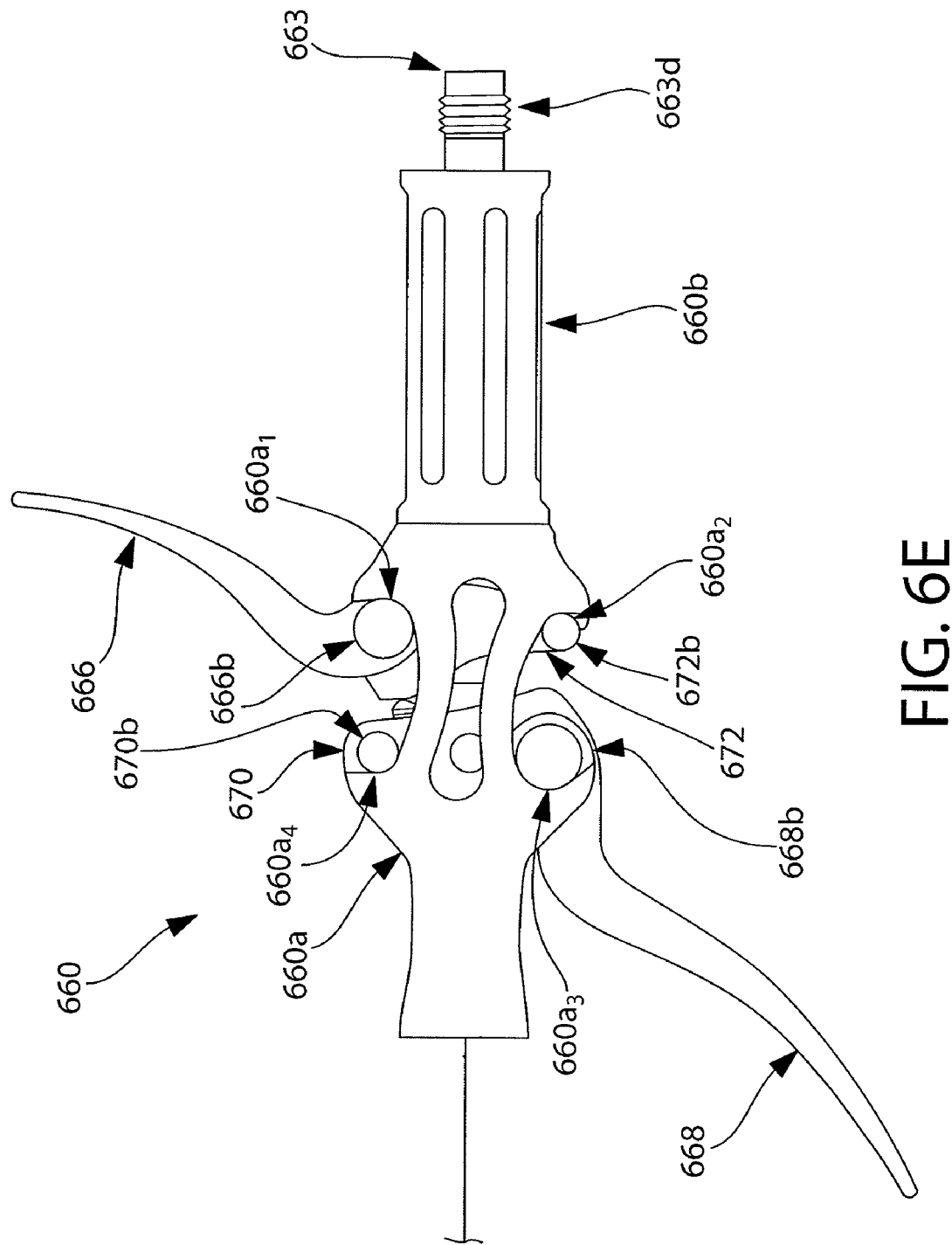

Turning to FIGS. 6A-6C, an exemplary preferred curvilinear articulating arm assembly 12 is shown for use with a laparoscopic instrument holder 14. Arm assembly includes a central arm 652 with a ball-sleeve arrangement that forms joints. In particular, central arm 652 includes a plurality of sleeves 654 with spherical balls 656 disposed therebetween thus forming ball and socket connections. In the exemplary embodiment shown in the figures, three balls 656*a* of a first size are disposed adjacent one another proximate one end of arm 652, while the remaining balls 656*b* are of a second size smaller than the first size. Sleeves 654*a* of a first size and sleeves 654*c* of a second size smaller than the first size are provided for accommodating balls 656*a*, 656*b*, respectively, while a transition sleeve 654*b* is provided intermediate sleeves 654*a*, 654*c* as shown for accommodating a ball 656*a* on one side and a ball 656*b* on the other side thereof. Sleeves 654 are configured and dimensioned to receive balls 656*a*, 656*b* at ends thereof and thus permit articulating of sleeves with respect to each other. A tensioning wire 658 runs generally centrally through sleeves 654 and balls 656, as will be further described shortly. Preferably, wire 658 is formed of metal. In an exemplary preferred embodiment, wire 658 is Type 302 stainless steel wire rope, 1×19 strand, 5/32 inch diameter, with a breaking strength of 3300 lb. (McMaster-Carr part number 3458T27). One exemplary operation of a wire tensioning mechanism is shown and described in U.S. Pat. No. 3,858,578 to Milo, which is expressly incorporated herein by reference thereto. Preferably, curvilinear articulating arm assembly 12 may move with six degrees of freedom.

In the exemplary preferred embodiment, three additional balls 656*a* and three additional sleeves 654*a* are provided to the arm assembly 12 shown in FIGS. 6A-6C, with arm assembly 12 having a fully extended (straightened) length of about 40 inches. End effector 14, for example, may add about 4 inches to the length of the arm assembly 12. In other embodiments, other desired lengths of the arm assembly 12 may be accomplished by changing the number of balls and sleeves. For example, without the three additional balls 656a and three additional sleeves 654a, arm assembly 12 may have a length of about 32 inches.

A base handle 660 is coupled to central arm 652 on a first end thereof; preferably adjacent a ball 656a. In addition, a free handle 662 is coupled to central arm 652 on a second end thereof, preferably adjacent a ball 656b.

In one preferred exemplary embodiment, a series of larger balls 656a is provided proximate base handle 660 to provide stability to curvilinear articulating arm assembly 12. If for example a user such as a surgeon orients assembly 12 by grasping it proximate free handle 662, substantial bending forces may be exerted on central arm 652 proximate base handle 660. Thus, the use of larger balls 656a proximate base handle 660 as compared to smaller balls 656b proximate free handle 662 provides a system with larger surface area balls near base handle 660 for additional resistance to rotational movement in that portion of central arm 652 and thus more stability. In alternate embodiments, more than two different sizes of balls 656 or more than two sets of sizes of balls 656 may be used, preferably increasing in size toward base handle 660. In one alternate embodiment, each of the balls 656 in central arm 652 is of increasingly larger size from free handle 662 to base handle 660. The use of only two sizes of balls 656 advantageously facilitates manufacture and construction of arm assembly 12 because of the need to only stock two sizes as compared to a larger number of sizes and concomitantly greater ease of construction because only two sizes need be assembled to form central arm 652. In yet another alternate embodiment, central arm 652 may be formed of balls 656 that all are the same size.

Turning to FIGS. 6D-6L, base handle 660 will be described. Base handle 660 includes a body portion 660a with levers 666, 668 pivotably associated therewith, as well as an extension 660b that turns screw coupling 663 and rotates in relation to and independent of body portion 660a. Base handle 660 further includes cam mechanisms 670, 672 as will be described. Portion 663b of coupling 663 preferably is noncircular and mechanically engages and is fixed to a like-shaped and sized non-circular opening in portion 660c of extension 660b so that rotation of extensions 660b as by gripping and turning by a user imparts like-rotation of coupling 663 for example for demountable coupling to clamp 16 and further coupling to a surgical table rail 18, as shown for example in FIG. 1. In the preferred exemplary embodiment, coupling 663 comprises a threaded portion 663d which may be threadably received in a threaded hole 16a disposed in clamp 16.

Coupling 663 is disposed proximate a first free end 664a of a stainless steel shaft 664 which extends therethrough and is provided with a head that abuts a shoulder disposed in end 663c of coupling 663. Preferably, rotation of coupling 663 is independent of rotation of shaft 664. Shaft 664 preferably extends through a hole in extension 660b.

Lever 666 is pivotably coupled to rocker arm 672 with a pin 666a that is disposed such that rotation of lever 666 results in eccentric movement of rocker arm 672. As shown for example in FIGS. 6D-6E, cylindrical projections 666b of lever 666 are received and rotate in arcuate cradle portions $660a_1$ of body portion 660a, while cylindrical projections 672b of rocker arm 672 are received and rotate in arcuate cradle portions $660a_2$ of body portion 660a. Rotation of lever 666 toward screw coupling 663 in direction K lifts pin 666a, and because rocker arm 672 rests on pin 666a, rocker arm 672 is rotated in direction L in an eccentric fashion.

Figure 6F:
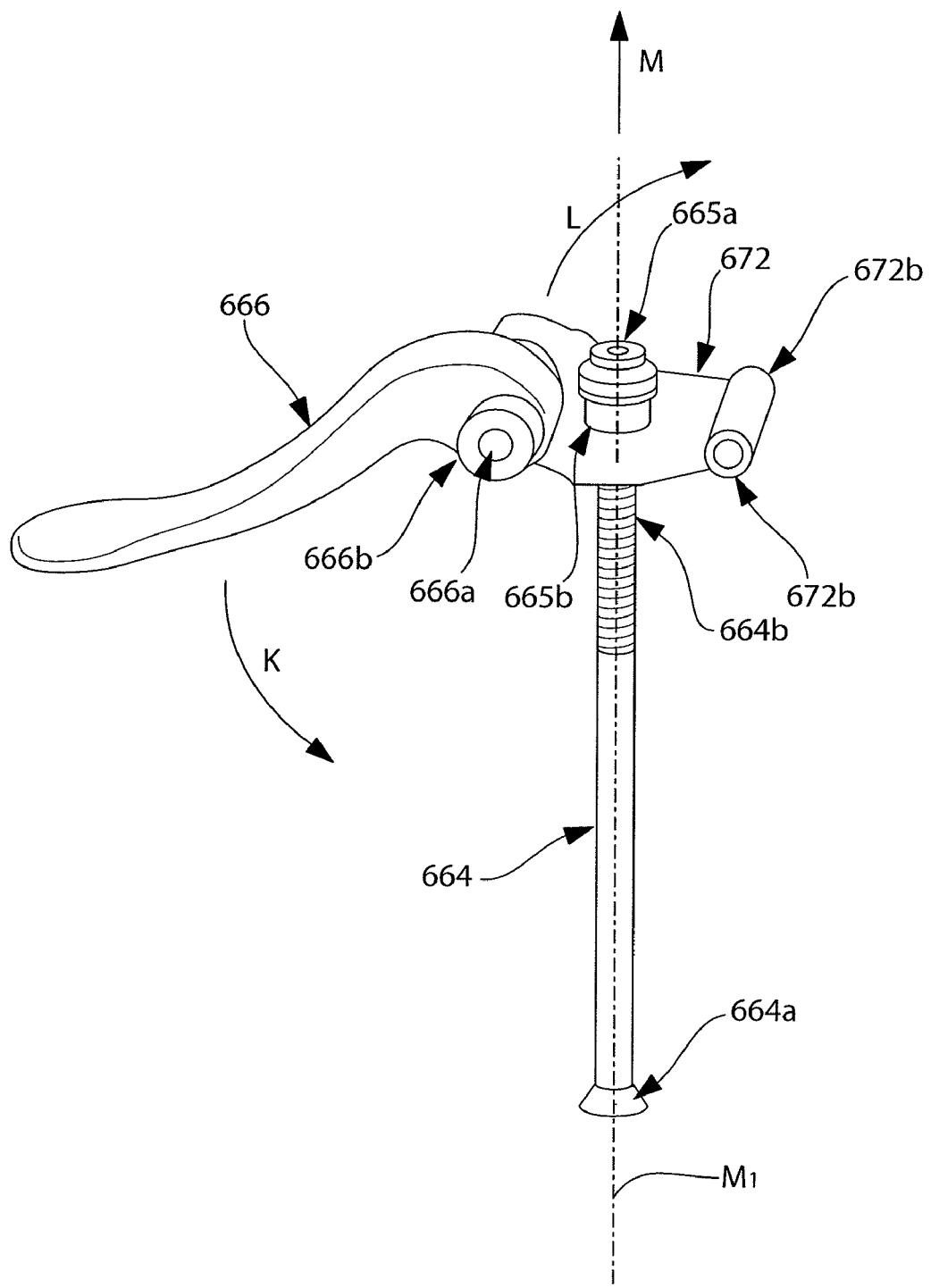
Figure 6G:
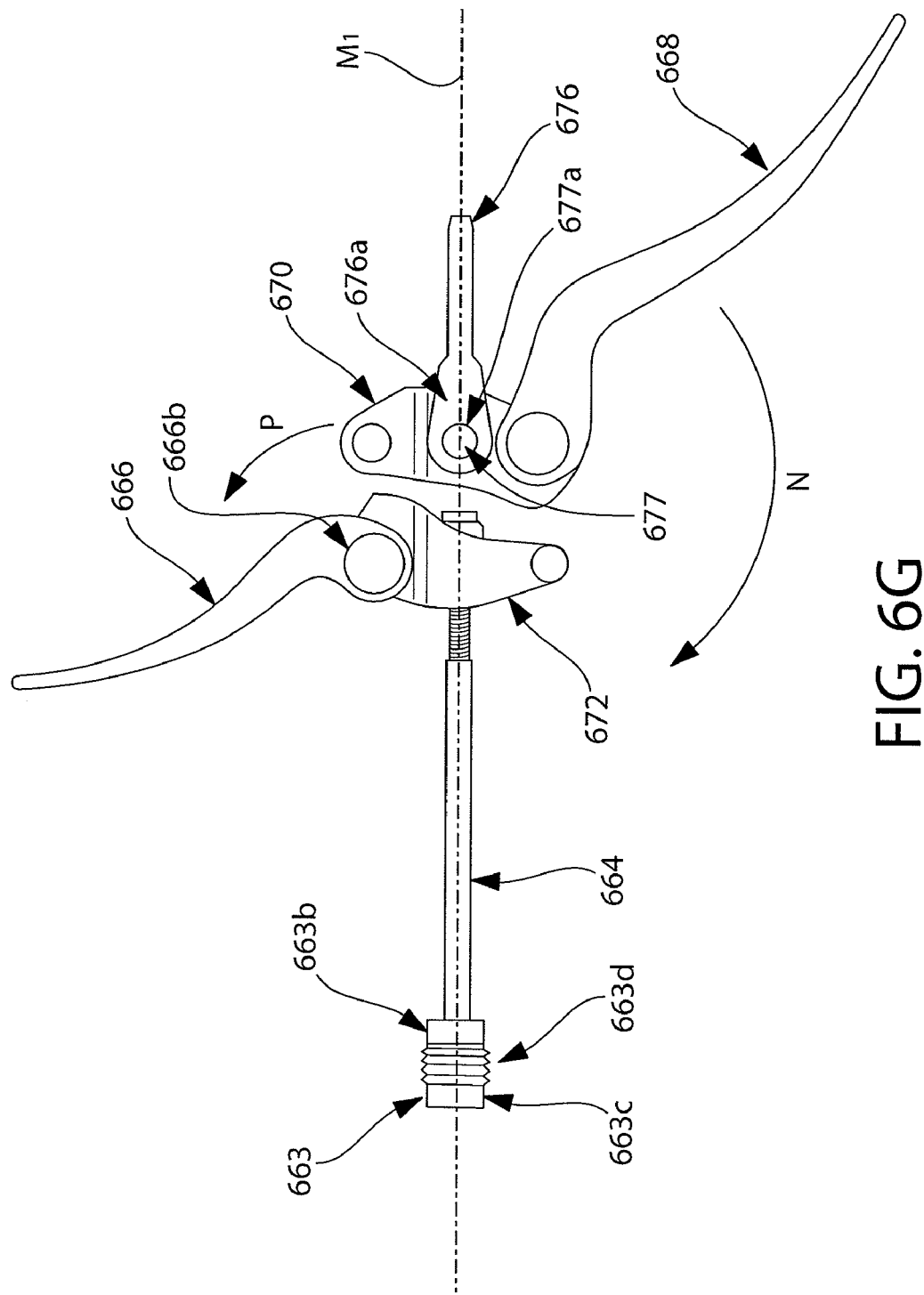
Figure 6H:
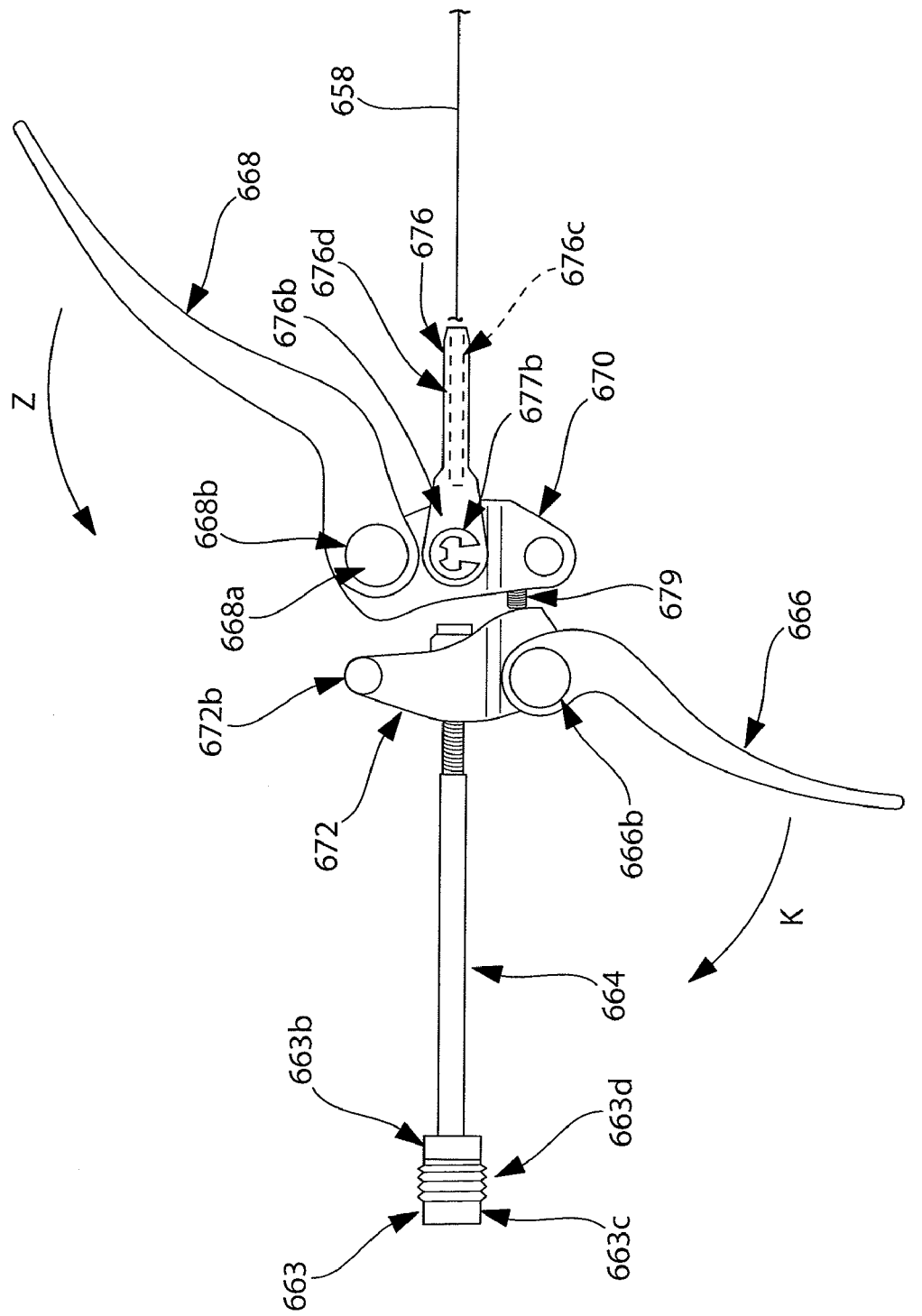
Figure 61:
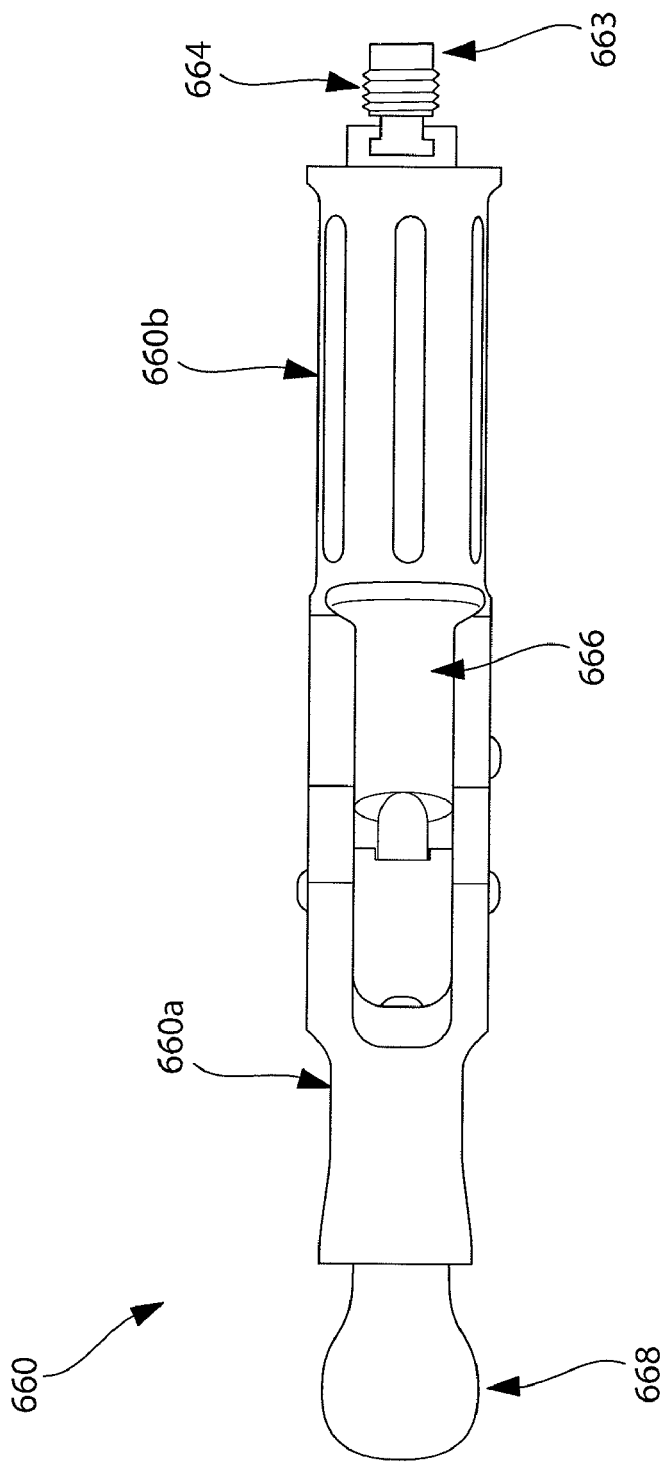
Figure 6J:
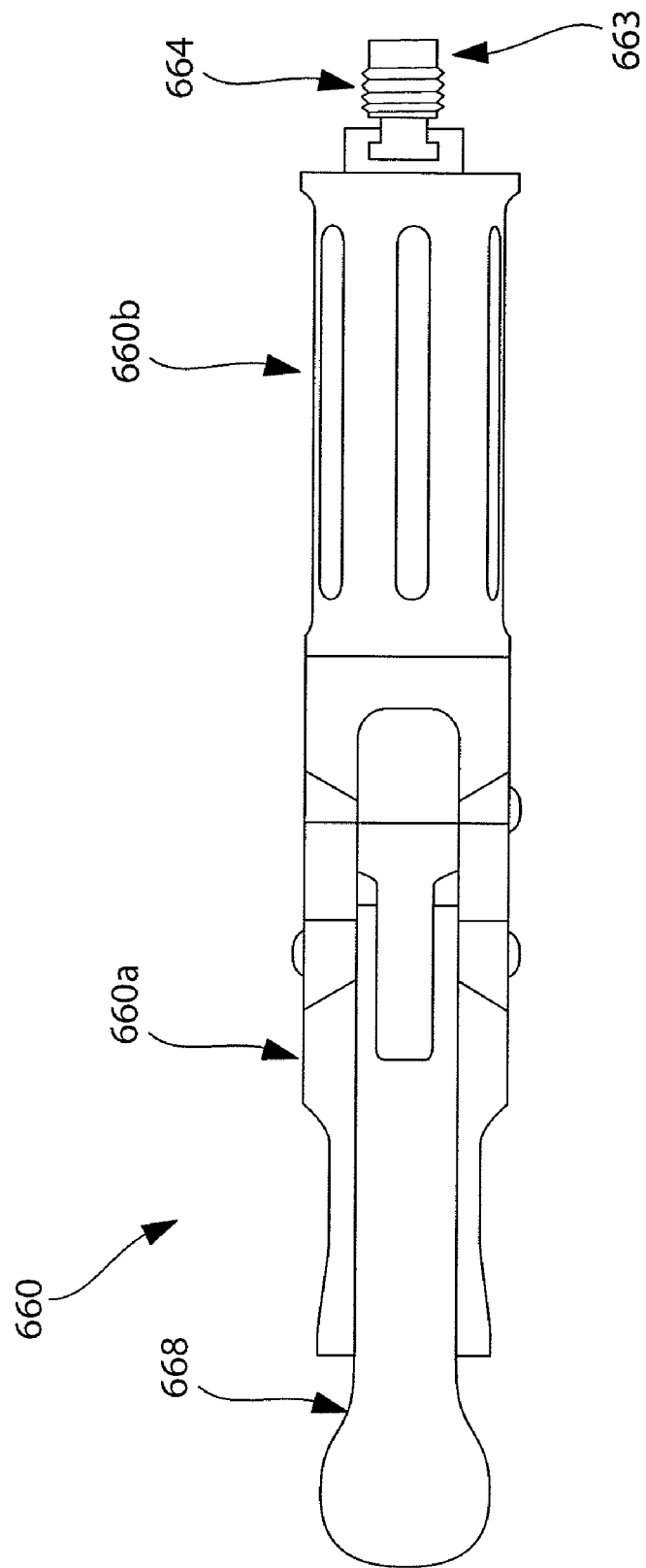
Figure 6K:
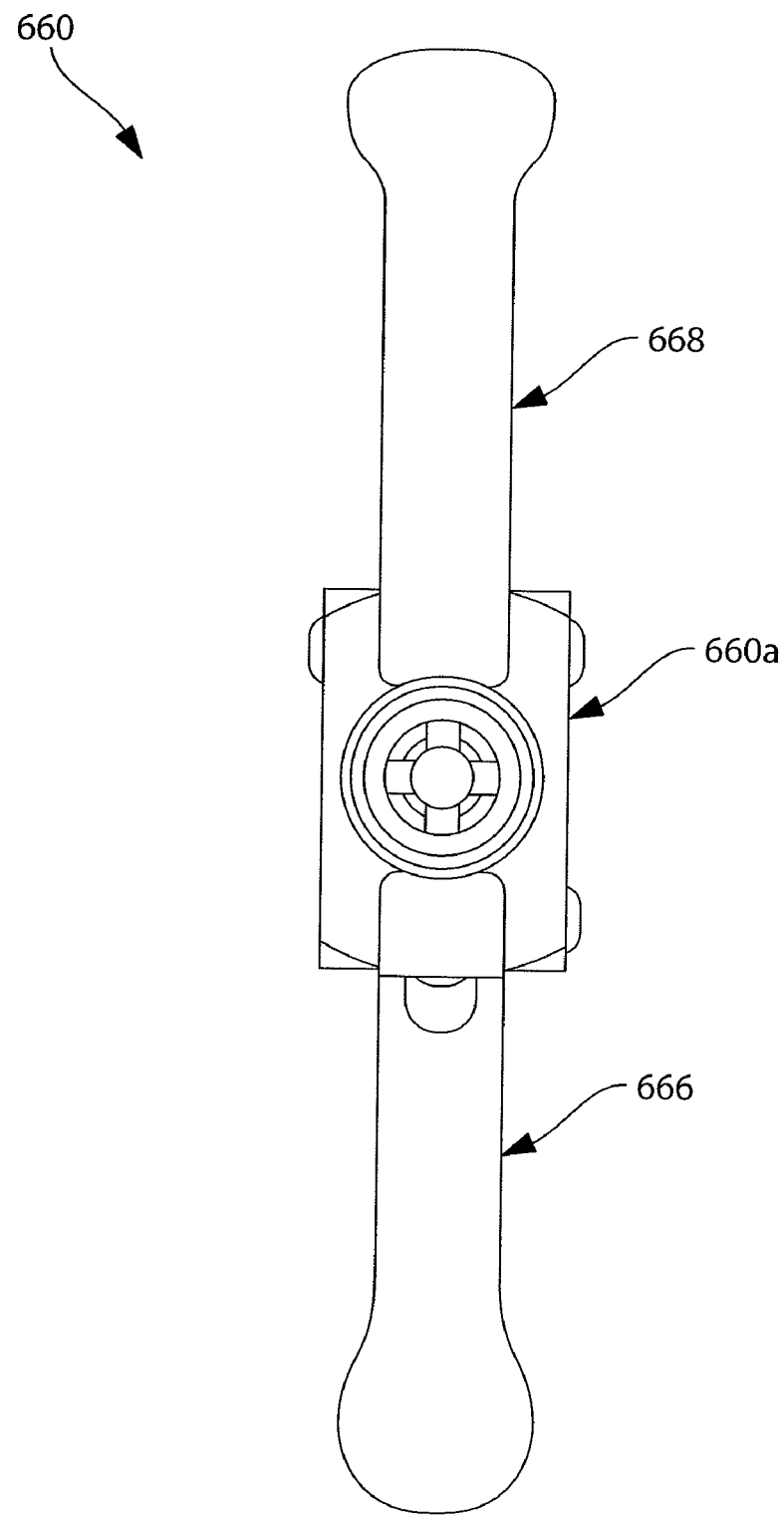
Figure 6L:
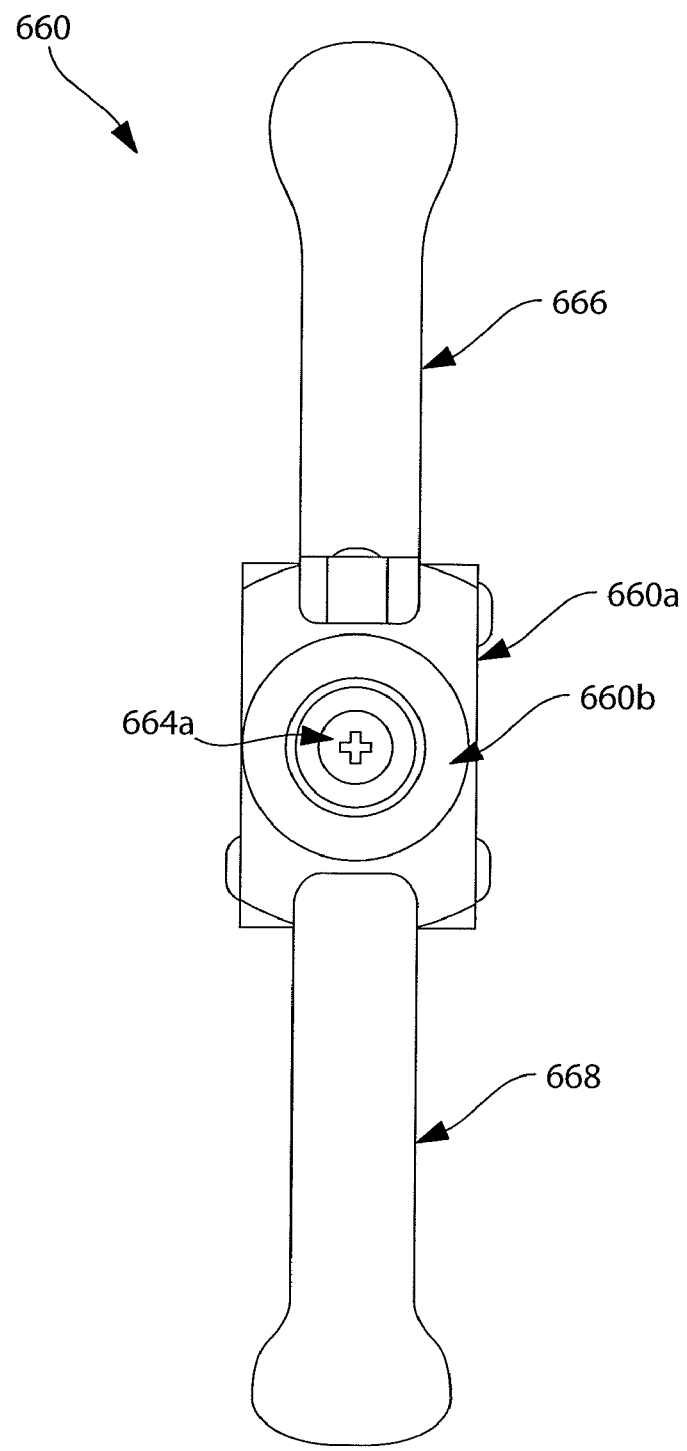

As seen particularly in FIG. 6F, shaft 664 includes a threaded portion 664b the free end of which is threadably associated with a nut 665a. Shaft 664 extends through a hole in rocker arm 672 and an unthreaded insert 665b with a hole therein which assists in guiding travel of rod 664 along the longitudinal axis thereof. Pivoting of lever 666 in direction K causes rotation of rocker arm 672, and with shaft 664 coupled to nut 665a and nut 665a abutting insert 665b, rod 664 is translated in direction M.

When coupling 663 is threaded into a like threaded hole by rotation of extension 660b, arm assembly 12 is relatively loosely coupled by the connection of coupling 663 to the hole. To firmly couple arm assembly 12, lever 666 may be pivoted in direction K so that threaded portion 663d of coupling 663 also moves in direction M and bears against the threads of the hole in which it is received. The leverage created by even slight movement of the threads against the threaded holes, on the order of tens of thousandths of an inch, creates a wedging effect that strongly locks arm assembly 12 to the hole.

Lever 668 of base handle 660 also is pivotably coupled to a rocker arm 670 with a pin 668a that is disposed such that rotation of lever 668 results in eccentric movement of rocker arm 670. As shown for example in FIGS. 6D-6H, cylindrical projections 668b of lever 668 are received and rotate in arcuate cradle portions $660a_3$ of body portion 660a, while cylindrical projections 670b of rocker arm 670 are received and rotate in arcuate cradle portions $660a_4$ of body portion 660a. Rotation of lever 668 toward screw coupling 663 in direction N lifts pin 668a, and because rocker arm 670 rests on pin 668a, rocker arm 670 is rotated in direction P in an eccentric fashion.

A forked member 676, which for example may be formed of stainless steel, is coupled to rocker 670 and includes substantially parallel prongs 676a, 676b which mate with side walls of rocker 670 as shown. Rocker 670 is pivotably associated with forked member 676, with a shaft 677 extending through aligned holes in prongs 676a, 676b and rocker 670. Shaft 677 may be provided with a head 677a and an external retaining ring 677b secured in a shaft groove proximate an end opposite head 677a to retain forked member 676 in association therewith and thus with rocker 670. An axial through hole 676c is provided in tubular portion 676d of forked member 676. Tensioning wire 658 is coupled to forked member 676 by inserting an end portion of wire 658 in hole 676c and swaging tubular portion 676d so that wire 658, which extends out of open end $660a_5$ of body portion 660a, is retained by compression within tubular portion 676d.

When lever 668 is rotated in direction N, shaft 676 translates along the longitudinal axis $M_1$ toward coupling 663 creating substantial tension in tensioning wire 658 such that movement of curvilinear articulating arm assembly 12 may be substantially resisted. In particular, actuation of second lever 668 may increase or decrease the tension in wire 658 as desired by acting on rocker arm 670. By increasing tension in wire 658, central arm 652 preferably becomes increasingly resistant to movement although central arm 652 preferably still may be moved through its full range of motion. Thus, a user may orient curvilinear articulating arm assembly 12 as desired, and then increase the tension of wire 658 so that the orientation of arm 652 is releasably fixed. Lever 668 preferably has an angular range of movement about pin 668a of up to about 180° to permit substantial tension to be generated in tensioning wire 658. Rockers 670, 672 preferably are associated with each other as with a spring plunger 679 extending from within one rocker 670 into a hole in the other rocker 672. Spring plunger for example may be a stainless steel spring plunger with a round Delrin nose, without a lock element, with ¼"-20 threading, and 3-13 lb. end force (McMaster-Carr part number 84765A33). Spring plunger 679 is used as shown because under the force of gravity, first lever 666 may otherwise tend to move toward a closed position with in the direction of arrow K. Instead, spring plunger 679 applies pressure to rocker arm 672 to set lever 666 to tend to a default open position in which shaft 664 has not otherwise been raised toward open end 660$a_5$ of body portion 660$a$.

In a preferred exemplary embodiment, rocker 670 moves with substantially greater eccentricity than rocker 672.

Clamp 16 for use with base handle 660 may be demountably attached to surgical table rail 18. As previously discussed, actuation of first lever 666 permits a user to apply a force on coupling 663 so that movement is resisted (e.g., in response to an 8 or 10 pound force applied to arm 652). In an alternate embodiment which will be further described later, screw coupling 664 as shown in FIG. 6A proximate base handle 660 of arm assembly 12 may be threadably associated with a threaded hole in another support surface.

Figure 6M:
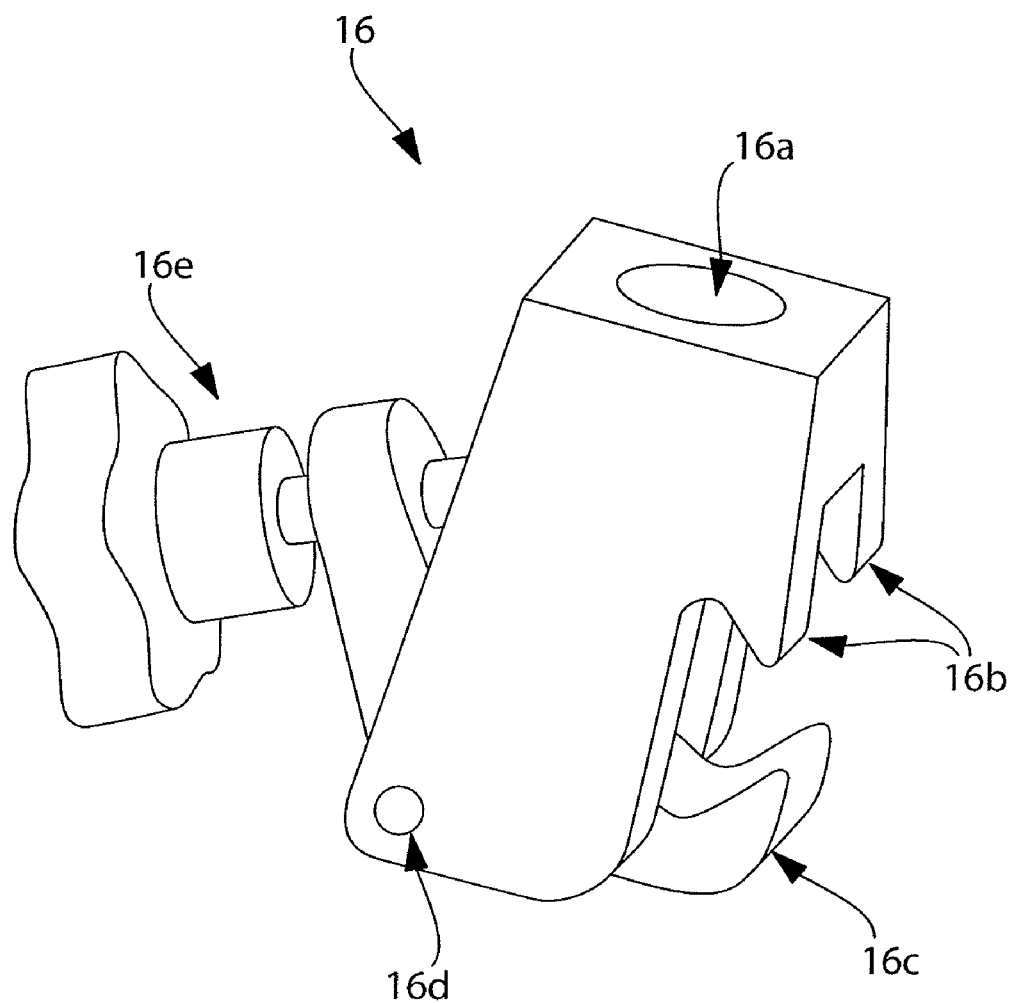
FIG. 6M) shows a perspective view of a rail clamp for use with the present invention.
Figure 6N:
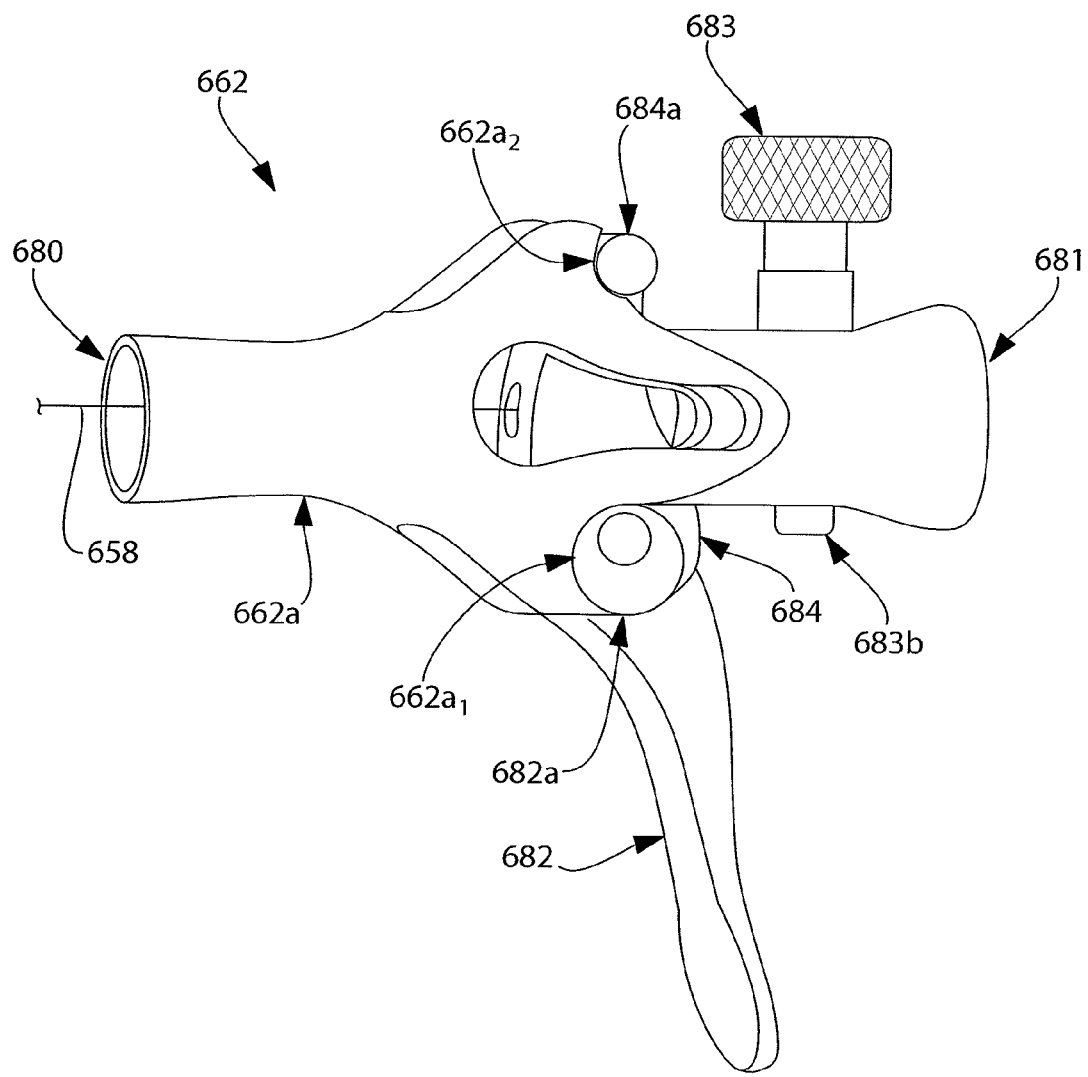
FIGS. 6N-6T show the free handle of FIG. 1, including (6N) a first side perspective view showing a portion of a tensioning wire therewith, (6O) a second side perspective view, (6P) a partial perspective view showing a first set of components thereof, (6Q) a front perspective view, (6R) a back perspective view, (6S) a top perspective view, and (6T) a bottom perspective view.
Figure 6O:
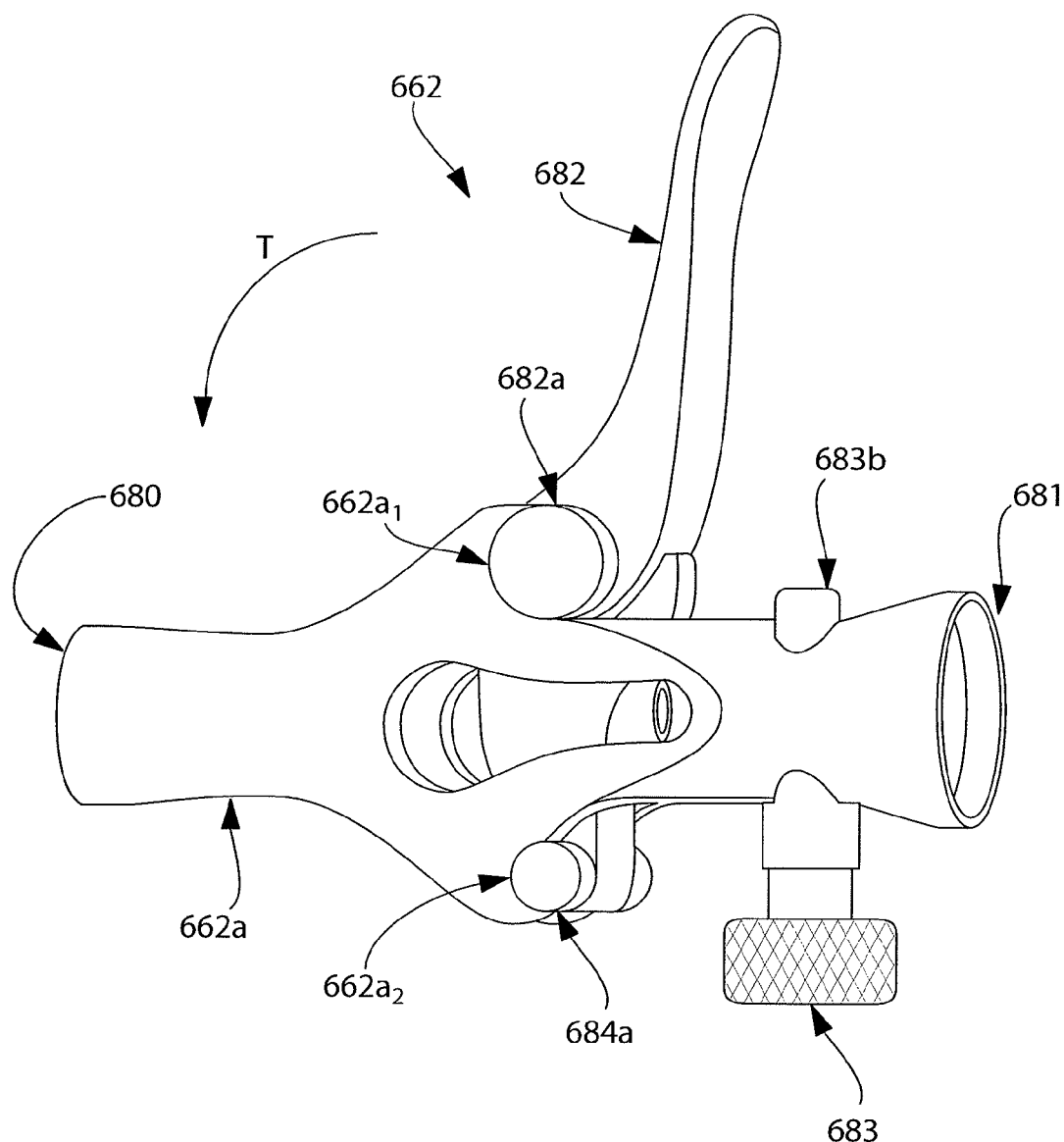
Figure 6P:
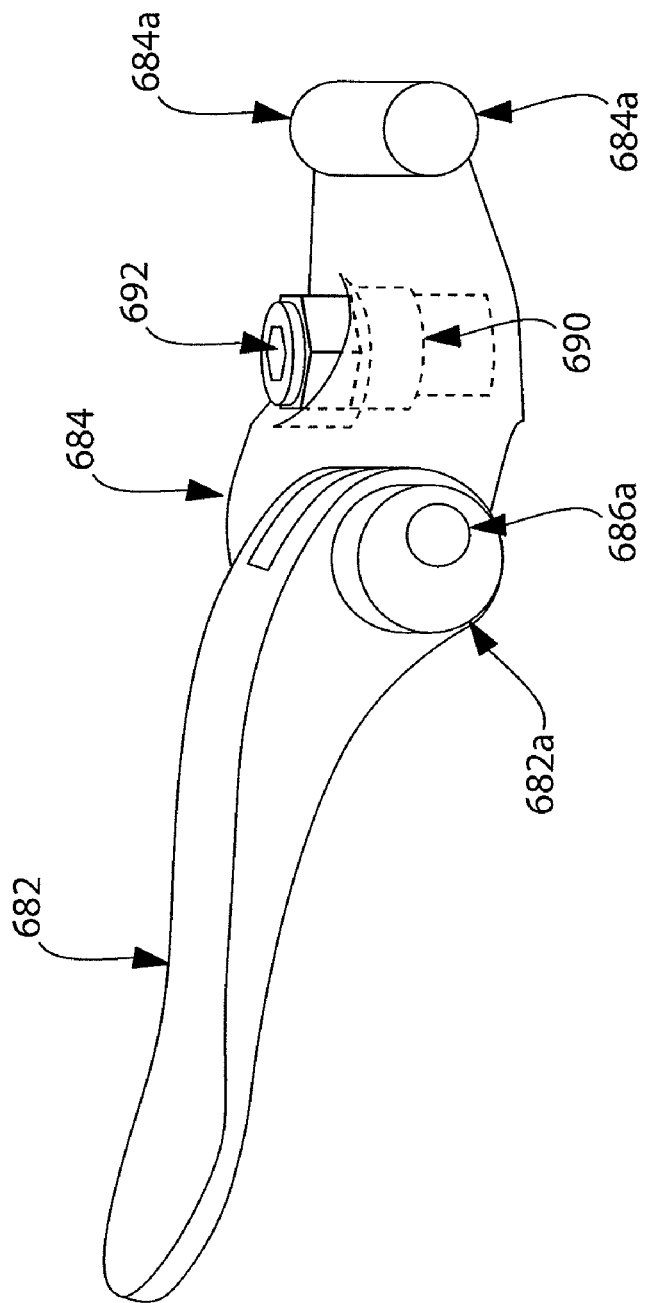
Figure 6Q:
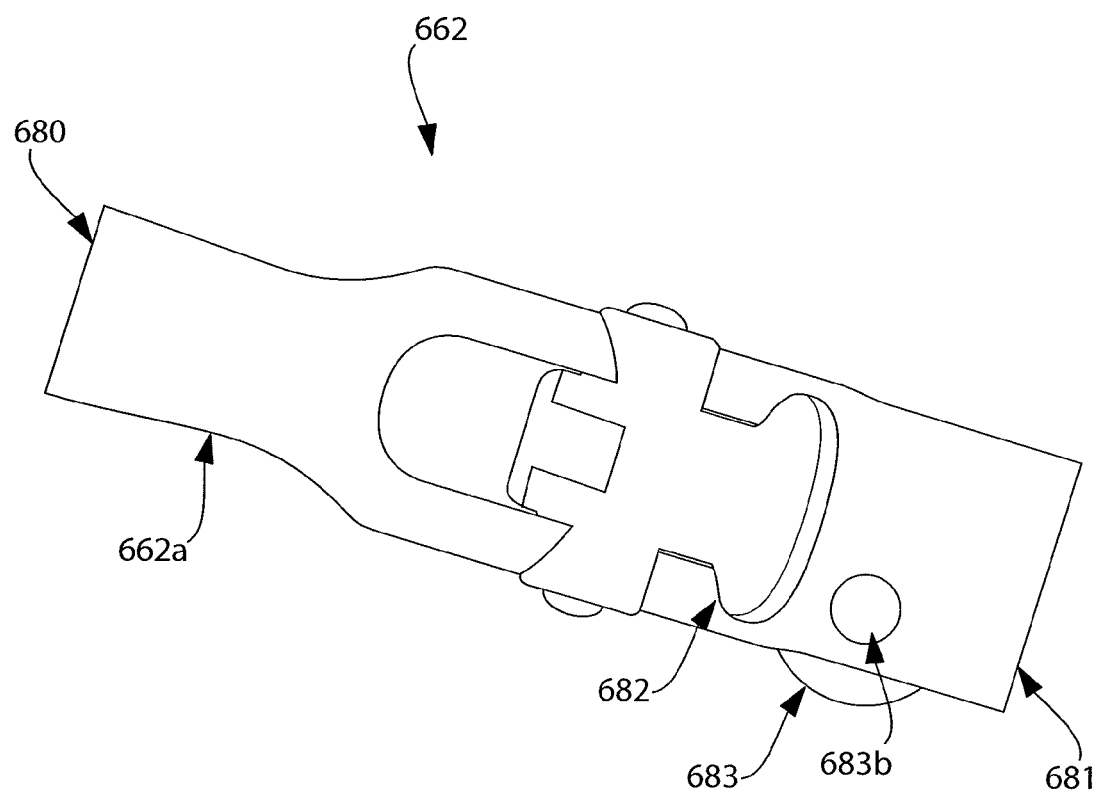
Figure 6R:
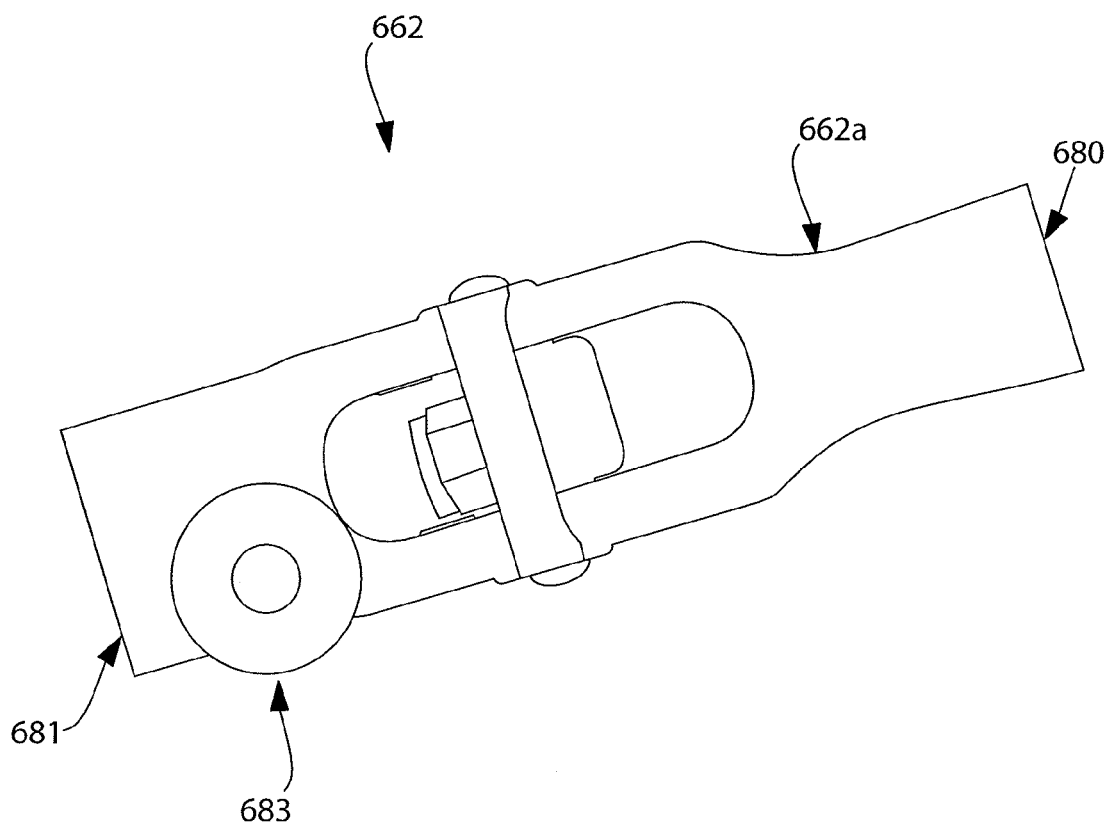
Figure 6S:
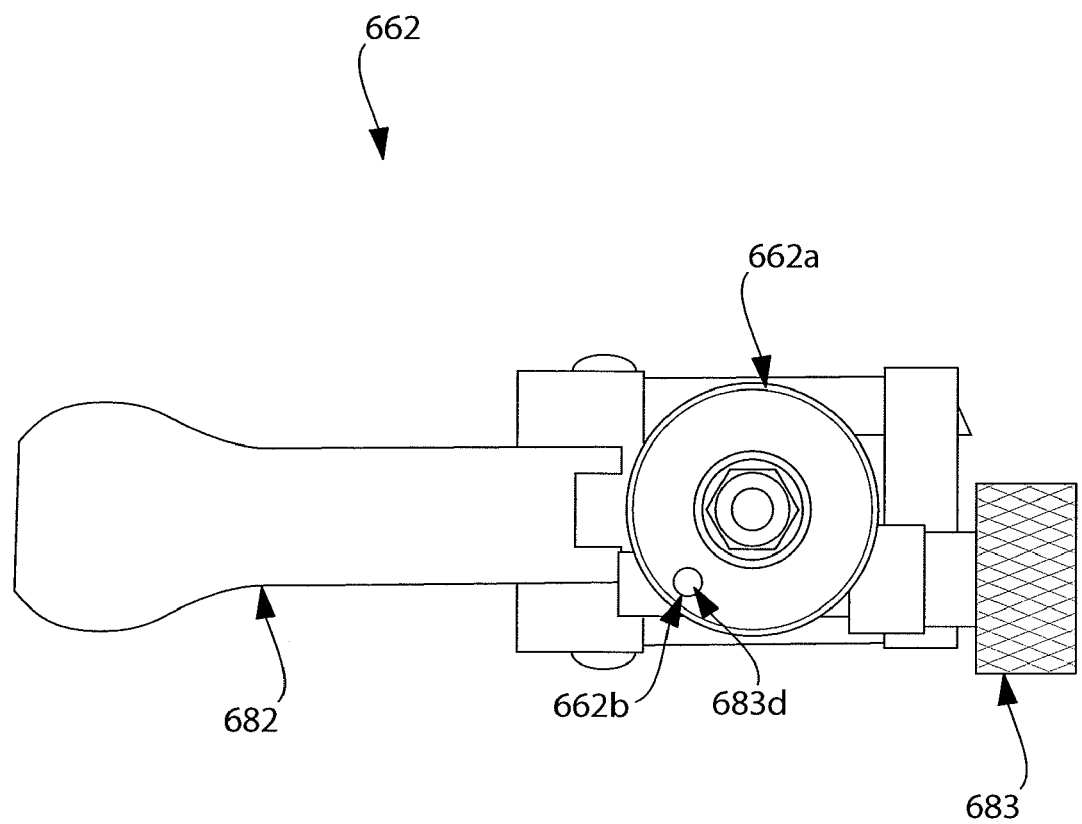
Figure 6T:
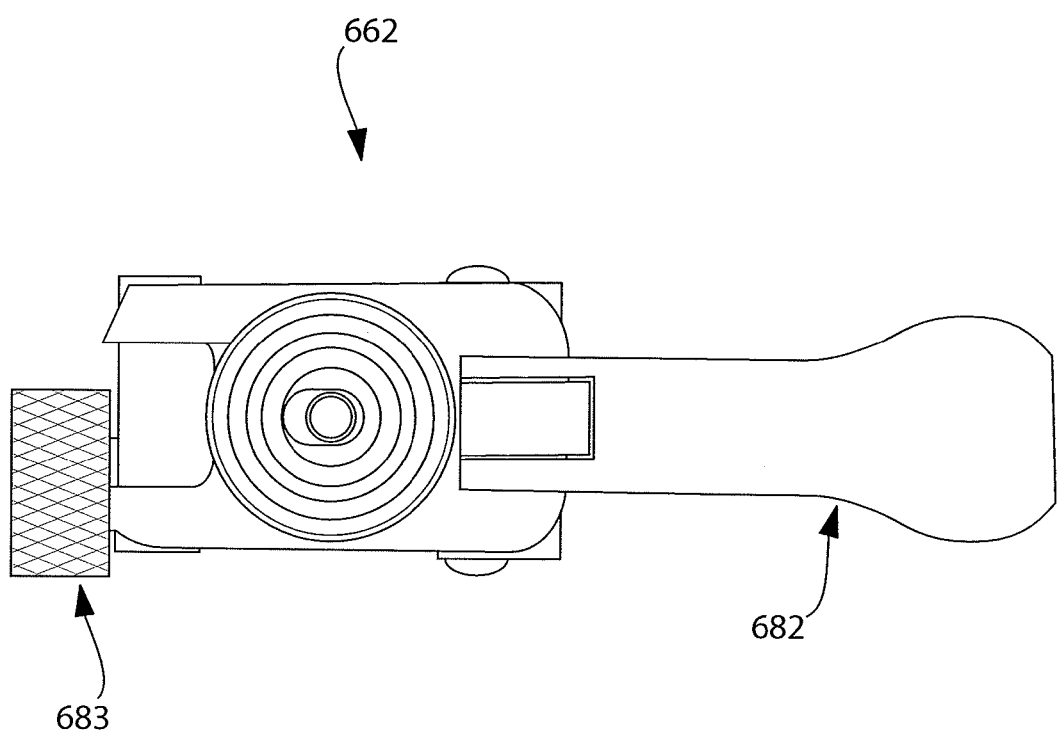

A preferred exemplary embodiment of clamp 16 is shown in FIG. 6M. Clamp 16 includes a threaded hole 16$a$ for threadably receiving threaded portion 664 of base handle 660. In addition, clamp 16 includes fixed jaw portion 16$b$ and movable jaw portion 16$c$ which is pivotable about axle 16$d$ and lockable in place using screw mechanism 16$e$ to firmly couple clamp 16 to a rail 18 secured between jaw portions 16$b$, 16$c$.

Next turning to FIGS. 6N-6U, free handle 662 will be described. Free handle 662 includes a wire receiving portion 680 and an end effector receiving portion 681. In particular, wire receiving portion 680 preferably is configured to receive a ball 656$b$ therein, along with an end portion of wire 658. As described previously with respect to base handle 660, a pivotable lever 682 is associated with free handle 662 and preferably is coupled to tensioning wire 658 so that actuation of lever 682 may increase or decrease the tension in wire 658 as desired by acting on rocker arm 684. By increasing tension in wire 658, central arm 652 preferably becomes less flexible. Thus, a user may orient curvilinear articulating arm assembly 12 as desired, and then increase the tension of wire 658 so that the orientation of arm 652 is releasably fixed. Free handle 662 has a body portion 662$a$, and lever 682 is rotatable with respect thereto. An interface lock 683 also is rotatably associated with body portion 662$a$ proximate end effector receiving portion 681, as will be described shortly.

Lever 682 is pivotably coupled to rocker arm 684 with a pin 686$a$ that is disposed such that rotation of lever 682 results in eccentric movement of rocker arm 684. Cylindrical projections 682$a$ of lever 682 are received and rotate in arcuate cradle portions 662$a_1$ of body portion 662$a$, while cylindrical projections 684$a$ of rocker arm 684 are received and rotate in arcuate cradle portions 662$a_2$ of body portion 662$a$. Rotation of lever 682 toward wire receiving portion 680 in direction T lifts pin 686$a$, and because rocker arm 684 rests on pin 686$a$, rocker arm 684 is rotated in direction U in an eccentric fashion.

Rocker arm 684 includes a hole in which a self-aligning setup washer 690 (a two-piece washer with one portion that rocks in another portion) is disposed. Setup washer 690 for example may be an 18-8 stainless steel self-aligning setup washer, ¼ inch in size, ¹⁷⁄₆₄ inch inner diameter, ½ inch outer diameter, and 0.250 inch to 0.281 inch thick (McMaster-Carr part number 91944A028). A nut 692 also may abut setup washer 690 on the flat upper surface thereof and rock thereon.

A threaded stud (not shown) may be swaged to the end of tensioning wire 658 opposite the end attached to forked member 676, thus coupling wire 658 to the threaded stud by compression. The threaded stud may in turn be threadably associated with nut 692. Wire 658 is provided with suitable length to span from forked member 676 to nut 692.

Pivoting of lever 682 in direction T causes rotation of rocker arm 684, and with tensioning wire 658 coupled to nut 692 and nut 692 abutting insert 690, tension in wire 658 may be increased. In particular, actuation of lever 682 may increase or decrease the tension in wire 658 as desired. By increasing tension in wire 658, central arm 652 preferably becomes increasingly resistant to movement although central arm 652 preferably still may be moved through its full range of motion. Thus, a user may orient curvilinear articulating arm assembly 12 as desired, and then increase the tension of wire 658 so that the orientation of arm 652 is releasably fixed. Lever 668 preferably has an angular range of movement about pin 686$a$ of up to about 90° to permit tension to be generated in tensioning wire 658.

In the preferred exemplary embodiment, actuation of lever 682 free handle 662 permits initial tensioning of central arm 652 while still permitting restricted movement. And, actuation of lever 668 of base handle 660 permits substantially greater tensioning of central arm 652 while also still permitting restricted movement thereof. Advantageously, with tension created in wire 658 of central arm 652 to restrict movement thereof, the orientation of lever 668 such as with respect to a patient still may readily be reset or adjusted before lever 666 in base handle 660 is actuated to create sufficient force to prevent rotation of threaded portion 663$d$ of coupling 663 in the hole in which it is received.

Figure 6U:
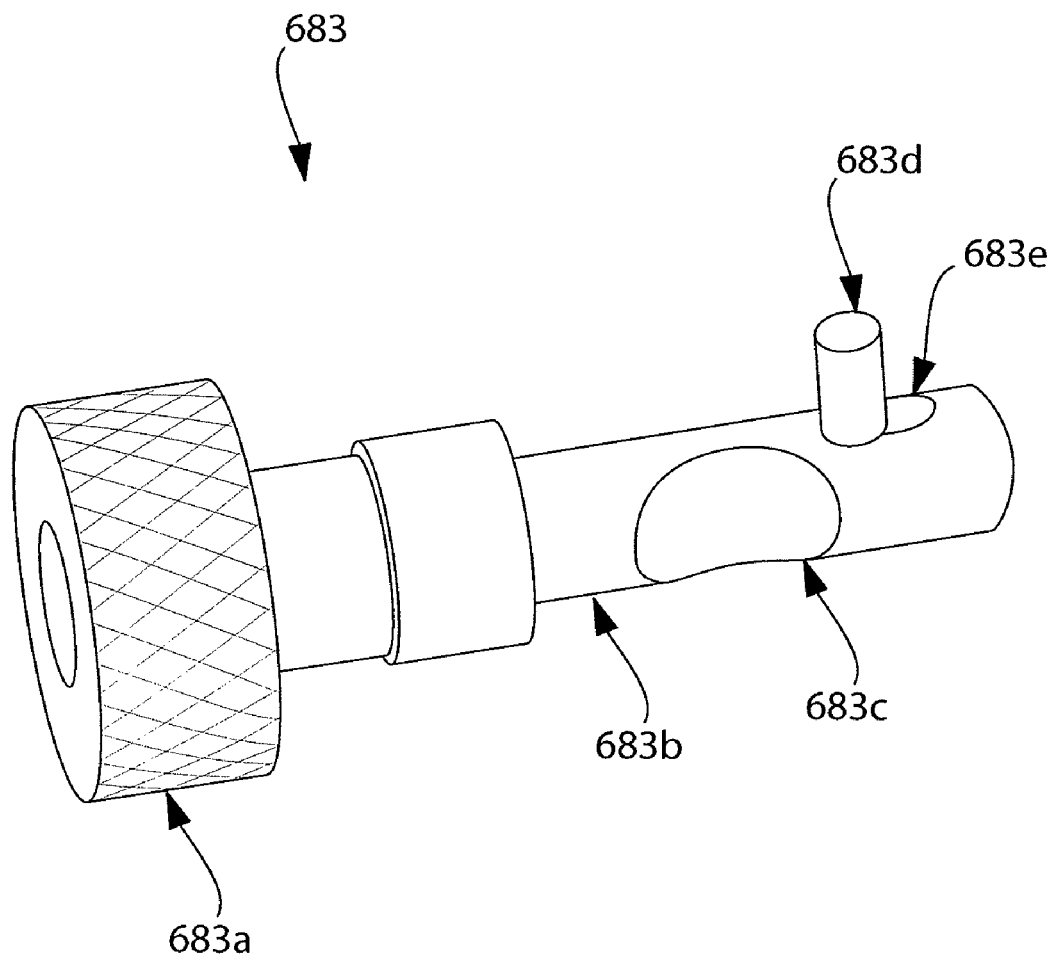
FIG. 6U shows a side perspective view of the interface lock of the free handle of FIGS. 6N-6T.

As shown in FIG. 6U, interface lock 683 includes a knurled knob portion 683$a$ and a cylindrical post 683$b$ that is provided with an arcuate cutout 683$c$. Interface lock 683 is coupled to body portion 662$a$ with set screw 683$d$ which is threadably received in a threaded hole 662$b$ in body portion 662$a$. Set screw 683$d$ is further received in a slot 683$e$ in post 683$b$ to lock post 683$b$ in a position with arcuate cutout 683$c$ oriented to be movable along the longitudinal axis of cylindrical post 683$b$. Cylindrical post 683$b$ may be disposed in a disengaged position in which the axial position of post 683$b$ is such that arcuate cutout 683$c$ generally follows the inner cylindrical contour of end effector receiving portion 681. Also, cylindrical post 683$b$ may be disposed in an engaged position in which the axial position of post 683$b$ is such that a portion of cylindrical post 683$b$ other than arcuate cutout 683$c$ extends past the inner cylindrical contour of end effector receiving portion 681 toward the central longitudinal axis of end effector receiving portion 681.

In use, in order for example to couple articulating arm assembly 12 to an end effector such as a holder 100, by capturing post 102 of holder 100 in end effector receiving portion 681 of free handle 662, post 102 is inserted therein while interface lock 683 is disposed in the aforementioned disengaged position. While lock 683 is in the disengaged position, post 102 may freely rotate about the central axis of receiving portion 681. Once a desired orientation is set, lock 683 may be translated along the major axis defined by slot 683$a$ so that a portion of cylindrical post 683$b$ of lock 683 is disposed in an engaged position and bears against post 102. Such interference between post 102 of holder 100 and post 683$b$ of lock 683 provides sufficient pressure so that post 102 will remain fixed in rotational position and translation along the longitudinal axis thereof against the inner cylindrical contour of end effector receiving portion 681.

In one method of conducting a laparoscopic procedure according to the present invention, a curvilinear articulating arm assembly 12 with base attachment 16 is releasably secured to a surgical table rail 18. Holder system 100 is demountably coupled to the free end of arm assembly 12 at free handle 662, and a laparoscope is releasably retained in holder system 100 by locking it in the slot defined between face 122f and clamping portion 114, with the laparoscope being frictionally held in the slot in the desired rotational orientation. By articulating the lever 682 at the free end to a locked position, arm assembly 12 will hold position when left alone but can be easily repositioned with one hand without having to loosen or unclamp any other mechanisms. In this mode, arm assembly 12 should have sufficient resistance to hold the laparoscope in position absent other external forces, much like a gooseneck lamp. If locking lever 668 near the base of arm assembly 12 is also locked then arm assembly 12 will hold position against a much greater force, but this lever 668 will then have to be released when ready movement of the arm/scope combination is required.

Preferably, the two rotating joints of holder 100 have complete freedom of motion and cannot be locked, and the scope is engaged by the slot defined between face 122f and clamping portion 114 that opens via a syringe-like spring mechanism as previously described. Free movement of the scope is allowed by the freely rotating joints of holder 100 that respond to user-selected positioning of articulating arm assembly 12 while the scope is in the skin port of the patient.

In normal use, knob 124 preferably is backed off so that the spring loading of movable clamping jaws 122 operates freely and the scope may be engaged and disengaged quickly at will.

Once curvilinear articulating arm assembly 12 is fixed in position, the geometry of the swivel joints of holder 100 in combination with the curvilinear articulating arm assembly 12 and the laparoscope passing through a skin port is designed to result in reliable position holding for the scope, yet allow complete freedom of movement by manual repositioning. There is no need to adjust any locking or tensioning mechanisms because of the geometry of the setup and the resistance provided by the arm in its "gooseneck lamp" mode.

In some methods, gross movements of the scope may be accomplished by grabbing the articulating arm assembly 12 proximate the swivel joints and reorient the device from that gripping point. For smaller movements, it is possible to simply grab and torque the scope itself.

In one method of use, curvilinear articulating arm assembly 12 is closely contoured to the patient (approximately parallel to the skin) to minimize interference and clutter, and with the holder such as holder 800 extended nearby the endoscopic camera port. The position of arm assembly 12 is checked for suitable working range near the planned port site. The optimum attachment point for the base of the arm assembly 12 for example on a surgical bed railing is determined after the patient is positioned and asleep and before the next preparation phase. Arm assembly 12 may be oriented out of the way for prepping and draping. An arm drape may be placed after the skin prep but before the final large procedure drape is placed. A separate skirt/sheet drape may be clipped around the base after the large drape is placed. Arm assembly 12 may be contoured to the patient and brought adjacent to the camera port. The scope may be engaged working through the drape for example by pinching open the spring loaded clamp of holder 800 and simply invaginating the cover with the scope into the slot. The cover preferably is tough and stretchy and withstands repeated engage/disengage cycles and scope rotation.

Each of the holder systems described herein may be used in accordance with the aforementioned methods, regardless of spring-loading of the clamping arrangements.

Also, although an exemplary curvilinear articulating arm assembly is described herein, it should be understood that other preferably, curvilinear articulating arm assemblies instead may be used which preferably provide six degrees of freedom of movement and permit relatively rigid positioning such as described herein.

In some embodiments of the present invention, an instrument holder system such as system 10 may be coupled to a patient support other than a rail of a table. For example, referring next to FIG. 7, an exemplary support system 710 according to the present invention is shown with a variety of components coupled thereto. Support system 710 includes a tray 712, curvilinear articulating arm assemblies 12, 716 having respective end effectors 100, 720, an IV pole 722, an arm board 724, and rail assemblies 726, 728. A variety of end effectors may be demountably attached for example to articulating arm assembly 716 to assist a technician or practitioner with a medical/imaging procedure or provide other features useful with respect to a patient. End effector 720, for example, is configured as a self-centering abdominal probe bracket.

Figure 7:
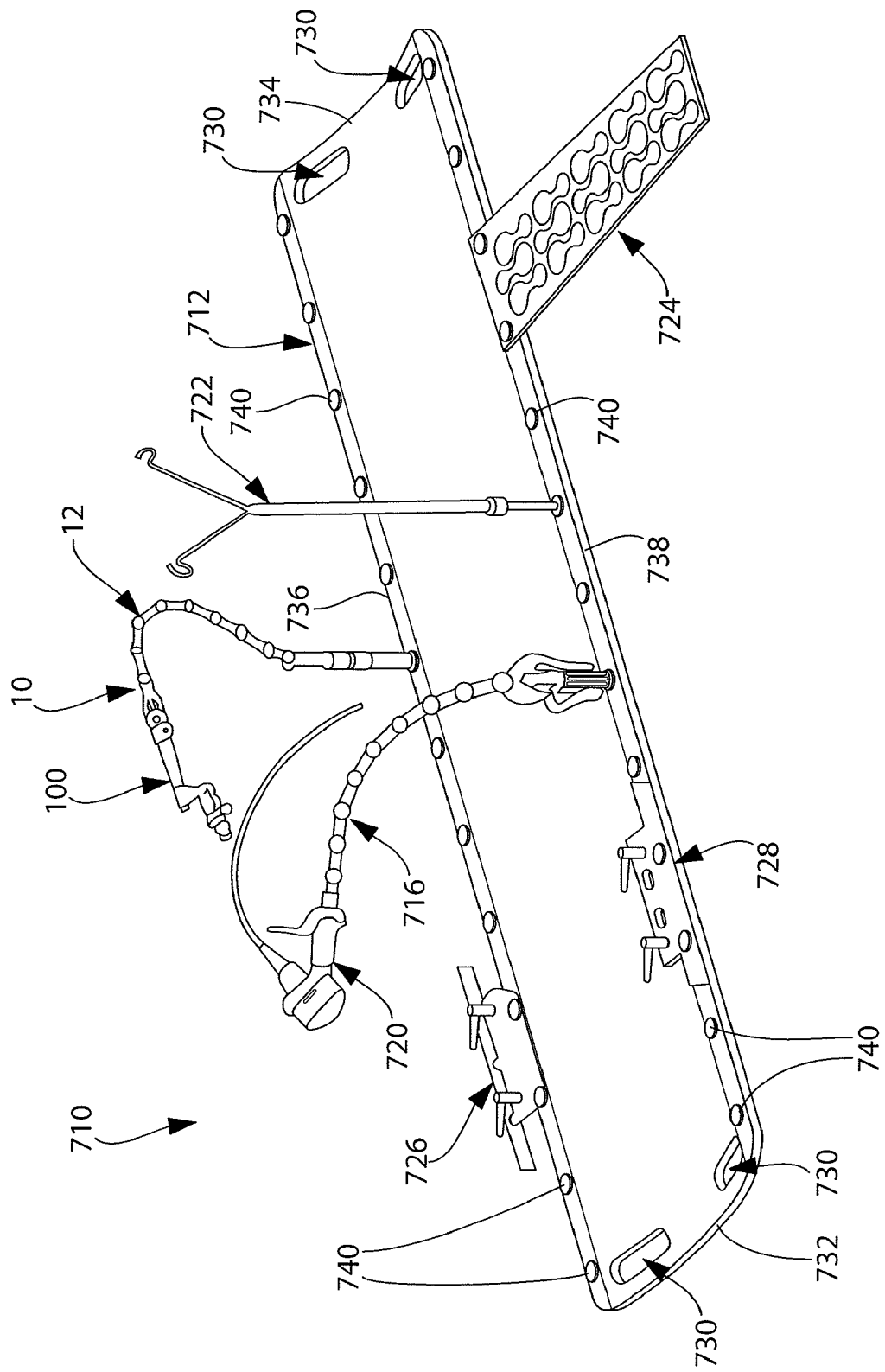
FIG. 7 shows a perspective view of a support system according to the present invention.

In one preferred exemplary embodiment, tray 712 may include two pairs of hold regions 730, each pair being disposed proximate a free cranial end 732 or free caudal end 734 of tray 712. In alternate embodiments, other numbers of hold regions 730 may be provided such as two or more, and hold regions 730 may be provided in other regions of tray 712 such as intermediate ends 732, 734 proximate sides 736, 738. Hold regions 730 may be configured as hand holds, or alternatively may be configured to receive strapping so that tray 712 may be releasably coupled to another object such as an ambulance stretcher, hospital bed, operating room table, or imaging scanner table. In some embodiments, handles may be coupled to tray 712. As also shown in FIG. 7, attachment regions 740 are provided proximate sides 736, 738 for demountably coupling components as previously described to tray 712, as will be further described below. In the exemplary preferred embodiment, tray 712 is provided with thirteen attachment regions 740, although in alternate embodiments another number of regions 740 may be provided such as at least one or tray 712 may be provided with a surgical rail or track permitting substantial freedom of coupling of components along the length thereof.

Figure 8A:
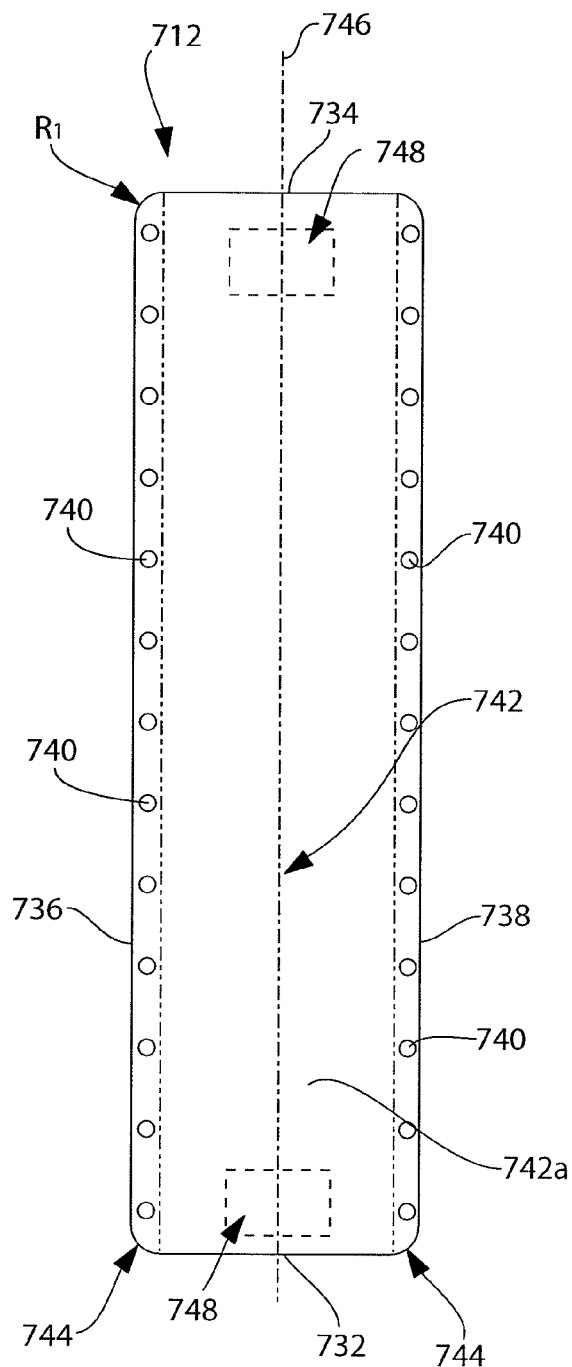
FIGS. 8A-8C show the tray of FIG. 7, including (8A) a top view, (8B) a cross-section taken perpendicular to the central axis of the tray, and (8C) a partial cross-section showing detail taken at VIC.
Figure 8B:
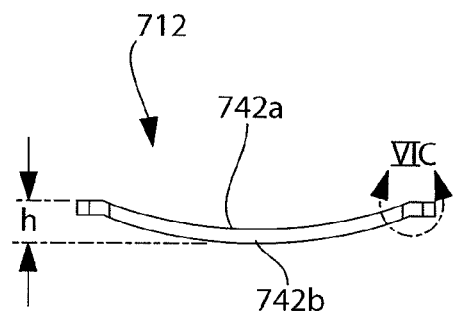
Figure 8C:
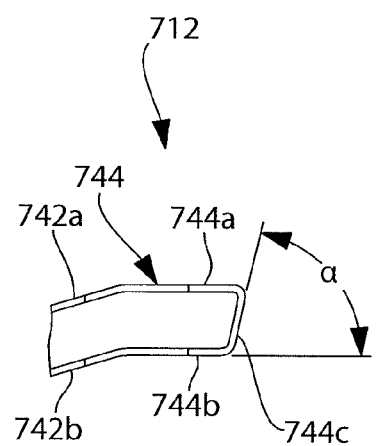

Turning to FIGS. 8A-8C, additional features of tray 712 are shown. Although hand hold regions 730 are not included in the figure, such regions may be provided as shown in FIG. 7. Attachment regions 740 are provided in spaced arrangement along the perimeter of tray 712. Preferably, tray 712 includes a central arcuate portion 742 disposed between outer ledge portions 744. Preferably, regions 740 are provided on outer ledge portions 744. Central arcuate portion 742 preferably has an upper concave surface 742a for receiving a patient and optionally a cushion (not shown) for the patient to rest against, and optionally includes a lower convex surface 742b. Preferably, outer ledge portions 744 include upper and lower surfaces 744a, 744b connected by a sidewall 744c at an angle α with respect to surface 744b. In a preferred exemplary embodiment, sidewall 744c is disposed at an angle α between about 60° and about 100°, more preferably between about 70° and about 90°, and most preferably at about 80°.

In a preferred exemplary embodiment, tray 712 is formed of natural finish carbon fiber, R-51 foam core, and phenolic. Attenuation preferably is less than 1 mm Al equivalency. Thus, tray 712 is radiolucent and suitable for use with computed axial tomography (CT) scanners. In other embodiments, tray 712 is formed of a material suitable for use with magnetic resonance imaging (MR) scanners. In addition, tray 712 preferably supports a load of 900 lbs. evenly distributed along centerline 746, about which tray 712 may be substantially symmetric as shown. Indicia 748 optionally may be provided, as shown for example proximate ends 732, 734. The indicia may for example indicate preferred orientation of tray 712 with respect to a patient lying thereon.

In the preferred exemplary embodiment, attachment regions 740 on each side of tray 712 are evenly spaced from each other by about 6 inches between centers thereof. To accommodate patients and equipment attached to tray 12, in one preferred embodiment tray 712 has a length of about 78 inches, a width of about 21 inches, a generally uniform thickness of about 0.9 inch, and a height h of about 2.5 inches. Corners may be provided with a radius $R_1$ of about 2 inches. In the preferred exemplary embodiment, attachment regions 740 preferably accommodate threaded inserts, which may be formed of aluminum.

In some embodiments, tray 712 is sized to hold an adult patient, and may be between about 180 cm and about 200 cm long. However, it will be appreciated that longer and shorter trays may be provided. In order to accommodate an adult patient, tray 712 may support an overall weight capacity of at least about 200 pounds, and preferably at least about 300 pounds. However, if a tray 712 is sized for use with a pediatric patient, tray 712 may only accommodate weights that do not exceed 200 pounds, and more preferably do not exceed 100 pounds.

Although the surface of portion 742 of tray 712 is substantially smooth in the preferred exemplary embodiment, in alternate embodiments the surface may be textured to provide additional resistance to motion of objects and/or a patient placed thereon.

Tray 712 thus is suitable for use in multiple environments, and thus may "move" with the patient from one environment (e.g., ambulance) to the next (e.g., CT scanner) without removing a patient supported thereon.

Figure 9A:
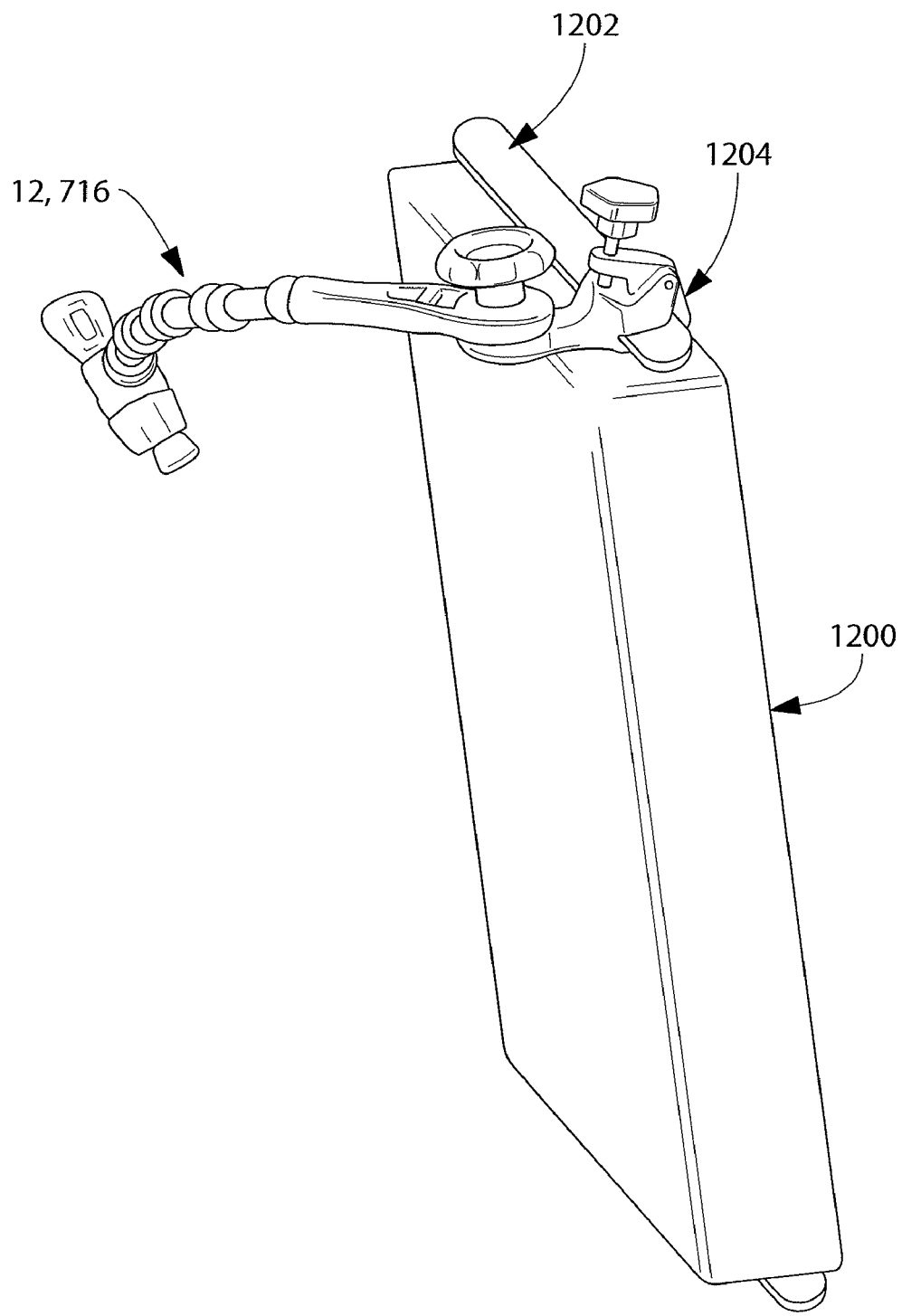
FIGS. 9A-9B show another embodiment of a support system including (9A) a perspective view of a curvilinear articulating arm assembly coupled to a patient support surface along a rail thereof and (9B) a perspective view of a clamp for use in coupling the assembly to a member such as a rail.
Figure 9B:
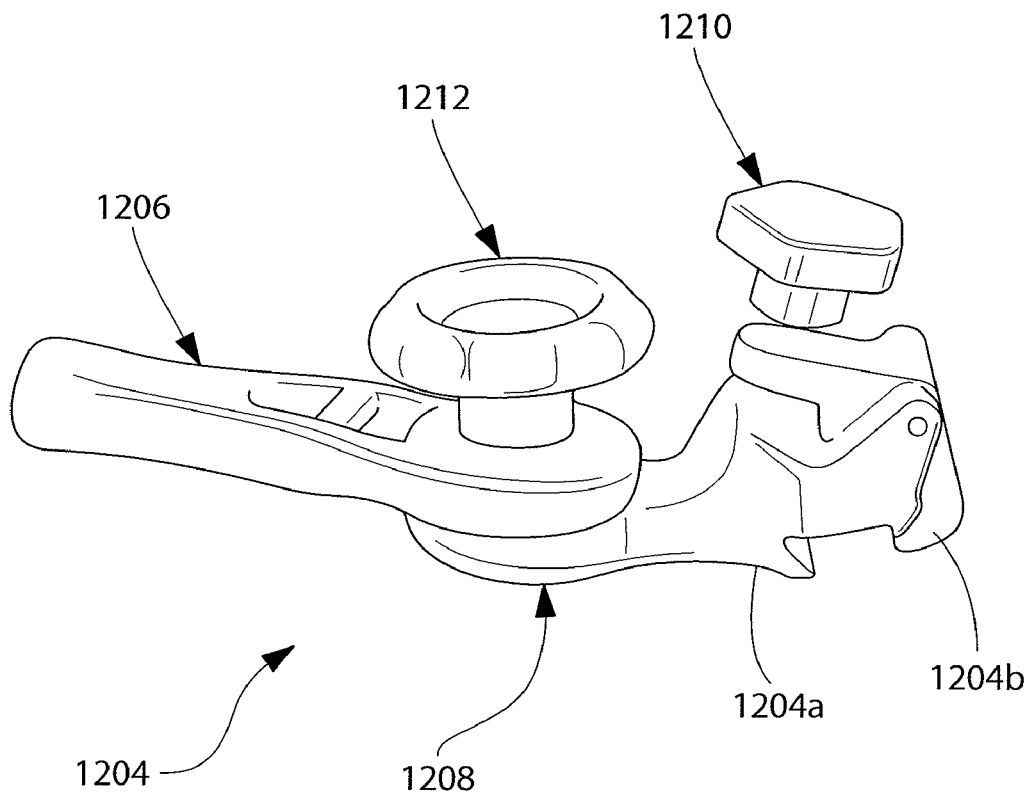

Turning to FIGS. 9A and 9B, a curvilinear articulating arm assembly such as assemblies 12, 716 (modified as will be described) may be coupled to a patient support surface 1200 (such as an operating room table) for example along a rail 1202 using a clamp 1204. Clamp 1204 includes jaws 1204a, 1204b for securing a curvilinear articulating arm assembly 12, 716 to rail 1202. In particular, assemblies 12, 716 are modified to include an extension member 1206 which is pivotable with respect to a clamp member 1208 (that includes jaw 1204a). Jaws 1204a, 1204b may be tightened against rail 1202 by tightening knob 1210 which in turn draws pivotable jaw 1204b to engage rail 1202. Extension member 1206 may be pivoted with respect to clamp member 1208 by loosening the coupling therebetween, using knob 1212. In particular, knob 1212 is coupled to a threaded shaft (not shown) which threably engages clamp member 1208. Such an arrangement may permit angular adjustment of the curvilinear articulating arm assembly 12, 716 through a range of about 180°. Also, such a clamp 1204 advantageously permits a stable mounting of an articulating arm with quick and easy adjustment of the positioning thereof. Thus, a laparoscopic instrument holder such as holder 1000, 1100 may be coupled to a curvilinear articulating arm assembly 12, 716 which further may be coupled to a clamp 1204, thus permitting the holder 1000, 1100 to be secured to a patient support surface.

While various descriptions of the present invention are described above, it should be understood that the various features can be used singly or in any combination thereof. Therefore, this invention is not to be limited to only the specifically preferred embodiments depicted herein. For example, although the holders described herein are described in the context of laparoscopic instrument holder systems that may place a camera through a port in the skin into a working cavity, the holders also may be used for example in the context of procedures that examine the interior of a bodily canal or hollow organ such as the colon, bladder, or stomach. The present invention may be applied in a variety of fields including but not limited to general surgery, orthopedics, gynecology, urology, and cardiology. In the context of laparoscopy, the systems of the present invention for example may be used to assist in surgical procedures involving the intestines, stomach, or gallbladder which may benefit from the visual inspection made possible by a laparoscope.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A laparoscopic instrument holder for positioning a laparoscopic device comprising: a central portion comprising a first member operatively associated with a second member, the members selectively movable with respect to one another along a central axis, the central portion having a proximal end defined by the first member and a distal end defined by the second member; at least three proximal rotational joints coupled to the first member proximate the proximal end; at least two distal rotational joints coupled to the second member proximate the distal end; a first ball and socket joint coupled to a distal rotational joint; a second ball and socket joint coupled to the first ball and socket joint; a clamp configured and dimensioned for retaining a laparoscopic device, the clamp coupled to the second ball and socket joint; and a coupling portion proximate a first one of the at least three proximal rotational joints.

2. The laparoscopic instrument holder of claim 1, wherein each ball and socket joint comprises a ball and a washer.

3. The laparoscopic instrument holder of claim 1, wherein the first ball and socket joint comprises a first ball and the second ball and socket joint comprises a second ball, and wherein the first and second balls are rigidly coupled to each other.

4. The laparoscopic instrument holder of claim 3, wherein the first and second balls are rigidly coupled to each other by a shaft.

* * * * *